United States Patent [19]

Belsito et al.

[11] Patent Number: 5,403,251

[45] Date of Patent: Apr. 4, 1995

[54] PATIENT POSITIONING SYSTEM AND METHOD FOR COMPUTER CONTROLED MUSCLE EXERCISING MACHINE

[75] Inventors: Anne W. Belsito, Chattanooga; Brian S. Baxter, Hixson; Paul R. Camp, Chattanooga, all of Tenn.

[73] Assignee: Chattanooga Group, Inc., Hixson, Tenn.

[21] Appl. No.: 70,989

[22] Filed: Jun. 4, 1993

[51] Int. Cl.⁶ .............................................. A63B 24/00
[52] U.S. Cl. ........................................ 482/4; 482/8; 482/142; 482/902; 601/23; 345/173
[58] Field of Search .................. 482/1, 4, 8, 52, 55, 482/57, 70–72, 75, 100, 133, 142, 901–903, 908; 128/25 R, 25 B; 73/379.01, 379.06; 601/34, 23, 24, ; 345/123, 173

[56] References Cited

U.S. PATENT DOCUMENTS

| | | |
|---|---|---|
| 3,869,121 | 3/1975 | Flavell . |
| 4,333,340 | 6/1982 | Elmeskog ................. 73/379.01 |
| 4,601,468 | 7/1986 | Bond et al. . |
| 4,691,694 | 9/1987 | Boyd et al. ..................... 482/8 X |
| 4,711,450 | 12/1987 | McArthur . |
| 4,765,615 | 8/1988 | Case ......................... 482/133 X |
| 4,786,049 | 11/1988 | Lautenschlager ........... 482/902 X |
| 4,889,108 | 12/1989 | Bond et al. . |
| 4,905,676 | 3/1990 | Bond et al. . |
| 4,934,694 | 6/1990 | McIntosh . |
| 4,976,435 | 11/1990 | Shatford et al. ............ 482/902 X |
| 4,986,534 | 1/1991 | Meier et al. ................ 482/902 X |
| 5,054,774 | 10/1991 | Belsito . |
| 5,158,074 | 10/1992 | Grellas ....................... 128/25 R |
| 5,186,695 | 2/1993 | Mangseth et al. . |
| 5,209,223 | 5/1993 | McGorry et al. ............ 128/25 B X |
| 5,244,441 | 9/1993 | Dempster et al. ............ 482/901 X |

Primary Examiner—Richard J. Apley
Assistant Examiner—Joe H. Cheng
Attorney, Agent, or Firm—Bell, Seltzer, Park & Gibson

[57] ABSTRACT

A patient positioning system for computer controlled muscle exercising machine allows for automatic positioning of large numbers of patients prior to exercises and evaluations. The patient positioning system simplifies the patient positioning process by allowing the seat and actuator to be moved, manually or automatically, in both the horizontal and vertical direction relative to each other. This is accomplished by indicating the direction in which the seat and actuator are to be moved based upon optimum exercise positions stored in a data storage means. The directions are indicated adjacent to a four way switch and on a display device for selecting the direction of movement. In response to this prompt, the direction of movement of the seat and/or actuator is selected by pressing the four way switch for the seat or the four way switch for the actuator in the direction indicated adjacent to the switch and on the display device. The seat and/or actuator are moved based on the direction selected until the optimum exercise position stored in the data storage means is reached. Once the exercise position for the particular exercise and patient is reached, i.e. automatic (standard or custom) positioning is completed, the relative positions of the seat and actuator are manually adjusted. The exercise positions are stored in the data storage means in association with a particular patient and exercise.

39 Claims, 36 Drawing Sheets

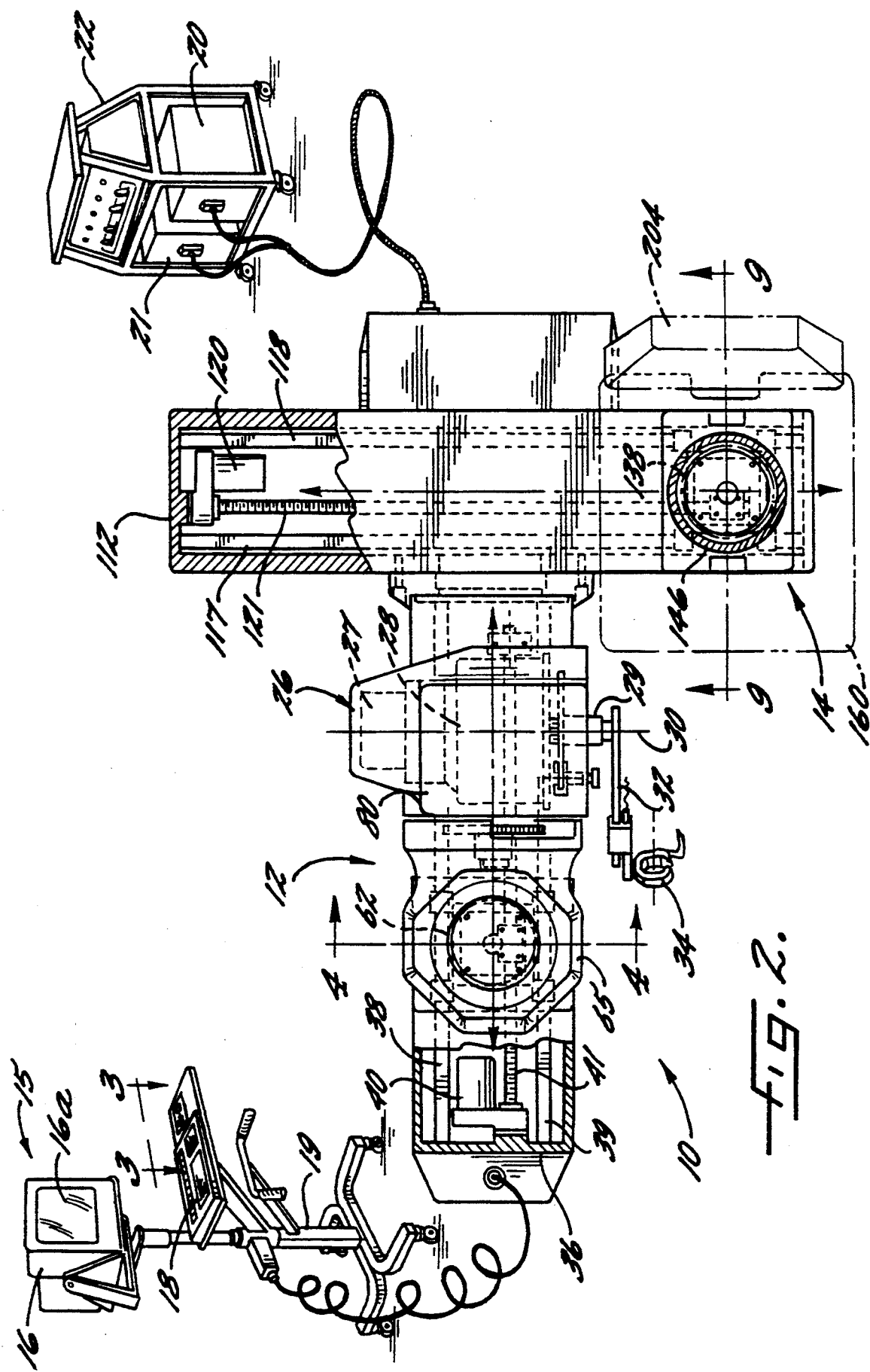

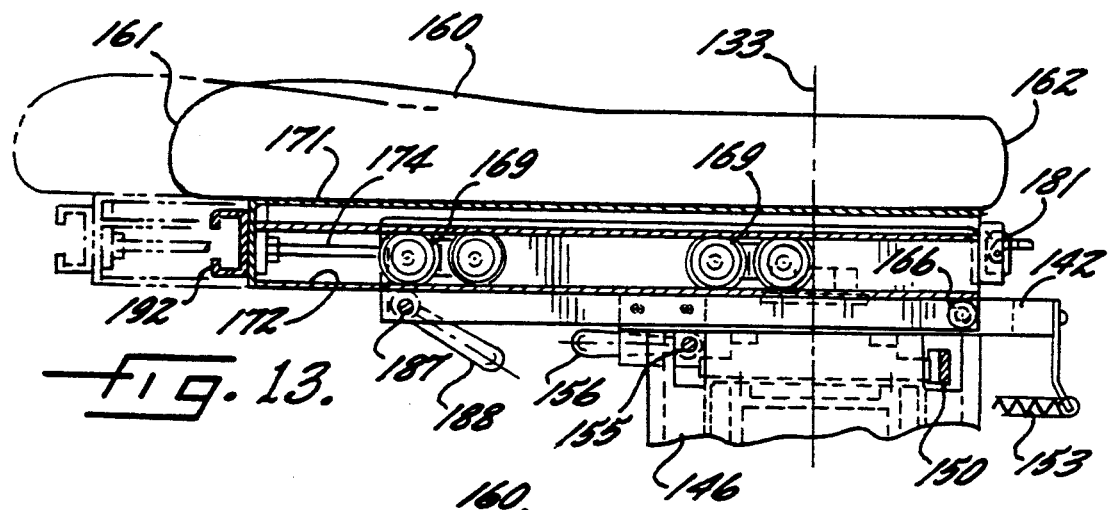
Fig. 13.
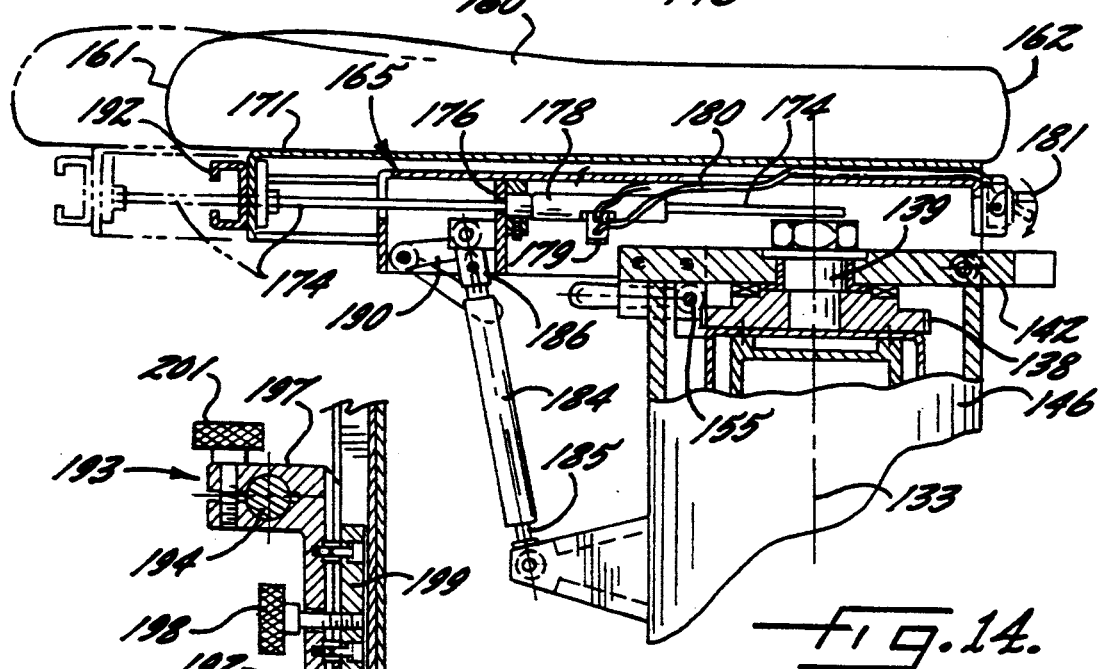
Fig. 14.
Fig. 16.
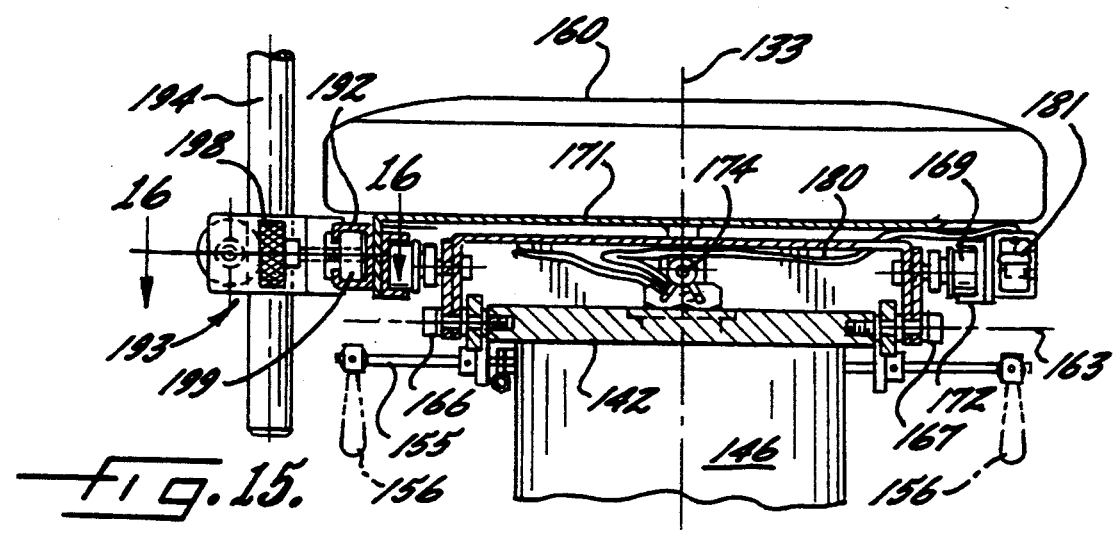
Fig. 15.

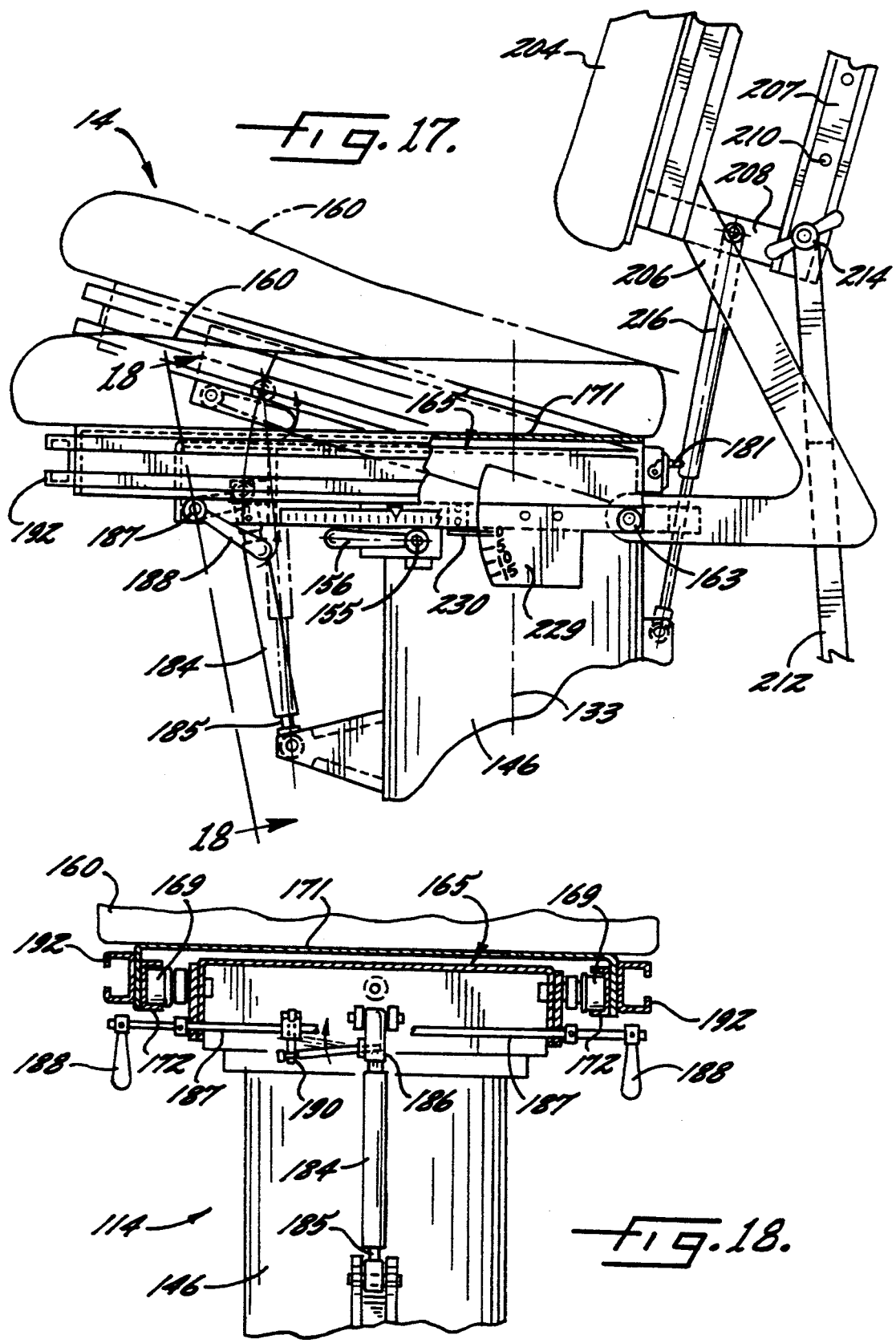

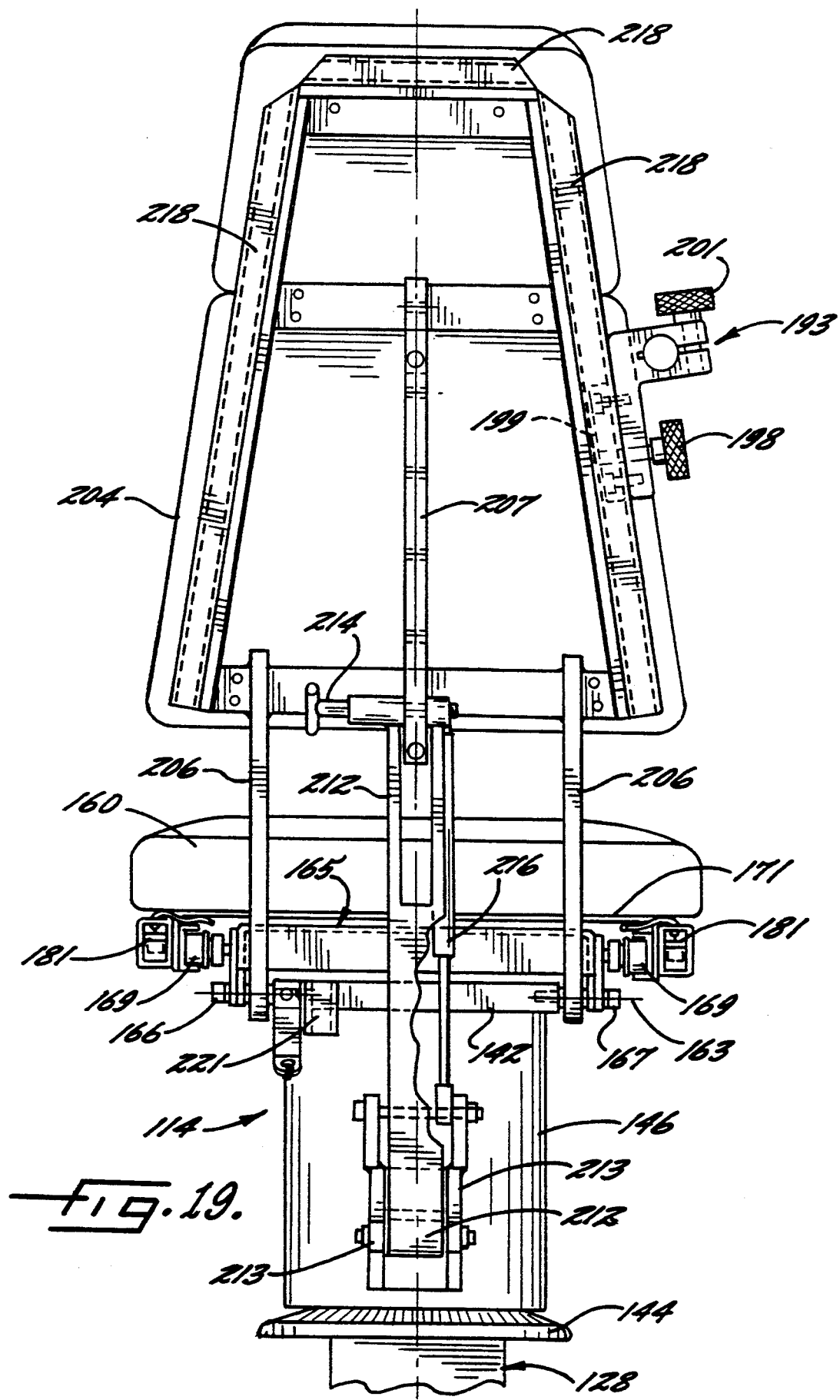

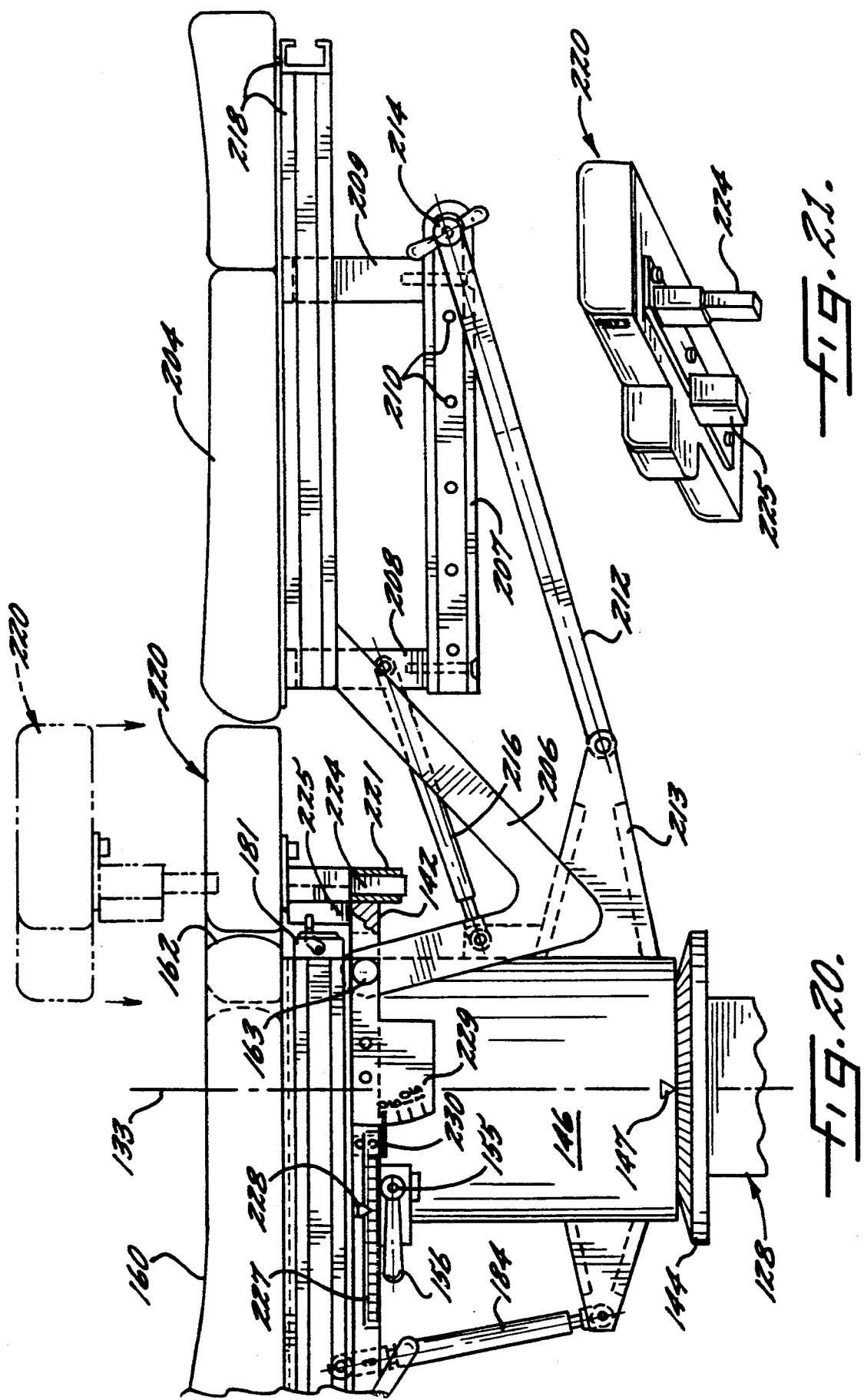

```
SET ACTUATOR TILT TO          0°
SET ACTUATOR ROTATION TO      0°
SET SAFETY START TO           0
SET SAFETY STOP TO            0
    PRESS ANYWHERE TO CONTINUE...
```

```
          AUTOMATIC POSITIONING
            ROGERS, MICHAEL M
             RIGHT KNEE EXT

MANUAL MODE

PRESS DESIRED TOGGLE ON KEYPAD TO MOVE SEAT OR ACTUATOR.

POSITIONAL DATA FOR THIS PT./SIDE/JOINT/MOVEMENT  | YES | NO |
  ALREADY EXISTS.  DO YOU WANT TO OVERWRITE IT?
```

FIG. 28M.

```
           AUTOMATIC POSITIONING
         RIGHT SHOULDER INT/EXT ROT

SELECT PATIENT
                   UP ↑

ROGERS              MICHAEL           M
     STIG                WRETZEN
     TEST
     TEST PATIENT NAME   FIRST NAME        M
     TRAINING TESTING    DATA

DOWN ↓

| ESC |         | NEW PATIENT |        | ACCEPT |
   F1: HELP
```

FIG. 28N.

```
        AUTOMATIC POSITIONING
         PATIENT INFORMATION

NAME: TEST PATIENT NAME        FIRST NAME        M
      Last                     First             Mi
WEIGHT: 268      BIRTH: 03/02/57   SEX: M
        (lb)           (mm/dd/yy)
     DIAGNOSIS: DIAGNOSIS
     PHYSICIAN: TEST
     CLINICIAN: CLINICIAN NAME
INVOLVED SIDE: RIGHT
CHIEF COMPLAINT: COMPLAINT 1
                 COMPLAINT 2
                 COMPLAINT 3
     GROUP: NEW BIG GROUP
 SUB GROUP: NEW BIG SUBGROUP

[ESC]           [RE-DO]              [ACCEPT]
F1: HELP
```

FIG. 28O.

```
              KIN-COM
             EVALUATION

[ 1         ]   [ 2       ]
         [ISOKINETIC ]   [PASSIVE  ]

[ 3         ]   [ 4       ]
         [ISOMETRIC  ]   [ISOTONIC ]

[ 5         ]   [ 6                ]
         [PROTOCOL   ]   [MUSCLE PERFORMANCE]

[ESC]
F1: HELP
```

FIG. 28P.

PATIENT POSITIONING SYSTEM AND METHOD FOR COMPUTER CONTROLED MUSCLE EXERCISING MACHINE

BACKGROUND OF THE INVENTION

The present invention relates to a patient positioning system for a computer controlled exercising machine for analysis, assessment, and evaluation of musculoskeletal performance.

U.S. Pat. No. 4,711,450 to McArthur discloses a computer controlled exercising machine of the described type, and which comprises a powered actuator having an exercise element attached thereto, the actuator being mounted on a pedestal located between two seats. The machine as disclosed in the referenced patent has been sold for several years under the trademark KIN-COM ® by Chattanooga Group Inc. of Chattanooga, Tenn. and the machine is adapted to operate in a number of different exercising modes, including isokinetic, isometric, isotonic, and constant power modes.

U.S. Pat. No. 5,504,774 to Belsito discloses a data access method and apparatus for computerized control of a muscle exercising machine, similar to that described in McArthur, allowing large amounts of data to be stored and retrieved with minimal computer skill. The muscle exercising machine displays a window or scroll box on its display containing a partial list of at least some of the patient names, exercises, dates of exercises and other data, and a selection area for highlighting one name, exercise, etc. in the partial list displayed in the window or scroll box on the display. The window or scroll box also provides up/down selection options to permit the list of names, etc., a part of which is displayed in the window, to be scrolled in the up or down direction. As a results, the muscle exercise machine may be controlled using the window and up/down options to permit exercising of standard exercises including isokinetic, isotonic, and isometric exercises.

The actuator of the KIN-COM ® machine may be elevated to a desired elevation suited for a particular patient and a particular exercising mode, and the actuator may also be rotated about a horizontal axis which extends between the two seats. In use, the patient sits or lies on one of the two seats, and the elevation and rotational orientations of the actuator are adjusted to fit the requirements of the selected exercising mode to the particular patient. In this regard, it is preferable that the rotational axis of the actuator be aligned to extend through the joint of the patient which is being exercised or evaluated.

In another prior version of the KIN-COM ® apparatus, which is known as the "125 E" model, the apparatus comprises a single seat, and the powered actuator is mounted on a support column which is pivotable about a vertical axis which extends through the seat, and so as to permit the actuator to be selectively positioned on either side or in front of the seat. Also, in the "125 E" model, the actuator is vertically movable under a powered control system, and the actuator pivots with respect to its support column about a vertical axis, and it also tilts with respect to its support column about a horizontal axis. Further, the seat is adjustable in several respects, and it comprises a seat portion and a back rest which is pivotable between upright and horizontal positions, and the seat portion and back rest are adjustable together in the longitudinal direction, and they pivot together about a vertical axis. Further, the seat portion is adjustable independently of the back rest in the longitudinal direction, and the supporting structure for the seat portion and back rest is movable vertically by a power control system.

A major problem in controlling computerized muscle exercising machines is the adjustment of the relative seat and actuator or exercise element positions for a large number of patients for numerous different exercise and evaluation modes, joints, movement patterns and sides. Relative seat and actuator positions must be stored and retrieved, or worse yet, remembered by a clinician or operator, sometimes referred to as an user, in order to adjust the positioning of a patient for a particular exercise or evaluation, joint, movement pattern and side by moving the seat and actuator prior to beginning the exercise or evaluation.

SUMMARY OF THE INVENTION

It is therefore an object of the present invention to provide an improved computer controlled exercising machine of the described type which has an improved and simplified patient positioning capability wherein the patient may be readily positioned to perform a selected exercising routine.

It is a more particular object of the present invention to provide a computer controlled exercising machine of the described type which has a patient positioning system whereby the seat and actuator of the machine may be readily located for a particular exercising mode for a particular patient.

These and other objects and advantages of the present invention are achieved in the embodiment illustrated and described herein by the provision of an automatic patient positioning system for a computer controlled muscle exercise machine which has an actuator with an output shaft for attaching an arm or exercise element thereto, and a seat. The actuator is mounted by mounting means which comprises a vertically disposed post which defines a vertical axis, a first housing member mounted to the post for rotation about the vertical axis, and a second housing member mounted to the first housing member for rotation about a horizontal axis which is fixed with respect to the first housing member, and with the actuator being mounted to the second housing member. The actuator mounting means preferably comprises a base member supporting the post, and a first drive motor for vertically moving the first and second housing members and the actuator collectively with respect to the base member, i.e. moving the actuator in the up/down direction. Further, the post may be moved horizontally along the base member in either direction along a longitudinal path of movement, and a second drive motor is provided in the base member for effecting such movement in either direction, i.e. moving the actuator in the forward/backward direction.

The seat of the computer controlled muscle exercise machine supports a patient so that the patient can engage the arm attached to the actuator. The seat is mounted by means of a base member, and a post which is mounted to the base member. The mounting means for the seat also includes a first drive motor mounted in the base member for moving the seat in the horizontal direction, i.e. moving the seat in the left/right direction, and a second drive motor mounted in the post for raising and lowering the seat, i.e. moving the seat in the up/down direction.

The patient positioning system for a computer controlled exercising machine according to the present invention readily positions the actuator and the seat at optimum settings for a particular exercise routine and for a particular patient. The patient positioning system has a position selector for selecting the direction in which the seat is moved relative to the actuator and for selecting the direction in which the actuator is moved relative to the seat. A position controller controls the movement of the seat as selected by the position selector and the movement of the actuator as selected by the position selector. Patient names, exercise names and exercise positions, i.e. relative seat and actuator positions, are stored in a data storage means such as a hard disk.

In a preferred embodiment, a data processor activates and deactivates the position selector and the position controller based upon exercise positions, or relative seat and actuator positions, stored in the data storage means. A position direction indicator such as a light emitting diode indicates the direction the seat is to be moved relative to the actuator and the direction the actuator is to be moved relative to the seat. Selection of the direction of movement of the seat and the actuator, in response to the direction indicated by the direction indicator, is accepted at the position direction input means. The position controller moves the seat and the actuator in response to the accepted selection of the direction of movement until the exercise position is reached. Once the relative exercise position is reached, it can be stored in the data storage means in association with a particular patient and exercise.

The actuator can be moved forward and backward, and up and down, relative to the seat. The seat can be moved left and right, and up and down, relative to the actuator. Two four-way patient positioning switches, one for the seat and one for the actuator, are provided adjacent the keyboard for moving the seat and actuator. The seat and actuator are moved by four motors, one for moving the seat in a horizontal direction relative to the actuator, the second for moving the seat in a vertical direction relative to the actuator, the third for moving the actuator in a horizontal direction relative to the seat, and the fourth motor for moving the actuator in the vertical direction relative to the seat. The position direction indicator, which preferably is a light emitting diode, indicates the direction, when illuminated, each four way patient positioning switch is to be pressed in order to move the seat (or actuator) to the desired position.

The patient positioning system can be operated in three different modes, namely, standard, custom and manual. While in standard mode, the seat and actuator are moved to standard relative positions retrieved from a standard patient position database, the standard relative exercise positions being optimum for the particular exercise or evaluation, joint, movement pattern and side. The seat and actuator can also be moved using the patient positioning switches to custom relative positions retrieved from a custom patient position database, the custom relative positions being previously selected patient exercise positions for a particular patient, exercise or evaluation, joint, movement pattern and side and stored in the custom patient position database. Finally, the patient positioning system can be placed in manual mode at any time during or after completion of standard or custom mode by manipulating the patient positioning switches, during which the seat and actuator will move continuously while the patient positioning switches are manipulated. Once the desired exercise position is reached, it can be stored in association with a particular patient and exercise.

During standard and custom mode, the patient positioning system, based upon the standard position settings retrieved from the standard patient position database or the custom position settings retrieved from the custom patient position database, prompts the user or clinician to move the seat and/or actuator by illuminating one of four position indicators located adjacent one of the patient position switches and corresponding to the direction the seat and/or actuator needs to be moved. Instructions are also displayed on the display. The position indicator remains illuminated and the display remains displayed until the seat and/or actuator reaches the appropriate forward/backward, left/right or up/down position as controlled by manipulation of the patient control switch in the direction indicated by the illuminated position indicator and on the display. The patient positioning system continues to prompt the user until each setting forward/backward, left/right, and up/down for the seat and actuator has been reached. Once the standard or custom patient positions have been reached, the user or clinician may further adjust the seat and/or actuator by entering manual mode. Whether or not manual node is entered, the patient position, i.e. position of the actuator and seat, can be stored in the custom patient position database for future retrieval and adjustment of the seat and actuator.

BRIEF DESCRIPTION OF THE DRAWINGS

Some of the objects and advantages of the present invention having been stated, others will appear as the description proceeds, when taken in conjunction with the accompanying drawings, in which;

FIG. 2 is a partly sectioned and partly schematic top plan view of the apparatus;

FIG. 13 is a fragmentary and sectioned side elevation view of the seat assembly taken substantially along the line 13—13 of FIG. 10;

FIG. 14 is a view similar to FIG. 13 but taken substantially along the line 14—14 of FIG. 10;

FIG. 15 is a sectioned side elevation view taken substantially along the line 15—15 of FIG. 10;

FIG. 16 is a fragmentary and sectioned view of a mounting car and taken substantially along the line 16—16 of FIG. 15;

FIG. 17 is a fragmentary and partly sectioned side elevation view of the seat assembly and illustrating the seat portion in its lowered position in solid lines and in its upwardly tilted position in dashed lines;

FIG. 18 is a fragmentary and partly sectioned front elevation view of the seat assembly and taken substantially along the line 18—18 of FIG. 17;

FIG. 19 is a rear elevation view of the seat assembly;

FIG. 20 is side elevation view of the seat assembly with the back rest in its horizontal position, and further illustrating the intermediate pad;

FIG. 21 is a perspective view of the intermediate pad of the seat assembly;

DETAILED DESCRIPTION OF THE PREFERRED EMBODIMENT

The present invention will now be described more fully hereinafter with reference to the accompanying drawings, in which a preferred embodiment of the invention is shown. This invention may, however, be embodied in many different forms and should not be construed as limited to the embodiment set forth herein. Rather, the illustrated embodiment is provided so that this disclosure will be thorough and complete, and will fully convey the scope of the invention to those skilled in the art. Like numbers refer to like elements throughout.

Overview of the Computer Controlled Exercise Machine

Figure 1:
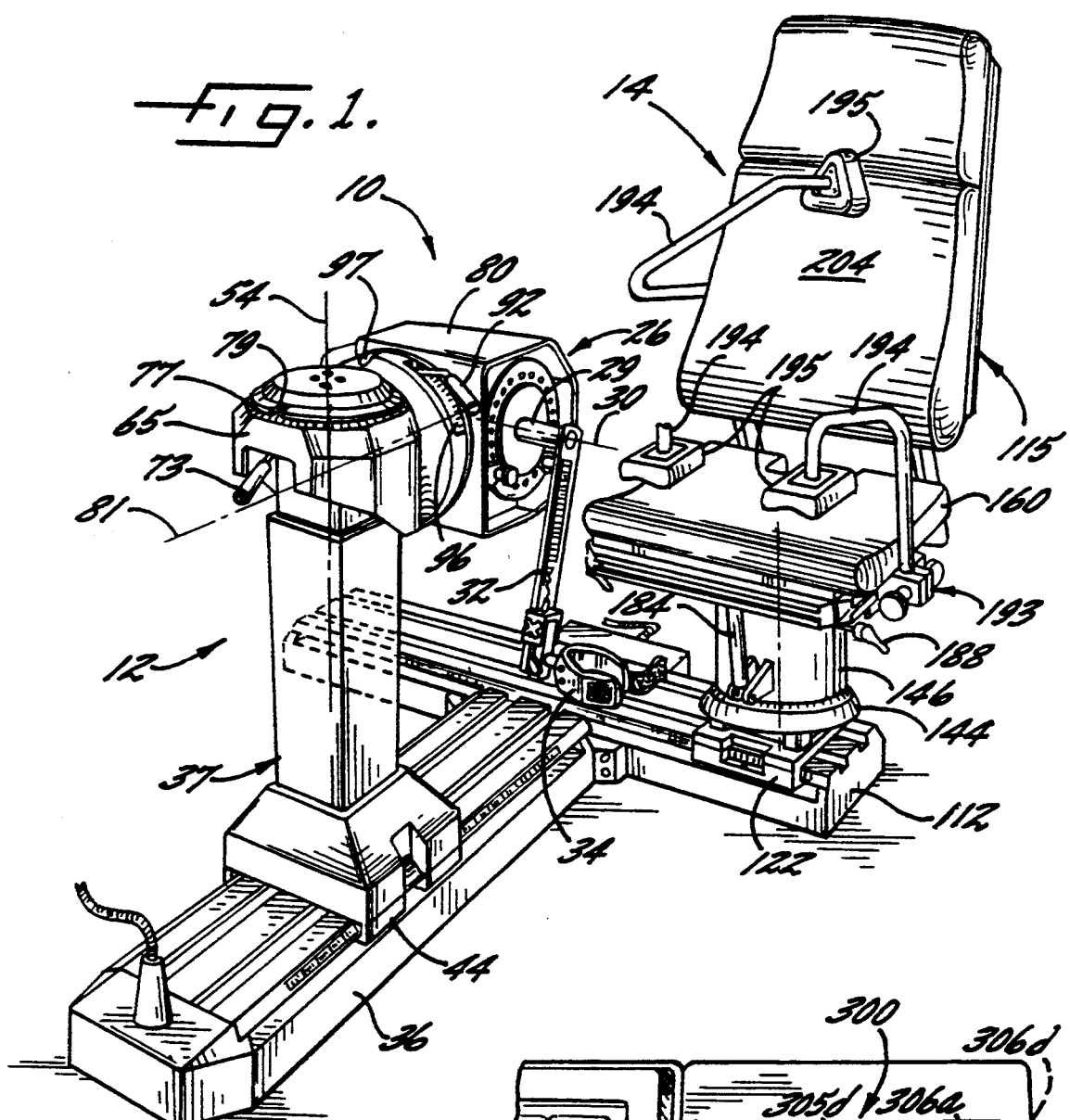
FIG. 1 is a perspective view showing a computer controlled exercising machine which embodies the features of the present invention.

Referring to FIGS. 1 and 2, a computer controlled exercising machine which embodies the features of the present invention is illustrated generally at 10. The apparatus 10 consists of an actuator assembly 12 and an adjacent patient support assembly 14. The positioning of the actuator assembly and patient support assembly, as well as the mechanical operation of the apparatus, is controlled by a computer controller 15, which in turn comprises a monitor 16 including a display screen 16a, and a keyboard 18, which are mounted on a portable stand 19. Computer controller 15 also includes a central processing unit 20 and a box assembly 21 containing, for example, floppy and hard disk drives, which are mounted on another portable stand 22. A computer controller of this type is further described in U.S. Pat. No. 5,054,774 to Belsito, the disclosure of which is expressly incorporated herein by reference.

The Actuator Assembly

The actuator assembly 12 of the apparatus 10 is best seen in FIGS. 1, 2, and 4-8, and it includes a rotary actuator 26 which preferably comprises a DC reversible and variable speed electric servo motor 27 having a power rating of about 1½ horsepower. The motor 27 has an output which acts through a 100:1 gear box 28, to turn an output shaft 29 which is mounted for rotation about a rotational axis 30. A radial arm 32, which typically has a length of about 17 inches, is connected to the output shaft 29, and the arm 32 in turn releasably mounts a patient engaging member 34 which is adapted for the particular exercising mode to be performed with the patient. The patient engaging member 34 is releasably and slidably mounted to the arm 32 so as to permit members of different configuration, designed for a variety of exercising routines, to be selectively attached to the arm. The combination of the member 34 and the arm 32 may be referred to as the exercise element. In addition, the member 34 includes a load cell (not shown) for measuring the force applied thereto by the patient, and for the purposes more fully described in U.S. Pat. No. 4,711,450 to McArthur, the disclosure of which is expressly incorporated herein by reference.

The rotary actuator 26 is mounted by a structure which includes an actuator base member 36 having a vertical post 37 slidably mounted thereto. More particularly, the base member 36 is adapted to be positioned on the supporting floor, and it includes a pair of longitudinally extending slides 38, 39. Also, an AC reversible electric motor 40 is mounted in the base member, and the output of the motor is connected to a longitudinally extending threaded drive screw 41 which is disposed between the slides.

The vertical post 37 is slidably mounted to the base member 36, and the post 37 includes a lower frame 44 which includes a pair of downwardly open C-shaped grippers 45, 46 for engaging the two slides 38, 39 respectively. Also, the lower frame 44 mounts a nut 47 which threadedly engages the drive screw 41, so that rotation of the drive motor 40 and the screw 41 causes the post 37 to slide back and forth along a longitudinal (forward/backward) path of movement defined by the slides 38, 39. The output of the motor 40 is connected to a conventional potentiometer (not shown) which signals the rotational position of the motor and thus the longitudinal (forward/backward) position of the post 37 to the computer controller 15.

Figure 4:
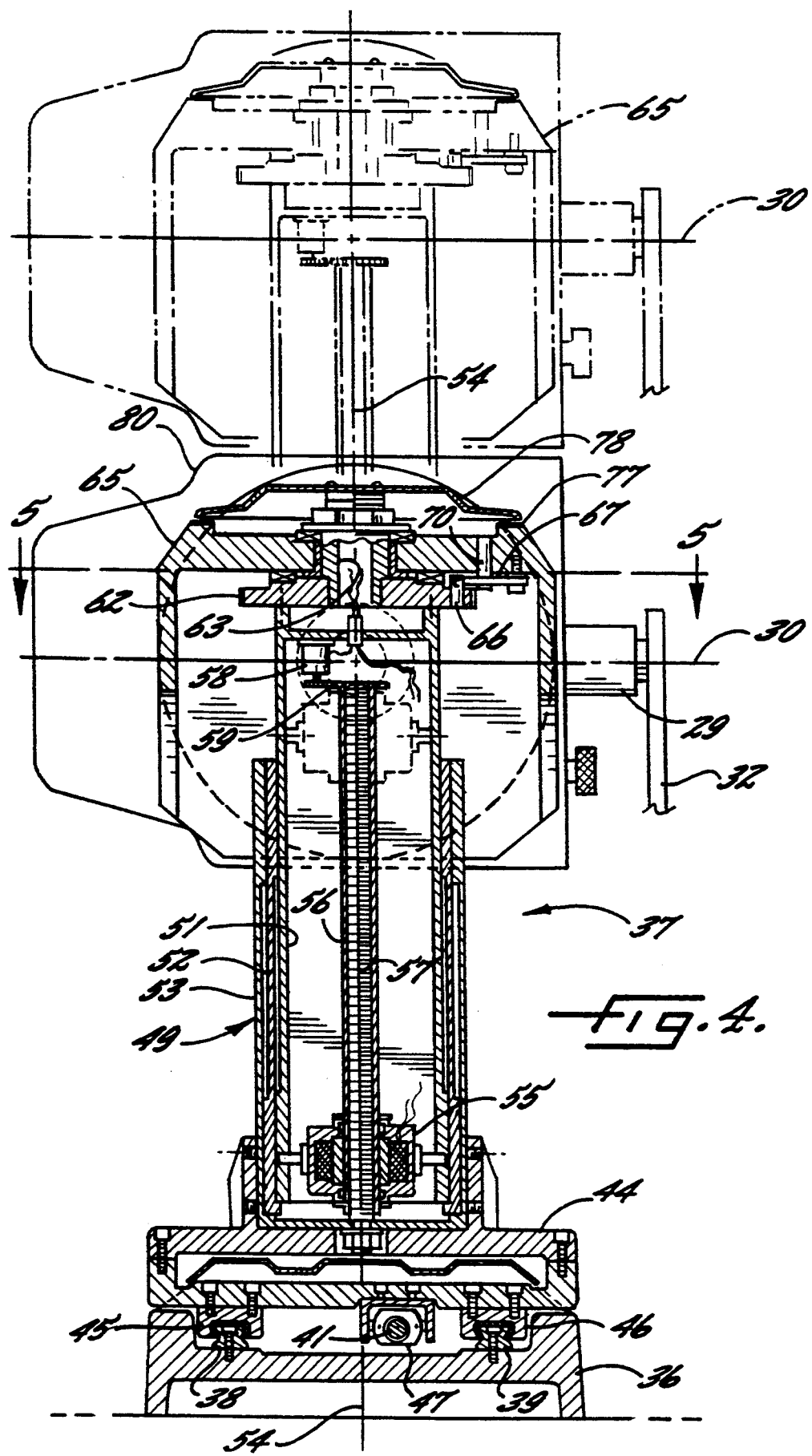
FIG. 4 is a sectioned side elevation view of the actuator assembly of the apparatus and taken substantially along the line 4—4 of FIG. 2.

The post 37 further includes a telescopic pillar 49 which is fixed to the lower frame 44. As best seen in FIG. 4, the telescopic pillar 49 includes three concentric tubular members 51, 52, 53 of rectangular outline in transverse cross-section, and which are disposed coaxially about a vertical axis 54. An AC reversible electric drive motor 55 is fixed in the interior tubular member 51, and the output of the drive motor 55 is connected to a sleeve 56 which is coaxial with the vertical axis 54, and which is threaded onto a vertical threaded rod 57 which is also coaxial with the vertical axis 54 and is fixed to the lower frame 44.

Rotation of the drive motor 55 thus causes the sleeve 56 to rotate upon the threaded rod 57, which in turn causes the interior tubular member 51 to lift upwardly or return downwardly. Upon lifting a predetermined distance, the interior tubular member 51 engages the intermediate member 52, so as to lift the intermediate member, and likewise, the intermediate member 52 later engages the outer member 53 to define the limit of upper movement.

The telescopic pillar 49 as described above is itself of conventional design, and a pillar of the described configuration is manufactured by Magnetic Elektromotoran AG of Liestal, Germany. In the present apparatus, however, a potentiometer 58 is added, which is mounted in the pillar 49 so as to engage a gear wheel 59 which is coaxially mounted at the upper end of the sleeve 56, so that the rotational movement, and thus the elevation of the pillar may be determined and signalled to the computer controller.

The upper end of the interior member 51 is closed, and a circular external gear 62 is coaxially fixed thereto. A tubular shaft 63 is coaxially mounted to the gear 62, and the shaft 63 rotatably mounts a first housing member 65, such that the first housing member is free to rotate with respect to the post 37 about the vertical axis 54.

Figure 5:
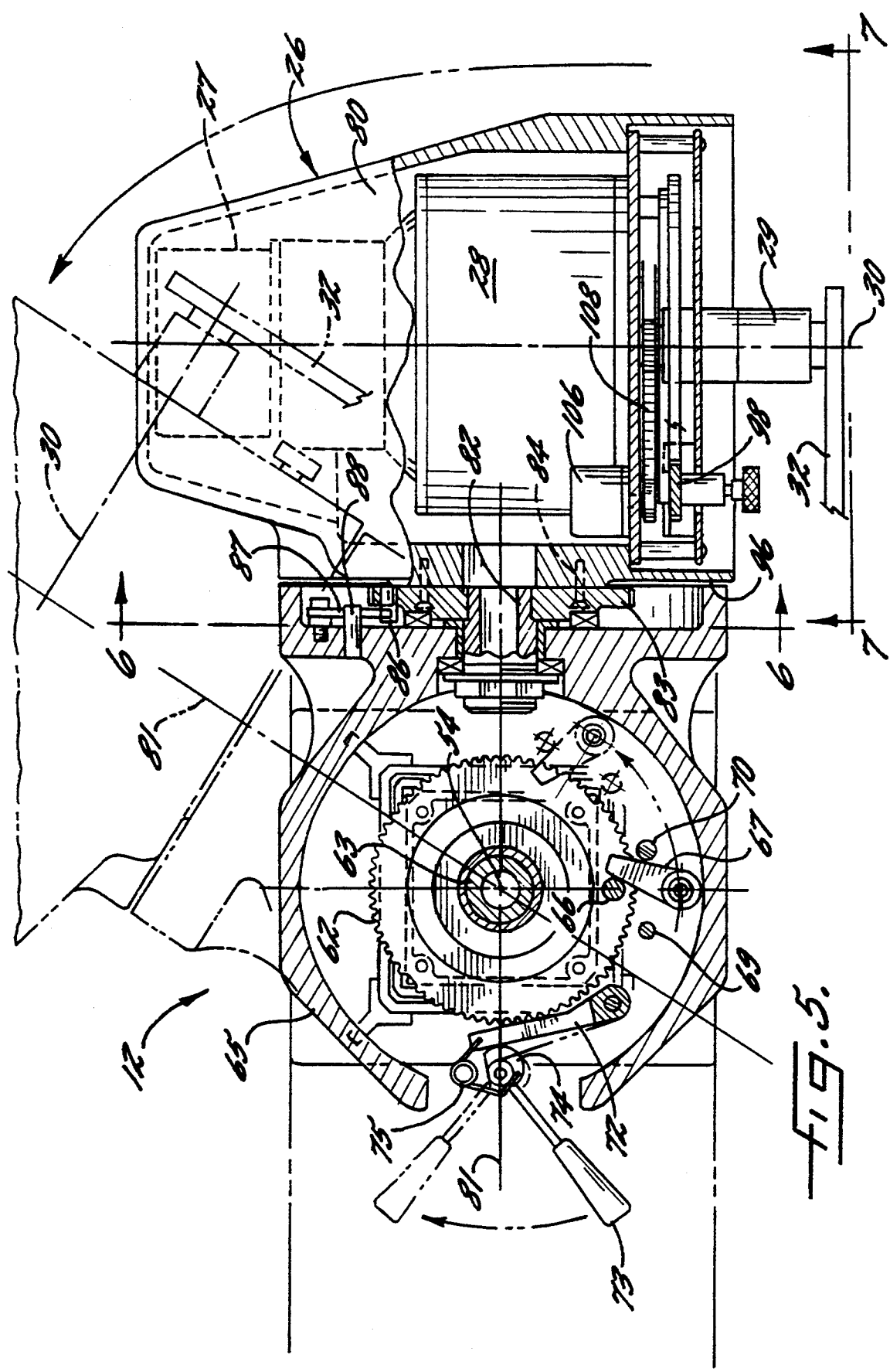
FIG. 5 is a sectioned plan view of the actuator assembly taken substantially along the line 5—5 of FIG. 4.

As best seen in FIG. 5, an abutment assembly is mounted to the post 37 and the first housing member 65 for precluding rotational movement of the first housing member 65 about the vertical axis 54 beyond a range which is somewhat greater than 360°. This abutment assembly includes an upright pin 66 fixed to the gear 62, and a lever arm 67 pivotally mounted to the first housing member for rotation about a vertical axis which is spaced from but parallel to the axis 54. A pair of pins 69, 70 are mounted to the first housing member adjacent the opposite sides of the lever arm 67 so as to permit limited pivotal movement of the lever arm. As seen in solid lines in FIG. 5, the first housing member 65 is positioned at the limit of its clockwise rotational movement, and it is adapted to rotate counterclockwise until the lever arm 67 engages the opposite side of the pin 66, which in turn causes the lever arm 67 to pivot into engagement with the side pin 69, thereby precluding further rotation. By this arrangement, the first housing member is able to rotate through a range slightly greater than 360°, e.g. about 380°.

To temporarily lock the first housing member 65 in a selected position, there is provided a rack gear 72 which is pivotally mounted to the first housing member 65. The movement of the rack gear 72 is controlled by a lever arm 73, which is also pivotally mounted to the first housing member 65, and which mounts a cam 74 for engaging the rack gear 72. Thus, as illustrated in FIG. 5, movement of the lever arm 73 counterclockwise to its illustrated solid line position causes the rack gear 72 to engage the circular gear 62 and thus preclude rotation of the first housing member, whereas movement of the lever arm 73 in the clockwise direction to the dashed line position releases the rack gear 72. A spring 75 is provided to separate the rack gear 72 from the circular gear 62 in this position, and thus permit rotation of the first housing member 65 within the range as described above.

For the purpose of permitting a visual determination of the rotational position of the first housing member 65 about the vertical axis 54, the upper portion of the first housing member mounts a circular scale 77 which is coaxial with the vertical axis 54 (FIGS. 1 and 4), and the upper end of the tubular shaft 63 mounts a circular cover plate 78. The cover plate 78 includes a pointer in the form of a narrow slot 79 on its outer periphery, which permits the scale to be read by the operator.

The actuator mounting means further comprises a second housing member 80 which is mounted to the first housing member 65 for rotation about a horizontal axis 81 (FIGS. 1 and 5) which is fixed with respect to the first housing member 65. More particularly, and as best seen in FIG. 5, the horizontal axis 81 perpendicularly intersects the vertical axis 54 of the post. This mounting arrangement includes a tubular shaft 82 which is rotatably mounted to the first housing member 65 coaxially with respect to the horizontal axis 81, and the shaft 82 fixedly mounts a circular gear 83 thereto, which is also coaxial with the horizontal axis 81. The gear 83 in turn mounts the second housing member 80 by means of bolts 84.

Figure 6:
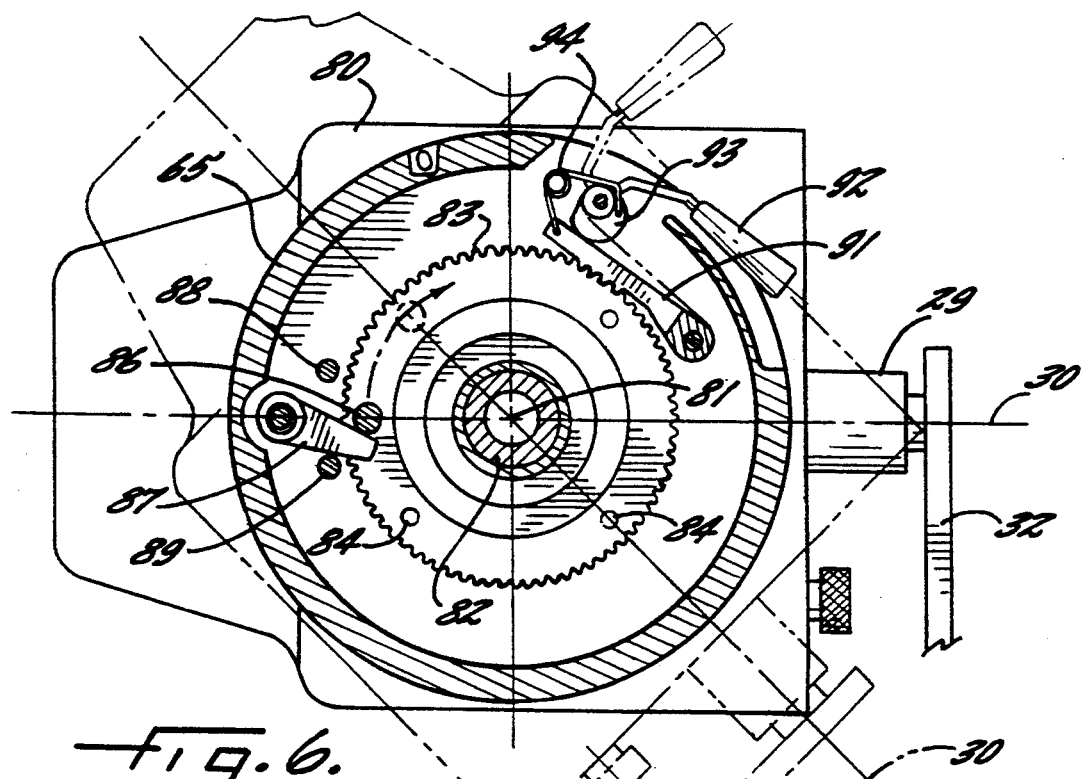
FIG. 6 is a sectioned side elevation view of the actuator assembly taken substantially along the line 6—6 of FIG. 5.
Figures 7, 8:
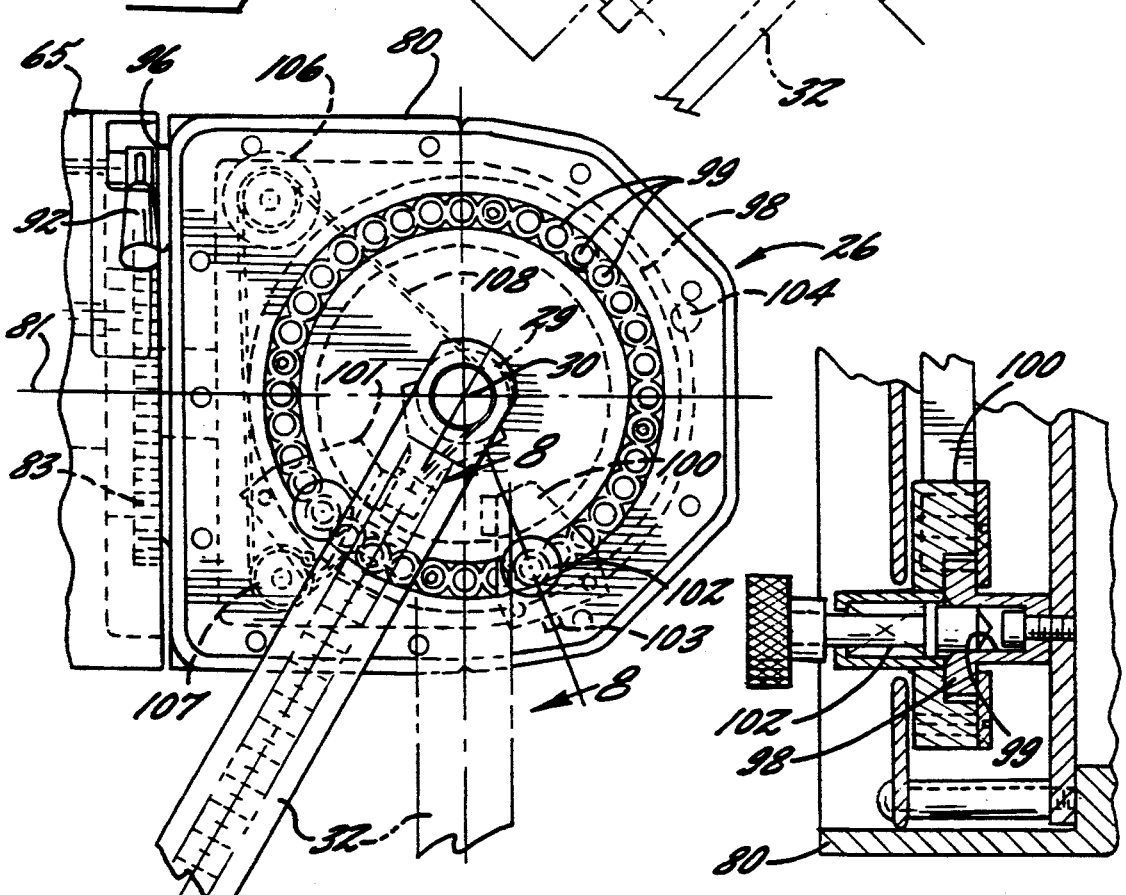
FIG. 7 is a side elevation view of the actuator assembly taken substantially along the line 7—7 of FIG. 5.
FIG. 8 is an enlarged sectional taken substantially along the line 8—8 of FIG. 7.

As best seen in FIGS. 5 and 6, the second housing member 80 includes an abutment assembly which is similar to that described above, and which is for the purpose of limiting the rotational range of the second housing member 80 about the horizontal axis 81. This abutment assembly comprises a pin 86 fixed to the gear, a lever arm 87 pivotally mounted to the first housing member 65, and a pair of side pins 88, 89 fixed to the first housing member 65. The operation of this abutment assembly is substantially identical to that described above, and it will accordingly be understood that the gear 83 and the second housing member 80 may be rotated clockwise through a range which is somewhat greater than 360° from the position illustrated in FIG. 6.

A rack gear 91, a lever arm 92, cam 93, and spring 94 are also mounted to the second housing member 80, so as to permit the second housing member to be temporarily locked with respect to the first housing member, in the manner described above with respect to the rack gear 72.

For the purpose of permitting a visual determination of the rotational position of the second housing member 80 about the horizontal axis 81, there is provided a circular scale 96 on the end surface of the second housing member 80, with the scale 96 being coaxial with the horizontal axis 81. The adjacent portion of the first housing member 65 includes a narrow slot 97, which permits the scale to be read by the operator.

The DC servo motor 27 and gear reducer 28 of the actuator are mounted within the second housing member 80, such that the rotational axis 30 of the output shaft 29 perpendicularly intersects the horizontal axis 81. Also, it will be seen that the rotational axis 30 is horizontally offset from the vertical axis 54 of the post 37 a distance sufficient to permit the second housing member 80 to freely rotate a full 360° about the horizontal axis 81. This offset distance is preferably at least about 15 inches, and as a result, the rotational axis 30 can be disposed vertically in either direction, and horizontally in either direction.

The actuator assembly 12 further includes a limitation system for limiting the rotational movement of the output shaft 29, and thus the radial arm 32, about the rotational axis 30. This limitation system includes a ring-like plate 98 which is mounted to the second housing member 80 so as to coaxially surround the rotational axis 30, and the plate 98 includes a plurality of openings 99 spaced circumferentially thereabout. Also, two limit blocks 100, 101 are provided which are each slidably mounted to the plate 98 and adapted to be locked in a selected one of the openings by means of a releasable pin 102, with a right-hand one of the blocks 100 being configured to engage the arm 32 so as to limit its counterclockwise movement and with the other or left-hand block 101 being configured to engage the arm 32 so as to limit its clockwise movement.

The right-hand block 100 mounts a pin 103 which engages a stop 104 on the second housing member, to define the full counterclockwise position of the arm and a maximum range of about 270° when the left-hand block is mounted adjacent the right-hand block. To set the arm 32 for movement outside this range, the arm 32 is rotated clockwise to the end of the 270° range, and the right-hand block 100 is moved about the ring-like plate 98 until its pin 103 engages the other side of the stop 104. The actuator may then be operated at the other end of its full 360° range.

The second housing member 80 also mounts a tachometer 106 and a potentiometer 107, which are operatively connected to the output shaft via drive belt 108. The tachometer and potentiometer send signals representing the speed and rotational position of the output shaft, respectively, to the computer controller 15, for the purpose of controlling the operation of the apparatus in the manner more fully described in the above-cited prior patent to McArthur.

The Patient Support

The patient support assembly 14 of the apparatus 10 comprises a seat base member 112, a vertical post 114 slidably mounted to the base member 112, and a seat assembly 115 which is mounted to the upper end of the post 114. The base member 112 is adapted to rest upon the supporting floor and so as to define a lateral direction which is perpendicular to the longitudinal direction defined by the actuator base member 36.

The seat base member 112 includes a pair of laterally directed slides 117, 118 which define a lateral path of travel. Also, an AC reversible electric motor 120 is mounted in the base member 112 and the output of the motor is connected to a laterally extending threaded drive screw 121 which is disposed between the slides 117, 118. The output of the motor 120 is also connected to a potentiometer (not shown) for signalling the lateral (left/right) position of the seat assembly 115 to the computer controller 15.

As best seen in FIG. 2, the longitudinal (forward-/backward) path of movement of the actuator is disposed perpendicular to and on one side of the lateral (left/right) path of movement of the seat assembly, and the forward end of the longitudinal path of movement is disposed immediately adjacent the lateral path of movement at about its midpoint along the length of the lateral path of movement.

The seat post 114 includes a lower frame 122 which includes a pair of downwardly open C-shaped grippers 124, 125 for engaging the two slides 117, 118 respectively. Also, the lower frame 122 mounts a nut 126 which threadedly engages the drive screw 121, so that rotation of the drive motor 120 causes the post 114 to slide back and forth along the lateral path of movement defined by the slides 117, 118. The post 114 further includes a telescopic pillar 128 which is fixed to the frame 122, and which has a construction corresponding to that of the actuation pillar 49 as described above. Generally, the seat pillar 128 comprises an interior tubular member 129, an intermediate tubular member 130, and an outer tubular member 131, which telescope with respect to each other. Also, a threaded rod 132 is fixed to the frame 122 so as to coaxial with the vertical axis 133 of the seat post 114, and a sleeve 134 is threaded upon the rod 132. An AC reversible drive motor 135 is mounted in the interior tubular member to effect rotation of the sleeve 134 and thus telescopic extension and retraction of the pillar 128 in a manner corresponding to that described above with respect to the actuation pillar 49. Also, a potentiometer 136 is provided which signals the elevation (up/down position) of the pillar 128 to the computer controller 15.

The upper end of the interior tubular member 129 is closed, and a circular external gear 138 is coaxially fixed thereto. A shaft 139 is coaxially mounted to the gear 138, and the shaft 139 rotatably mounts a mounting plate 142, such that the mounting plate 142 is free to rotate about the vertical axis 133.

A cylindrical inner sleeve 143 is coaxially fixed to the gear 138 so as to surround the pillar 128, and the lower end of the sleeve 143 includes a surrounding collar 144, which has an angular scale printed thereon. A cylindrical outer sleeve 146 depends from the mounting plate 142 so as to encircle the inner sleeve 143. The lower edge of the outer sleeve 146 overlies the circular collar 144 and includes a pointer 147 (FIG. 20), so that the user can visually determine the angular position of the mounting plate 142 and thus the seat assembly 115.

Figure 11:
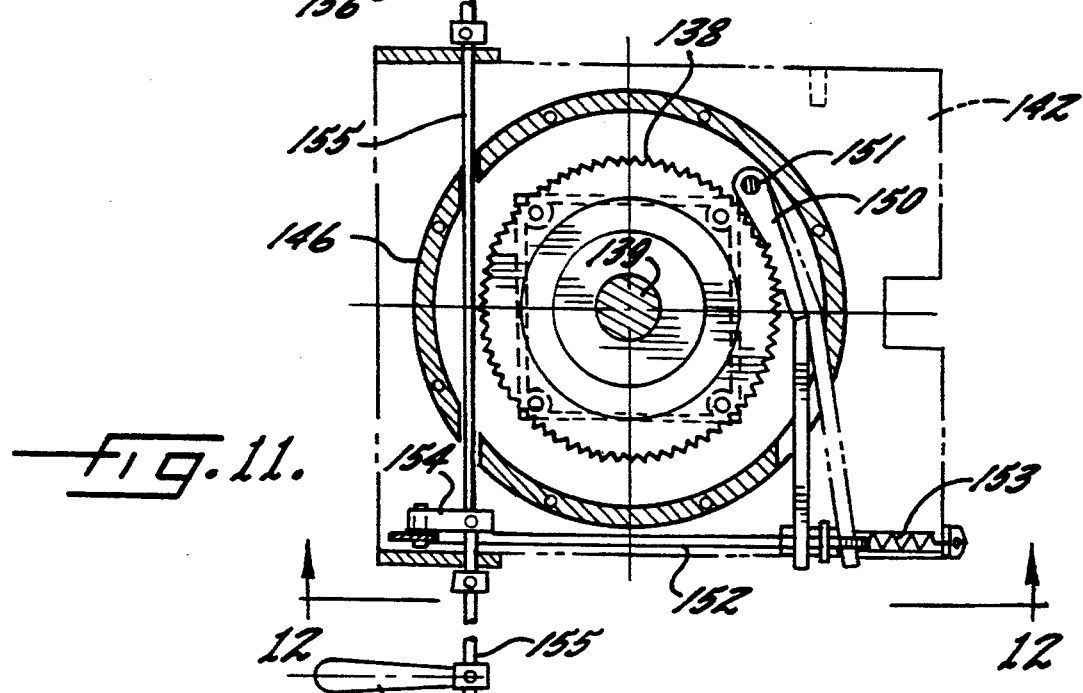
FIG. 11 is a fragmentary and sectioned top plan view taken substantially along the line 11—11 of FIG. 9.
Figure 12:
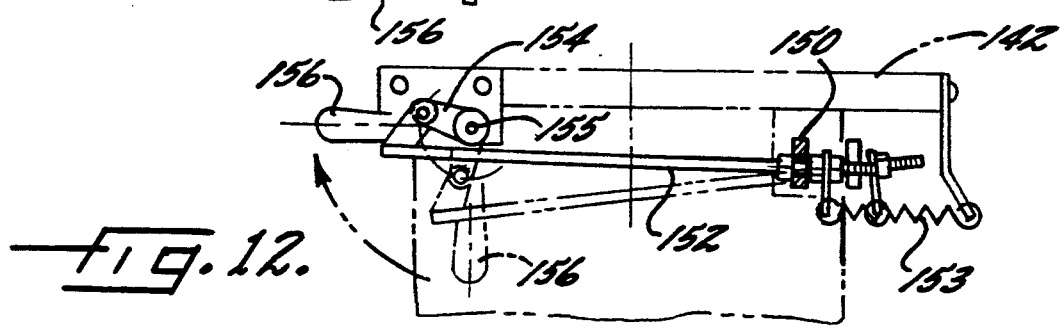
FIG. 12 is a fragmentary side elevation view taken substantially along the line 12—12 of FIG. 11.

To permit the rotational position of the mounting plate to be adjusted and locked in a selected position, there is provided a locking rack 150 (FIG. 11) which is pivotally mounted to the mounting plate at 151, and which is adapted to selectively engage the circular gear. The locking rack 150 has a free end which is connected to a push-pull rod 152, which in turn is biased toward the right as seen in FIG. 11 by a spring 153, so as to withdraw the locking rack 150 from the circular gear 138 and thus permit free rotation of the mounting plate 142. To preclude such rotation, the left end of the push-pull rod 152 is connected via a toggle linkage 154 to a transverse control rod 155 which is rotatably mounted to the mounting plate 142. The control rod 155 is fixed to the upper arm of the linkage 154, and a handle 156 is mounted to each end of the rod 155 for permitting the rod to be manually rotated. Thus when the handle 156 is rotated clockwise as seen in FIG. 12, the toggle linkage 154 acts to draw the push-pull rod 152 toward the left to pivot the locking rack 150 into engagement with the circular gear 138. By pivoting the handle 156 so that the linkage 154 moves past its "dead center" position, the linkage will hold the locking rack 150 in contact with the circular gear 138, until the handle 156 is again moved counter clockwise so as to release the linkage and permit the spring to withdraw the locking rack from the circular gear.

The seat assembly 115 comprises a relatively flat and cushioned seat portion 160, which is mounted to the mounting plate 142 and which defines a front edge portion 161 and a rear edge portion 162. The means mounting the seat portion 160 to the mounting plate 142 permits selective slidable movement relative to the mounting plate along a generally horizontal direction which extends between the front and rear edge portions and between a forward position and a rearward position, note FIGS. 13 and 14, and it also permits selective pivotal movement of the front edge portion 161 relative to the rear edge portion 162 about a first horizontal axis 163 (FIG. 15) which is perpendicular to the horizontal direction, and so as to permit the front edge portion 161 to be lifted with respect to the rear edge portion 162 and thereby tilt the seat portion 160.

The mounting means which permits the above described movements of the flat seat portion 160 is best seen in FIGS. 13-15, and it includes a seat subframe 165 which is pivotally mounted to the mounting plate 142 for pivotal movement the horizontal axis 163 defined by the pins 166, 167 (FIG. 15) and which is perpendicular to the above-identified horizontal direction of seat portion movement. The opposite side edges of the seat subframe each mount two pairs of roller assemblies 169, note FIG. 13. The mounting means further includes a seat primary frame 171 which is fixed to the flat seat portion 160, and the primary frame 171 includes opposite sides which mount opposing, C-shaped channels 172 (FIG. 15) which receive the roller assemblies 169 of the seat subframe 165.

The mounting means for the seat assembly further includes a longitudinally extending slide rod 174 which is connected to forward edge of the seat primary frame 171 and slidably extends through a transverse plate 176 which is fixed to the seat subframe 165, note FIG. 14. A locking sleeve 178 of conventional design is mounted so as to coaxially surround the slide rod 174 and the sleeve 178 is fixed to the flange 176 and it includes a clip 179 which releasably engages the rod. A locking sleeve and clip of this type is conventional, and is further described in U.S. Pat. Nos. 3,760,911 and 3,860,098. The clip 179 is connected to a flexible control wire 180 which leads to a release switch 181, such that upon manual closing of the switch 181 the clip 179 disengages the slide rod 174, so as to permit the seat primary frame 171 to slide forward and back with respect to the seat subframe 165 and mounting plate 142.

The mounting means for the seat assembly also includes a gas spring 184 which includes a tubular cylinder having an internal piston (not shown) which is connected to a plunger 185, and the plunger extends from the lower end of the cylinder and is pivotally attached to the outer sleeve 146 of the post 114. A cap 186 at the opposite end is pivotally connected to the seat subframe 165. A release mechanism for the gas spring 184 is provided which includes the cap 186 and a transverse control rod 187 (FIGS. 17 and 18) which extends between the sides of the seat subframe, with a handle 188 on each end. The control rod 187 mounts a lever 190, which in turn is connected to the cap 186 of the gas spring 184. The construction of the gas spring 184 is conventional, and upon rotation of the control rod 187 counter clockwise as seen in FIG. 17, the gas is released from one side of the piston to the other, causing the plunger 185 to be extended and the seat subframe 165 and seat portion 160 to be tilted upwardly. To lower the seat portion, the handle 188 is rotated counter clockwise and the seat portion is manually pushed downwardly against the force of the gas spring, and so as to cause the gas to return to the one side of the piston.

An outwardly open C-shaped car track 192 is fixed to each of the opposite sides of the seat primary frame 171, and a further car track 192 is mounted along the front edge of the seat primary frame. These car tracks are adapted to receive and slidably mount one or more car assemblies 193, note FIGS. 15 and 16, which are configured to mount the rod portion 194 of a patient engaging pad 195 in the manner best seen in FIG. 1. More particularly, each car assembly 193 has two arms 196, 197 disposed in an L-shaped configuration as seen in FIG. 16, with one arm 196 having an aperture to receive a threaded member 198 which threadedly engages a bar 199 located within the car track 192. Thus, upon tightening of the threaded member 198, the assembly may be locked in a selected position. The other arm 197 is split, with a bore extending therethrough, and a threaded member 201 is interconnected between the split sections so as to permit the rod portion 194 which is received in the bore to be releasably gripped. The rod portion and the patient engaging pad 195, may take different configurations as seen in FIG. 1.

Figure 9:
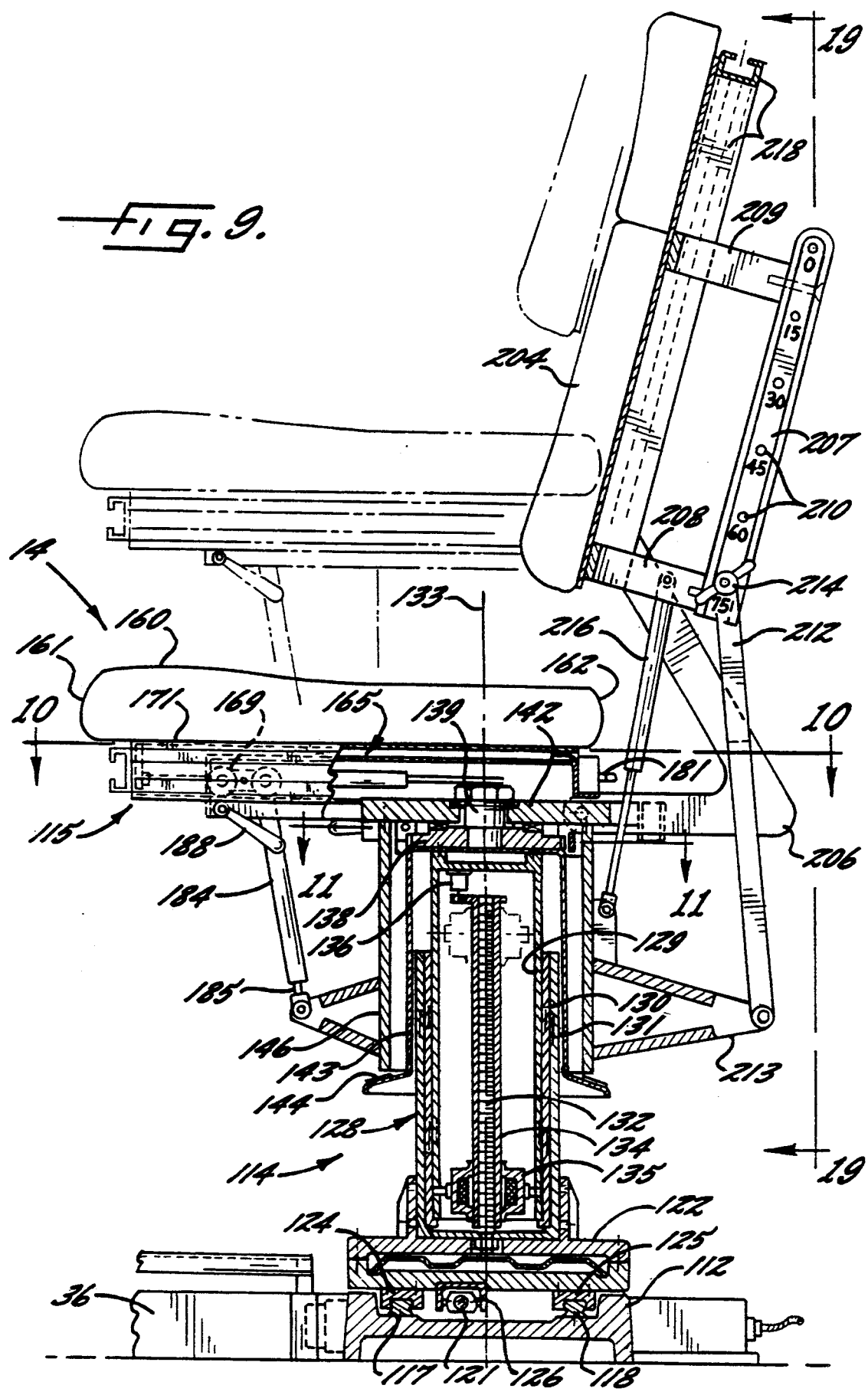
FIG. 9 is a sectioned side elevation view of the seat assembly and taken substantially along the line 9—9 of FIG. 2.
Figure 10:
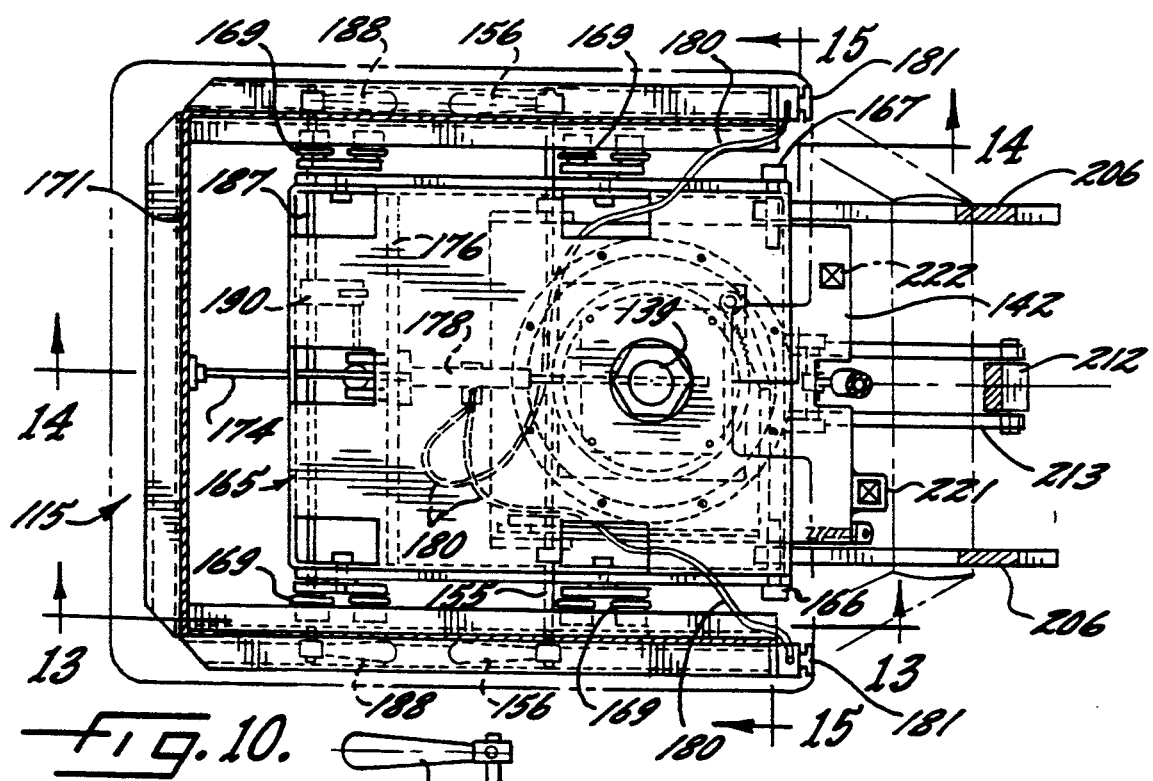
FIG. 10 is a sectioned top plan view of the seat assembly taken substantially along the line 10—10 of FIG. 9.

The seat assembly also comprises a back rest 204, which is mounted to the mounting plate 142 for pivotal movement about the transverse horizontal axis 163 defined by the pins 166, 167, which as noted above is perpendicular to the horizontal direction of sliding movement of the seat primary frame 171 with respect to the mounting plate 142. Thus, the back rest 204 may be pivoted between an upright position substantially perpendicular to the seat portion (FIG. 9) and a lowered position substantially co-planar with the seat portion (FIG. 20).

The mounting structure for the back rest includes a pair of L-shaped brackets 206, with the forward end of each bracket being pivotally connected to the mounting plate 142 by the pins 166, 167 for rotation about the transverse horizontal axis 163. The opposite end of each bracket 206 is fixed to the frame of the back rest 204. A position control bar 207 is mounted to the frame of the back rest by means of a pair of parallel mounting bars 208, 209, and so as to extend along the back side of the back rest. The position control bar 207 includes a plurality of spaced apart apertures 210. A linkage 212 is also provided which has one end pivotally connected to a bracket 213 which is fixed to the outer sleeve 146, and the opposite end of the linkage 212 mounts a pin 214 for releasable connection in a selected one of the apertures 210 of the control bar 207. By this arrangement, the back rest 204 may be tilted rearwardly and locked in about 15° increments between the upright and lowered positions. Also, a gas spring 216 is provided which is connected between a bracket on the outer sleeve 146 and one of the mounting bars 208 for the control bar 207. The gas spring 216 acts to bias the back rest toward its upright position, so as to facilitate the lifting thereof from its lowered position and also preclude rapid falling thereof in the opposite direction.

An outwardly open C-shaped car track 218 is fixed to each side of the frame of the back rest, and the car tracks 218 are adapted to receive one or more car assemblies 193 as described above and which are adapted to mount patient engaging pads to the back rest.

With the seat portion 160 in its forward position and with the back rest 204 in its fully lowered position as seen in FIG. 20, it will be noted that there is an open gap of significant length in the mid-portion of the seat assembly. To close this gap, and thus provide increased comfort to a patient lying upon the assembly, there is provided an intermediate pad 220 which can be removably mounted in the gap. For this purpose, the mounting plate 142 mounts a vertically open rectangular sleeve 221 at its rear edge, and an abutment 222 (FIG.

10) is fixed to the rear edge at a location laterally spaced from the sleeve 221. The intermediate pad 220 includes a depending rectangular post 224 extending from its bottom side which is adapted to be received in the sleeve 221, and a second post 225 which is adapted to engage the abutment 222. Thus, as will be apparent from FIG. 20, the intermediate pad 220 may be vertically dropped into its operative position, and later lifted therefrom.

As noted above, and as best seen in FIG. 20, the rotational position of the seat assembly 115 with respect to the vertical axis 133 may be visually determined from the pointer 147 on the outer sleeve 146 and the scale on the collar 144. The forward and rearward positions of the seat portion 160 may be determined from the scale 227 on the mounting plate and the associated pointer 228 mounted on the seat primary frame, and the angular tilted position of the seat portion may be determined 229 from the scale which is fixed to the seat subframe 165 and the pointer 230 which is fixed to the mounting plate 142. Thus, the various positions of these components for a particular exercising routine can be readily observed and recorded, so as to facilitate the later set-up of the apparatus when the same exercising routine is to be repeated for the same patient.

Description Of Representative Positions

FIGS. 22–25 are presented for the purpose of illustrating the flexibility of the positioning of the apparatus of the present invention, which in turn permits a wide variety of exercising modes. In this regard, and as noted above, it is important that the apparatus have sufficient flexibility in its positioning capability to permit the rotational axis 30 of the output shaft 29 of the rotary actuator 26 to be aligned with the joint which is being exercised or evaluated in a particular mode of operation.

Figure 22:
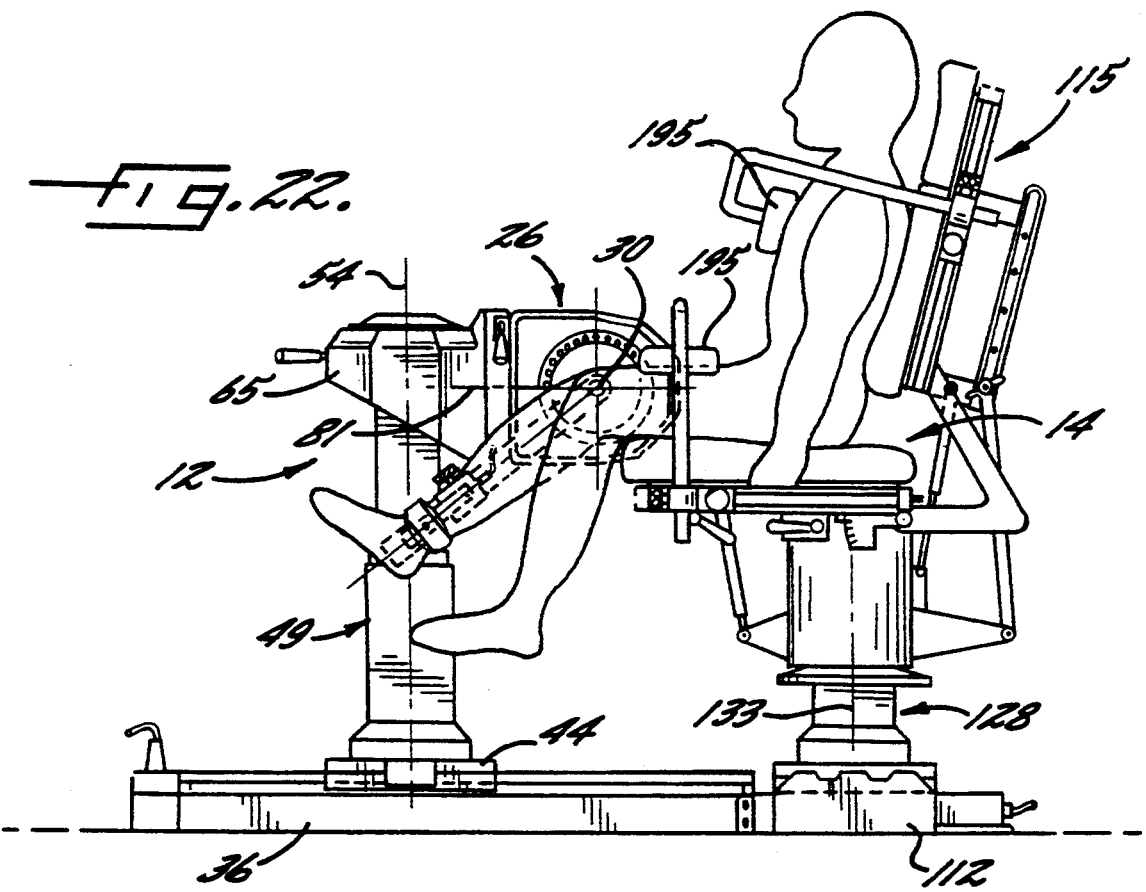
FIGS. 22 and 23 are side and front elevation views respectively of the apparatus of the present invention and positioned for performing an exercising routine for the right leg of a patient seated on the seat assembly.
Figure 23:
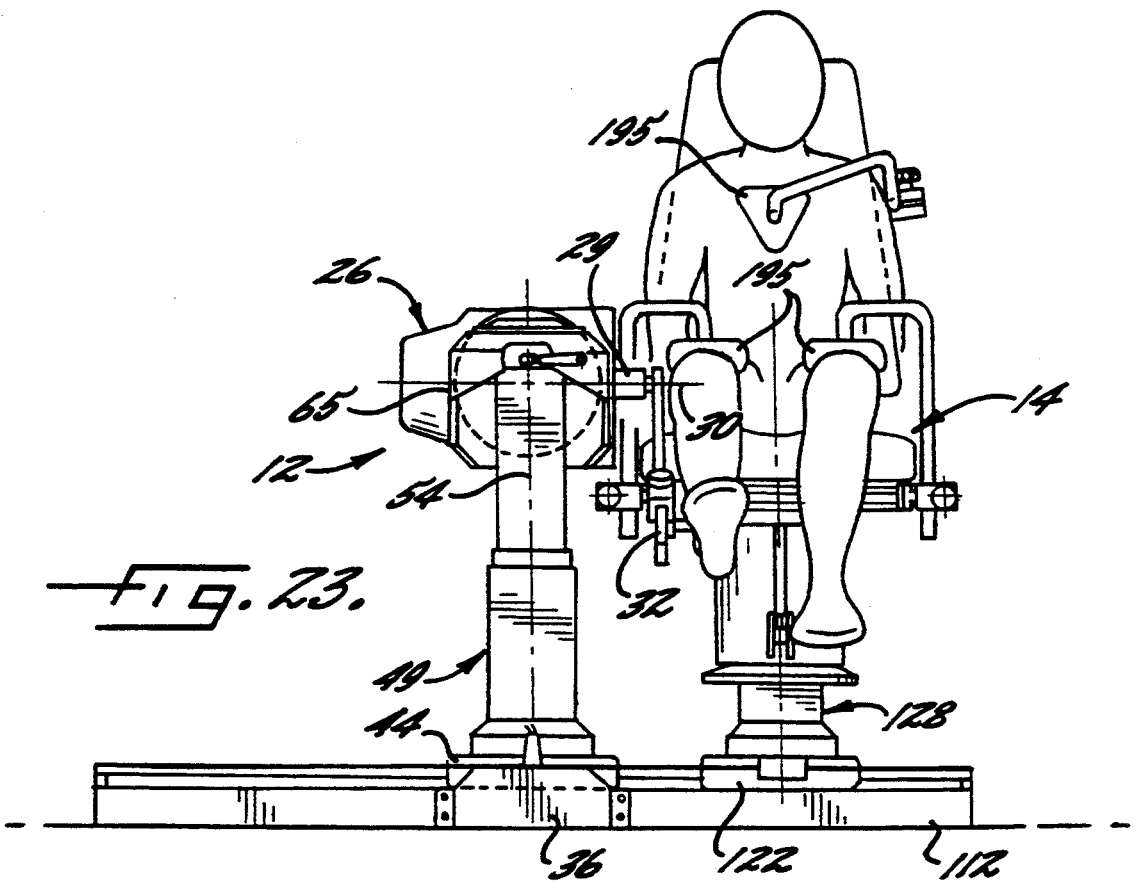
Figure 24:
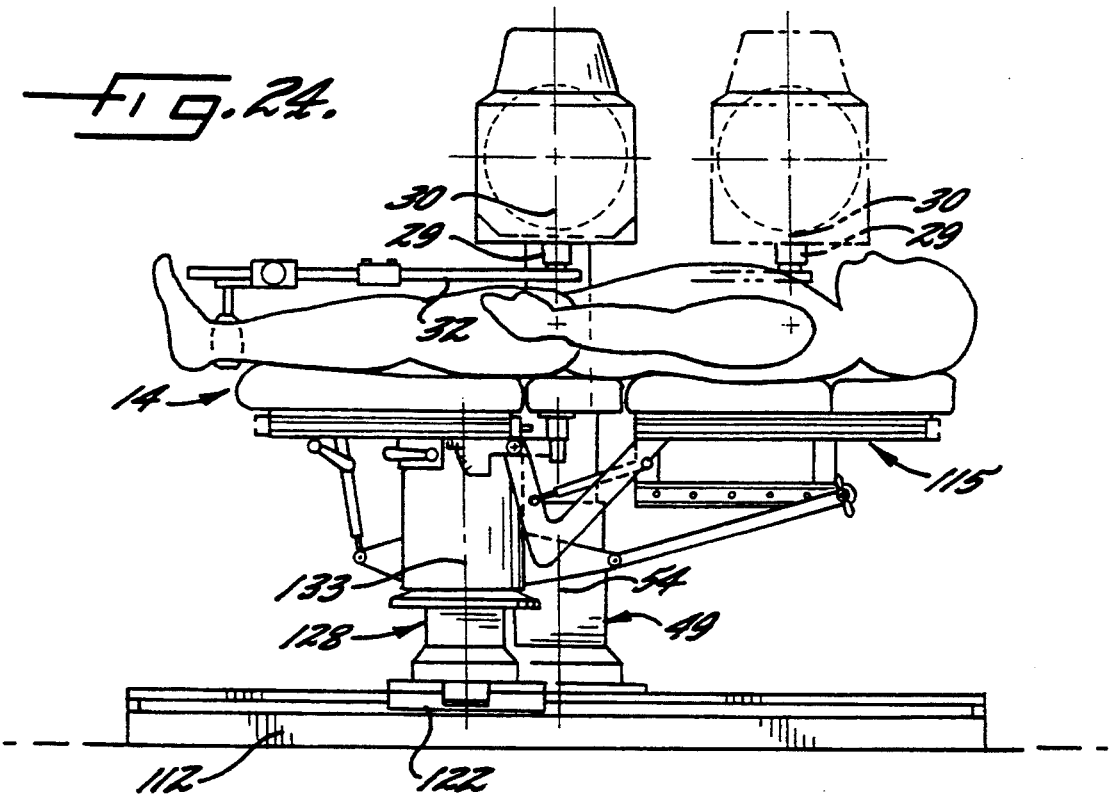
FIG. 24 is a side elevation view of the apparatus configured for performing a gravity eliminated exercise for the right hip of a patient, and further illustrating the position of the actuator in dashed lines when set-up to perform a gravity eliminated exercise for the right shoulder of a patient.
Figure 25:
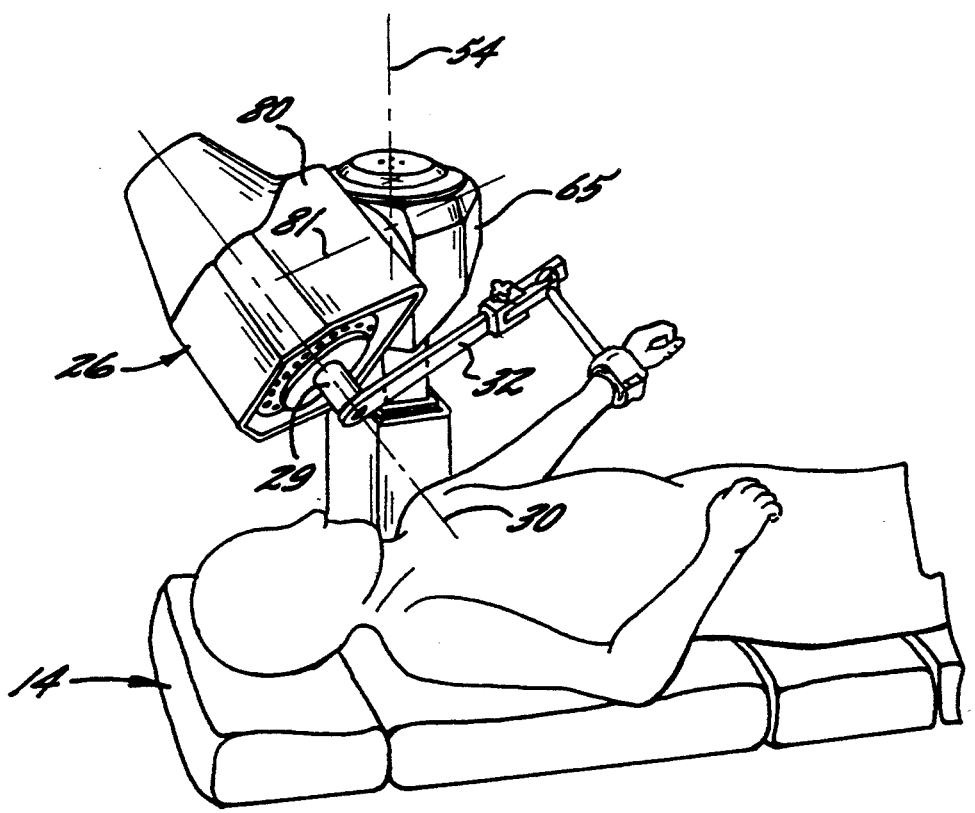
FIG. 25 is a perspective view illustrating the apparatus configured for performing an exercising routine on the left shoulder of a patient.

FIGS. 22 and 23 illustrate the apparatus configured so as to subject the right knee of the patient to flexion—extension, and with the rotational axis 30 of the rotary actuator 26 being aligned horizontally so as to pass through the joint of the right knee. FIG. 24 illustrates a gravity eliminated exercise, wherein the right hip of a patient lying upon the seat assembly 115 may be subjected to flexion—extension in a horizontal direction, and wherein the rotational axis 30 is directed vertically through the hip joint. FIG. 24 also illustrates, in dashed lines, the position of the actuator 26 for performing a gravity eliminated exercise on the right shoulder of the patient. FIG. 25 illustrates a PNF exercise, wherein the patient lies on his or her back, and the patient's arm moves between a down position at the side of the patient to an up and across position on the opposite side. As illustrated, the actuator 26 is oriented so that the rotational axis 30 is aligned with the left shoulder joint of the patient.

PATIENT POSITIONING SYSTEM

Overview: Patient Positioning System

Figure 3:
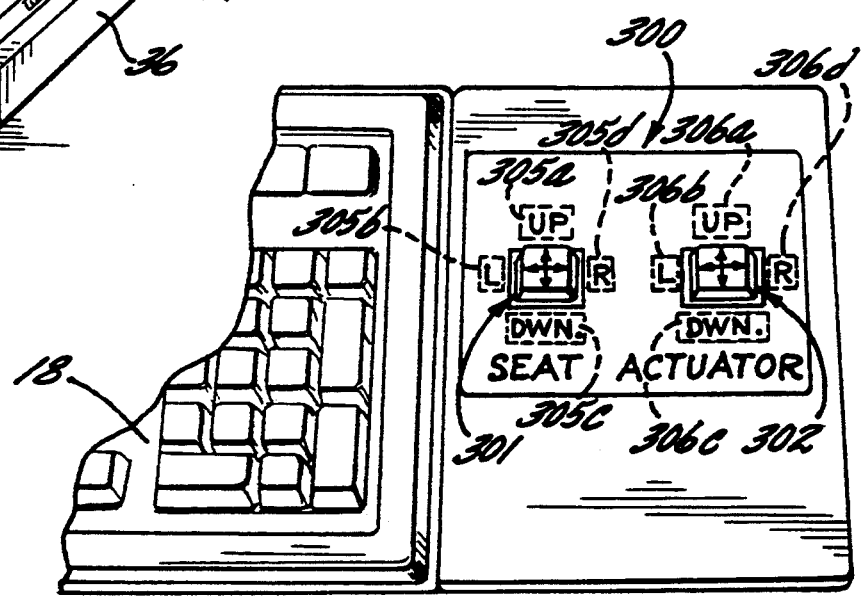
FIG. 3 is a fragmentary view of the keyboard of the apparatus taken substantially along the line 3—3 of FIG. 2, and illustrating the control switches associated with the patient positioning system of the present invention.

The patient positioning system is generally illustrated in the combination of FIGS. 1 and 3. The computerized control according to the present invention permits the automatic adjustment of the patient position for a computer controlled exercise machine, i.e. the relative positions of the seat and the actuator, sometimes referred to as "head" or "dynamometer". The patient positioning system may be manually operated, or it may be automatically operated in either standard mode or custom mode with the assistance of computer controller 15.

The patient positioning system comprises the seat and the actuator, and their respective motors and potentiometers for controlling the movement of the seat and the actuator, and the computer controller 15 including a monitor 16 with a display screen 16a and the attached keyboard 18 and patient control switches, generally identified at 300, located adjacent the keyboard (see FIG. 3).

Figure 26:
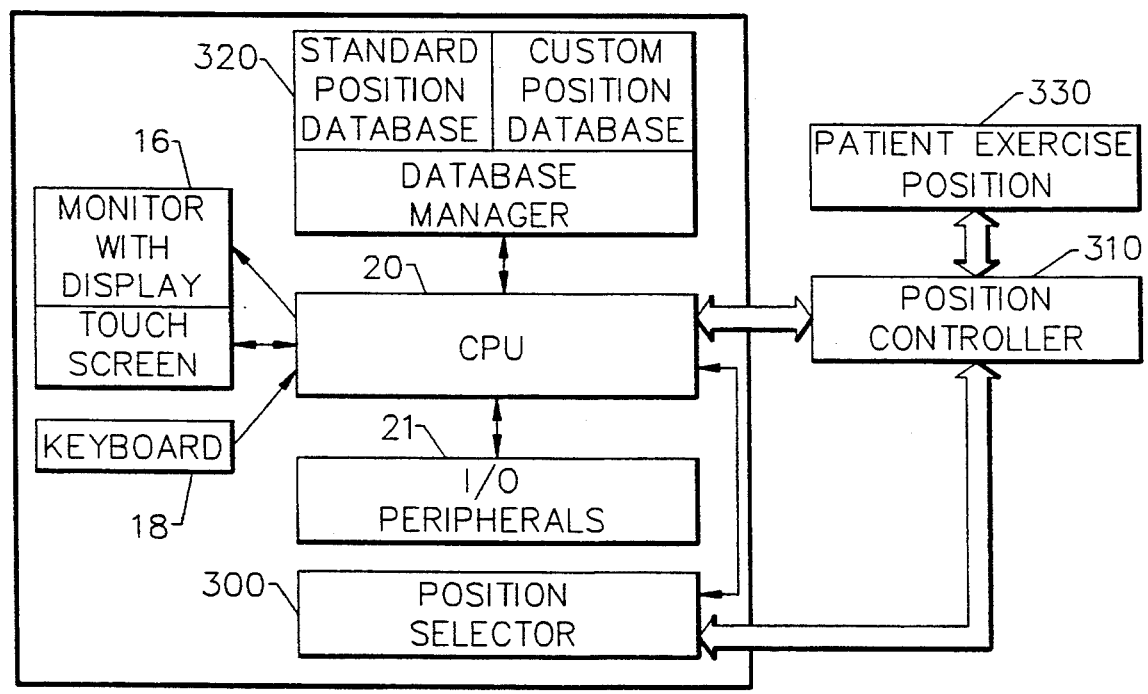
FIG. 26 is a schematic block diagram of the computer hardware used in FIGS. 1-4 and 8.

Referring to FIG. 26, a hardware block diagram for the computer controlled exercise machine having a patient positioning system will now be described. The computer controller 15 consists of central processing unit (CPU) or microprocessor 20, input/output (I/O) peripherals 21 such as floppy and hard disk drives, database manager 320, and user interfaces including monitor 16 with a display containing a touch screen interface, keyboard 18 and position selector or patient position switches 300. The database manager is typically a stored program which runs on CPU 20. The central processing unit 20 communicates with an actuator, illustrated as part of patient exercise position 330, which in turn controls the muscle exercise element (not shown). Central processing unit 20 also communicates with a position controller 310 which in turn controls the patient exercise position 330, i.e. relative actuator and seat position, in response to selection of the patient position at 300.

Referring to FIG. 3, the patient control switches 300, located adjacent the keyboard, are illustrated. These switches include two four-way switches, one 301 for the seat and the second 302 for the actuator. Each patient control switch is a four-way switch which can be manipulated to cause the electric motor to move the seat (or actuator) in a left or right direction (forward or backward) or up or down direction. Thus, the seat switch 301 has four contacts, for selectively (1) operating a first motor to move the seat up, (2) operating the first motor to move the seat down (3) operating a second motor to move the seat toward the left, and (4) operating the second motor to move the seat toward the right. Similarly, the actuator switch 302 also has four contacts, for selectively (1) operating a third motor to move the actuator up, (2) operating the third motor to move the actuator down, (3) operating a fourth motor to move the actuator in the forward direction, and (4) operating the fourth motor to move the actuator in the backward direction.

The patient control switches 300 (seat switch 301 and actuator switch 302) also include a display or direction indicator 305 and 306, respectively, for indicating the direction in which each switch should be moved thereby directing or prompting the operator to move the seat or actuator switch in a specified direction. As a result, computer controller 15 prompts the operator based on exercise positions stored in memory to properly actuate the two switches to facilitate the positioning of the seat and actuator in accordance with exercise positions previously stored in the memory of the computer relating to the particular exercise and the particular patient. The direction indicators 305 and 306, as schematically illustrated in FIG. 3, consist of a single light emitting diode (LED) associated with each direction in which the seat or actuator switch can be manipulated.

Once the positions are established for the particular exercise and the particular patient, the operator then manually adjusts the rotational positions of the first and second housing members, the rotational position of the seat, the forward and back position of the seat portion, the tilting of the seat, and the position of the back rest, to complete the set-up of the apparatus.

During use, the computer, based upon the current position of the seat and the actuator as determined by the potentiometers, will illuminate the appropriate LED 305a, 305b, 305c, or 305d associated with the seat switch 301 and LED 306a, 306b, 306c, or 306d associated with the actuator switch 302, and instruct the operator on the display screen 16 to move the patient control switch 301 or 302 in the direction corresponding to the illuminated LED, and allow the patient control switches to be active only in the direction indicated by the LED and on the display screen, thereby prompting the user to move the seat and actuator to a certain exercise position.

Modes of Operation: Patient Positioning System

The patient positioning system has three modes of operation, namely, a manual mode, a standard mode, and a custom mode. The patient positioning system for the exercise machine according to the present invention is always capable of being operated in the manual mode. Thus, the seat and actuator can always be moved manually to desired exercise positions by pressing the seat and actuator switches in the desired direction. The standard and custom modes of operation for the patient positioning system are selected by the user via the display screen and the patient positioning system instructs the user through the necessary steps to adjust the position of the seat and actuator to the standard or custom position. The interface between the patient positioning system and the user is implemented using the simplified data access described in U.S. Pat. No. 5,054,774 to Belsito.

In the standard mode, the relative seat and actuator positions are default positions retrieved from the standard patient position database and displayed on the display screen to permit selection by the clinician or user. The relative standard seat and actuator positions stored in the standard patient position database within the computer are based upon the particular exercise or evaluation to be performed, the joint upon which the particular exercise or evaluation is to be performed, the movement pattern, the side of the patient to be exercised or evaluated, as well as other variables. Once the exercise or evaluation, and the joint, movement pattern and side have been selected by the user, the relative seat and actuator positions are retrieved from the standard patient position database. The patient positioning system then determines which of the seat (left/right, up/down) and actuator (forward/backward, up/down) positions need to be adjusted based on current readings from the potentiometers for the seat and actuator and the relative seat and actuator positions retrieved from the standard patient position database. The patient positioning system then proceeds to prompt the user as to the direction to move the seat and/or actuator by both illuminating the appropriate LED, and displaying instructions on the display screen for moving the seat and actuator based on the relative standard patient seat and actuator position. In addition, the patient control switches are controlled such that they can be activated only in the direction indicated by the lighted LED. Thus, if the patient position switches are pressed in any direction other than that associated with the lighted LED, there will be no movement of the seat or actuator.

Once the correct patient position switch (seat or actuator) is pressed or toggled in the direction indicated by the lighted LED and by the instructions on the display screen, the seat or actuator is moved in the direction corresponding to that in which the switch is pressed. The seat or actuator will continue to move in the indicated direction while the switch is pressed or toggled, and the seat or actuator has not reached the standard position setting for that direction (forward/backward, left/right or up/down). Once the destination is reached, the LED will no longer be illuminated and the seat (or actuator) will discontinue moving even if the user continues to press the switch. The patient positioning system will then proceed to adjust the seat or actuator in the other directions until the seat and actuator have been fully adjusted to the standard patient position setting.

In a preferred embodiment, the actuator is first adjusted to its furthest forward position in order to move the actuator out of the way prior to beginning adjustment of the relative positions of the actuator and seat for a patient. Then, the actuator is moved in the up/down direction, the seat is adjusted in the left/right direction followed by the up/down direction, and finally, the actuator is moved backward towards the seat. It should be understood that the order of adjustment of the relative positions of the actuator and seat can vary.

In operation, once the computer causes the LED associated with a particular direction for one of the patient control switches to illuminate thus directing the user to move the seat or the actuator in the direction as indicated by the LED, the computer deactivates all other connections associated with the other directions for the patient control switches. Thus, the user can only move the actuator or seat in the direction indicated by the LED. If the user attempts to move the actuator or seat in a direction other than that which is indicated by the illuminated LED, and on the display screen, the actuator or seat will not move since the computer has deactivated the patient control switches in all directions except that indicated by the illuminated LED and on the display screen. Once the user, as instructed by the computer, has proceeded through the sequence of moving the actuator in the forward/backward direction and the up/down direction, and the seat in the left/right direction and the up/down direction, the new position for the actuator and seat may be saved in the custom patient position database. At any time after completion of the relative standard patient positioning process, the relative position of the actuator and seat may be further adjusted using the manual mode by manipulating the patient position control switches.

In the custom patient positioning mode, the user selects the patient name, joint, movement pattern, and side to be exercised or evaluated. The computer system then retrieves the relative custom actuator and seat patient positions for that particular patient, joint, movement pattern and side from the custom patient position database and determines the directions, using the potentiometers associated with the actuator and the actuator base member, and the seat and the seat base member, in which the actuator and seat need to be moved. The patient positioning system then proceeds, similar to that for standard mode, to instruct the user to move the actuator and seat to the positions retrieved from the custom patient position database by determining the first direction in which the actuator and/or seat needs to be moved, deactivating the patient control switches in all other directions, lighting the appropriate LED and displaying corresponding instructions on the display screen, and moving the actuator and/or seat in the direction corresponding to that indicated by the illuminated LED while the user presses the patient control switch in that direction.

The LED will stay illuminated and the display will continue to instruct the user to move the actuator or seat in a particular direction until the position for that direction is reached. Once the position for that direction is reached, the actuator or seat will not move even if the user continues to press the patient control switch in that particular direction. The patient positioning system then continues the positioning of the actuator and seat to the relative custom position by instructing the user to move the actuator or seat in another direction, and the process continues as previously described. Once the sequence of moving the actuator and seat has been completed, the relative positions of the actuator and seat can be further adjusted by entering the manual mode by either selecting the manual mode via the display and then manipulating the patient position control switches in the desired directions, or by simply manipulating the patient position control switches in the desired directions. Once the desired relative actuator and seat positions have been obtained, the positions may be saved in the custom patient position database for the particular patient.

Thus, the patient positioning system according to the present invention permits the optimum relative actuator and seat position settings without the need to read or even remember the desired settings.

Detailed Operation: Patient Positioning System

The sequence of operations performed to control the patient positioning system in the manual mode, standard mode, and custom mode will now be described in detail with reference to the operational control flowcharts of FIG. 27 and the sample display screens of FIG. 28. The flowcharts in FIG. 27 provide the flow control resulting from the user selection of various parameters and manipulation of the patient position switches. It will be understood by those having skill in the art that the flowcharts may be implemented by a computer, operating under stored program control.

The displays illustrated in FIG. 28 are examples of displays which appear on the display screen 16a of monitor 16 at various times during the operator controlled selection process. The displays are in the form of a touch screen. The touch screen, the keyboard, and the patient position switches, separately and collectively, comprise the input device to the system or computer controller. The patient positioning system utilizes simplified data access, which includes the input device, described in U.S. Pat. No. 5,054,774 to Belsito.

Figure 27A:
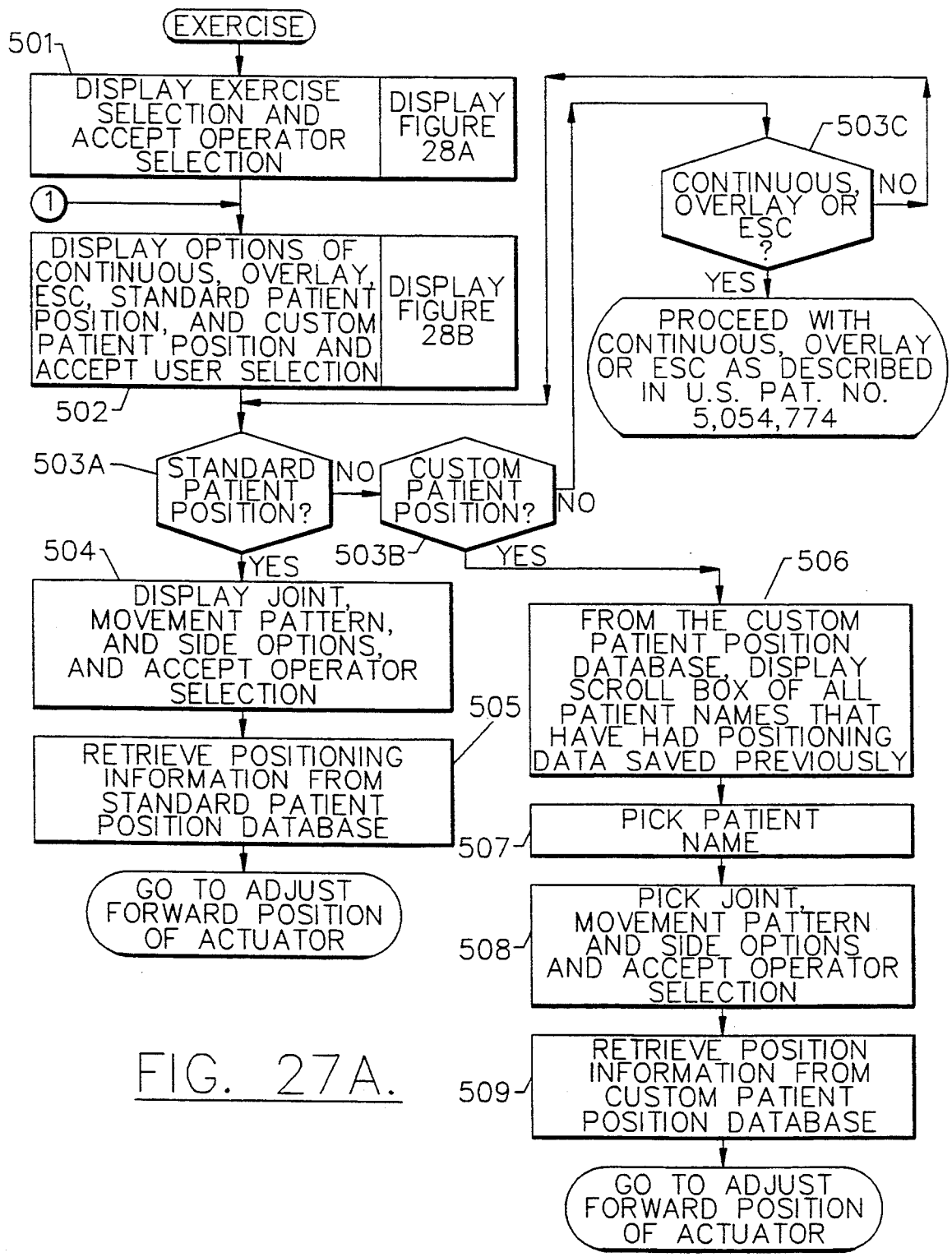
FIGS. 27A-27K are flowcharts illustrating operations for controlling the automatic positioning of the seat and actuator according to the present invention.
Figure 28A:
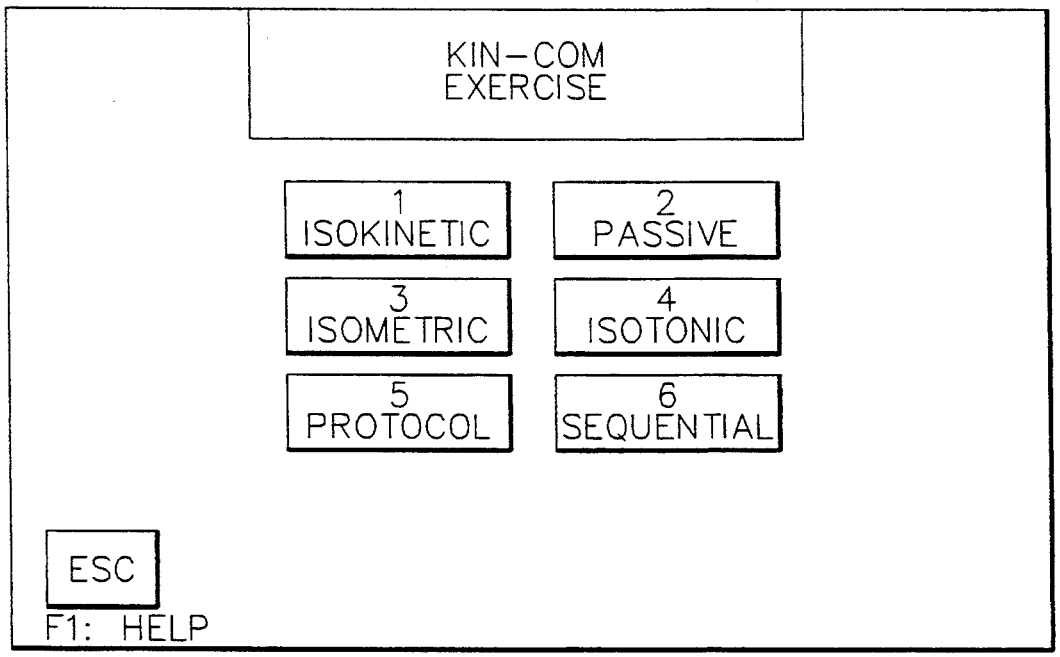
FIGS. 28A-28U illustrate display screens which are presented to a clinician or operator when controlling the automatic positioning of the seat and actuator of the muscle exercise machine according to FIGS. 27A-27K.
Figure 28B:
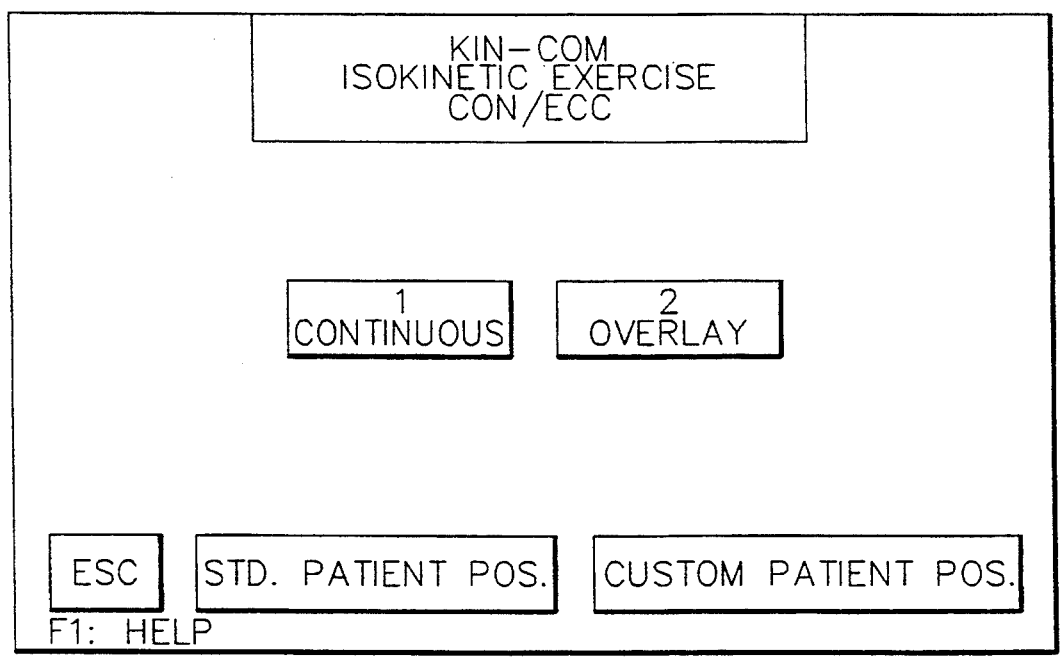

The patient positioning system according to the present invention can be implemented while the exercise machine is in either exercise or evaluation mode. Referring to FIG. 27A, implementation of the patient positioning system while in exercise mode will now be described. While in exercise mode, the user may select one of the exercise options displayed at 501 on display screen 16a, as illustrated in FIG. 28A. Thereafter, the options of CONTINUOUS, OVERLAY, STANDARD PATIENT POSITIONING, and CUSTOM PATIENT POSITIONING as illustrated in FIG. 28B are displayed on display screen 16a at 502, and the operator's selection of one of the options is accepted. A determination is made at 503 as to which option the operator selected. Based on a determination at 503c that the CONTINUOUS, OVERLAY or ESCape option was selected, control of the exercise machine continues as described in U.S. Pat. No. 4,711,450 to McArthur and U.S. Pat. No. 5,054,774 to Belsito. If it is determined at 503a that STANDARD PATIENT POSITIONING was selected or at 503b that CUSTOM PATIENT POSITIONING was selected, processing will continue as described below. In the event no option was selected, the patient positioning system will continue to wait until one of the options displayed in FIG. 28B is selected.

The present invention permanently stores standard position settings for the actuator and the seat based upon the joint, movement pattern, and side to be exercised or evaluated in the standard patient position database. These settings include not only forward/backward, up/down, and left/right, but also tilt, rotation, back angle, bottom, bottom angle, start and stop locations as well as stabilization. If it is determined at 503a that STANDARD PATIENT POSITION was selected, the patient positioning system will display the joint, movement pattern, and side options for the exercise to be performed are displayed at 504. The patient positioning system then proceeds at 505 to retrieve the standard patient position settings from the standard patient position database for the selected joint, movement pattern and side options.

If it is determined at 503b that CUSTOM PATIENT POSITIONING was selected, all patient names having positioning data stored with them are displayed on display screen 16a at 506. The user may then select a patient name at 507 from those displayed, and select a joint, movement pattern and side at 508. Custom patient data is then retrieved from the custom patient position database at 509 based on the selected patient, joint, movement pattern and side, and adjustment of the relative actuator and seat position continues as described below for standard patient positioning.

Figure 27B:
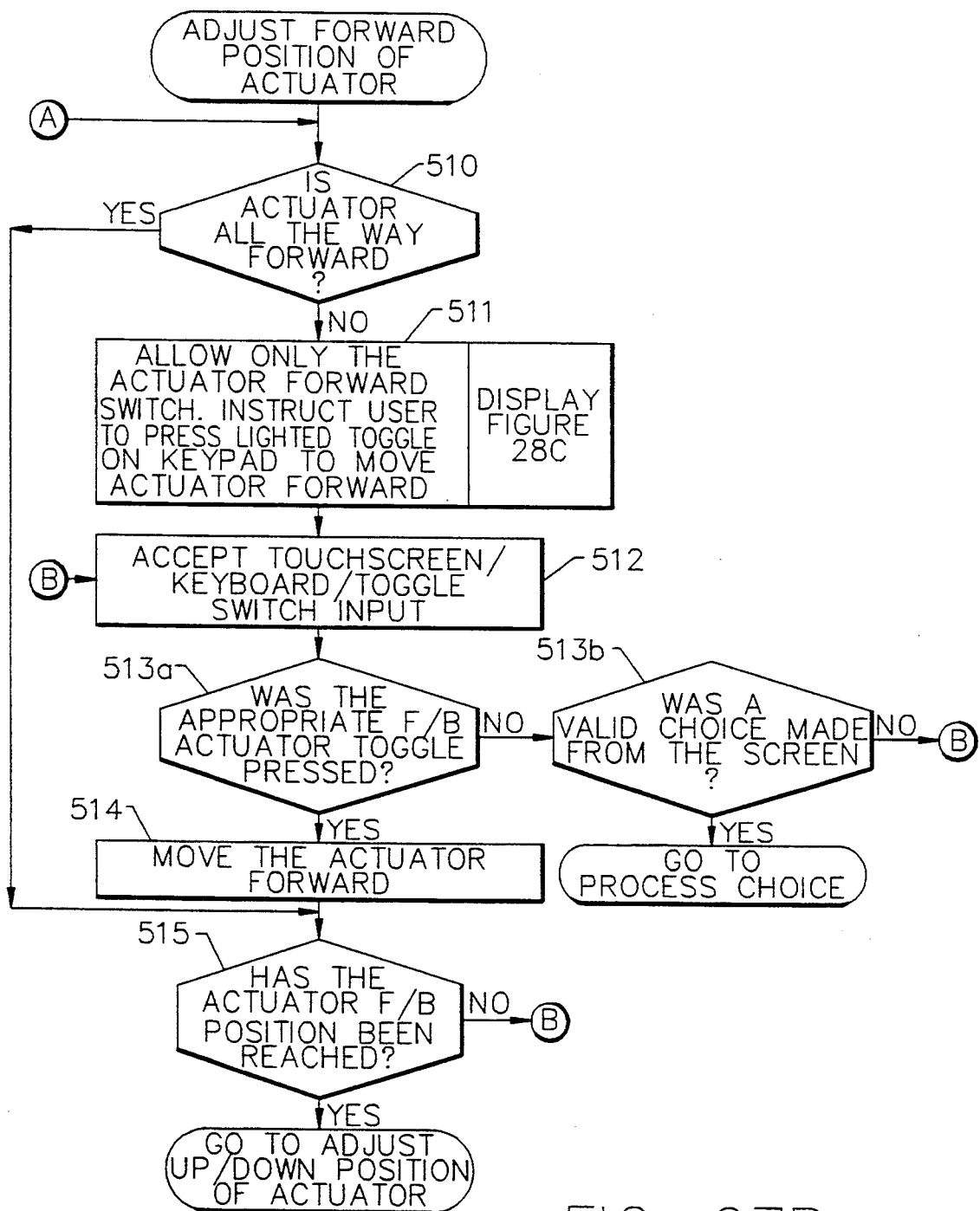
Figure 28C:
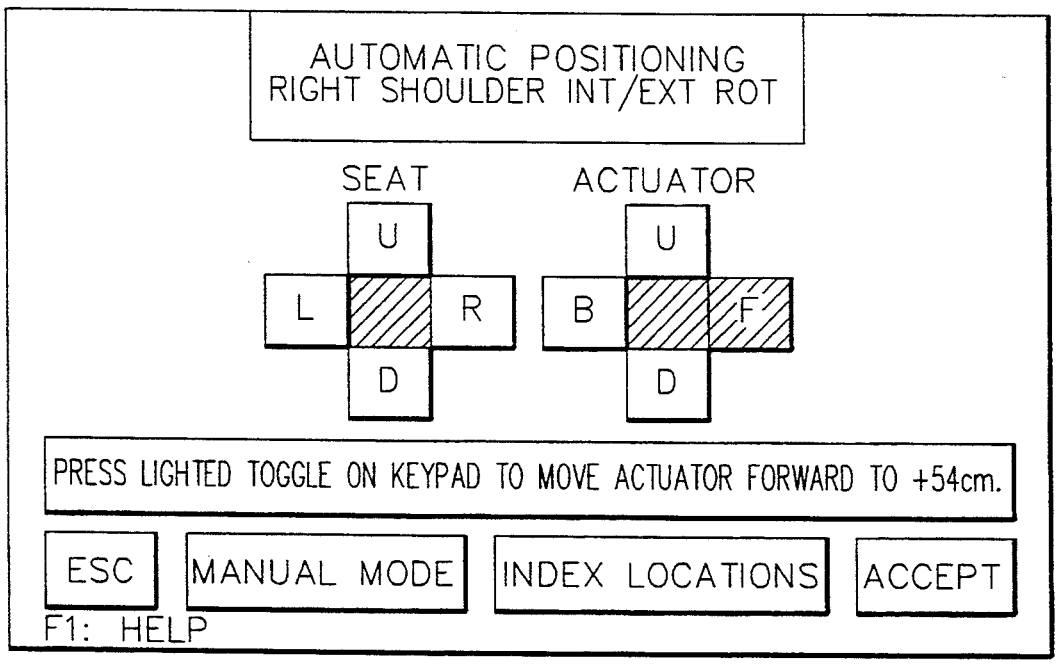

Referring to FIG. 27B, a determination is made at 510, based upon a comparison of the current position of the actuator and the standard or custom patient position settings retrieved from the standard or custom patient position database, as to whether the actuator is located in the farthest forward position. If the actuator is located in the farthest forward position, control is transferred to begin the process of moving the actuator up or down which will be described below. In the event that the actuator is not located in its farthest forward position, the patient positioning system, at 511, then controls the patient positioning switch for the actuator (302 at FIG. 3) as well as the motor for the actuator to allow only the actuator to be moved in the forward direction, prompts the user to move the actuator in the forward direction by illuminating the LED (306d at FIG. 3) associated with the forward direction for the actuator position switch and by displaying FIG. 28C thereby instructing the user to press the actuator patient position switch in the direction indicated by the lighted LED. The instructions on the display screen also indicate the direction in which the actuator is to be moved as illustrated in FIG. 28C by lighting the appropriate direction below the ACTUATOR label. As indicated in FIG. 28C, the user can switch to manual mode by touching the MANUAL MODE touch pad on the display screen or selecting INDEX LOCATIONS allowing manual entry of various index locations via keyboard 18 which will be described below.

At 512, the patient positioning system then waits until the user manipulates the actuator positioning switch (302 of FIG. 3) in the forward direction or selects one of the other options on the display screen as illustrated in FIG. 28C. Once the user has entered the selection or movement of the actuator positioning switch, a determination is made at 513 as to whether the appropriate actuator patient position switch was pressed, i.e. whether the actuator patient positioning switch was pressed in the forward direction, or whether a valid choice was made from the touch screen. If it is determined at 513a that the actuator patient positioning switch adjacent the illuminated LED (306d) was pressed in the forward direction, the patient positioning system proceeds at 514 to move the actuator in the forward direction. At the same time, the patient positioning system monitors the current position of the actuator with respect to the standard position for the actuator based upon the selected joint movement pattern, and side to determine whether or not the actuator has reached the farthest forward position. A determination is made at 515 as to whether the actuator has reached the farthest forward position. If the actuator has not reached the farthest forward position, control is transferred to transition Block B and the patient positioning system continues to accept the input from the actuator position switch or from the touch screen or keyboard at 512 and the process continues. If the actuator has reached its farthest forward position, the patient positioning system then proceeds to adjust the height of the actuator, the processing of which will be described below with respect to FIG. 27C.

If it is determined at 513a that the actuator position switch was not pressed in the forward direction, a determination is made at 513b to determine whether one of the options on the touch screen illustrated in FIG. 28C was selected. If none of the options was selected, the patient positioning system continues to wait until either the actuator position switch is activated by the user or one of the options appearing in FIG. 28C is selected. If one of the options in FIG. 28C is selected, the patient positioning system then transfers control to "Process Choice" which will be described below with respect to FIG. 27I.

Figure 27C:
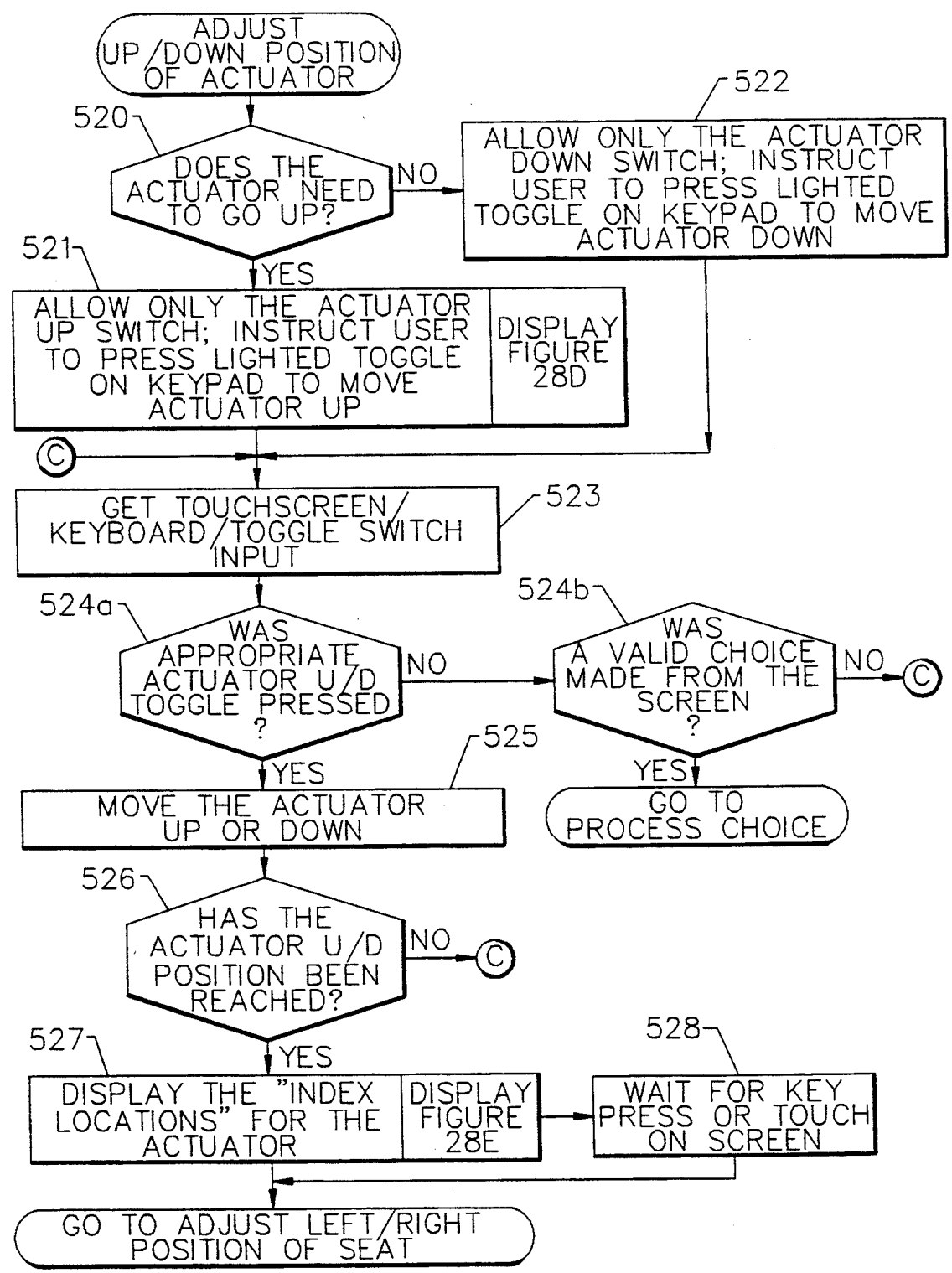

Referring to FIG. 27C, the process of moving the actuator in the up or down position will now be described. At the outset of adjusting the height of the actuator, the patient positioning system determines at 520, based upon the current vertical position of the actuator and the standard vertical position setting for the actuator, as to whether the actuator needs to be moved up. If it is determined that the actuator needs to be moved up, the patient positioning system at 521 controls the actuator position switch (302 of FIG. 3) and the motors for the actuator to allow the actuator to be moved in the up direction only, and instructs the user to move the actuator in the up direction by lighting the LED (306a of FIG. 3) on the keypad adjacent to the up position for the actuator position switch, and by displaying the screen illustrated in FIG. 28D on the display screen 16a instructing the user to move the actuator up to a specific centimeter value and illuminating the direction the actuator is to be moved under the ACTUATOR label on the display screen. If the patient positioning system determines at 520 that the actuator does not need to be moved up but rather needs to be moved down, the patient position system at 522 controls the actuator position switch and the motors for moving the actuator to allow the actuator only to be moved in the down direction, and instructs the user by displaying a screen similar to that illustrated in FIG. 28D to move the actuator in the down direction, illuminates the down direction under the ACTUATOR label on the display screen, and lights the LED (306c of FIG. 3) adjacent to the down direction on the actuator position switch.

Regardless as to whether the actuator is to be moved in the up or down direction, the patient positioning system then proceeds at 523 to accept the user's input at the actuator position switch in the up or down direction, accordingly, or one of the options provided on the touch screen including MANUAL MODE, INDEX LOCATIONS or ACCEPT.

After accepting the input, the patient position system determines at 524 whether the correct actuator position switch was activated, i.e. did the user press the actuator position switch in the up or down direction depending on the direction the patient positioning system determines that the actuator needs to be moved, or did the user select a valid option from the touch screen. If it is determined at 524a that the actuator position switch was pressed in the correct direction, the actuator is moved in the correct direction, either up or down, at 525. The computer continues to monitor the current position of the actuator using the location of the actuator determined by the potentiometers and compares that location with the standard or custom position settings for the actuator at 526. If it is determined that the actuator has reached its correct up or down position, the index locations for the actuator illustrated in FIG. 28E are displayed to the user at 527, and patient positioning continues by pressing anywhere on the touch screen at 528 and control is transferred to position the seat as will be described below. If it is determined at 526 that the actuator has not reached its correct up or down position, control is transferred to transition Block C so that the patient positioning system can continue at 523 to accept input at the actuator position switch in either the up or down direction or from the touch screen or keyboard.

Figure 27I:
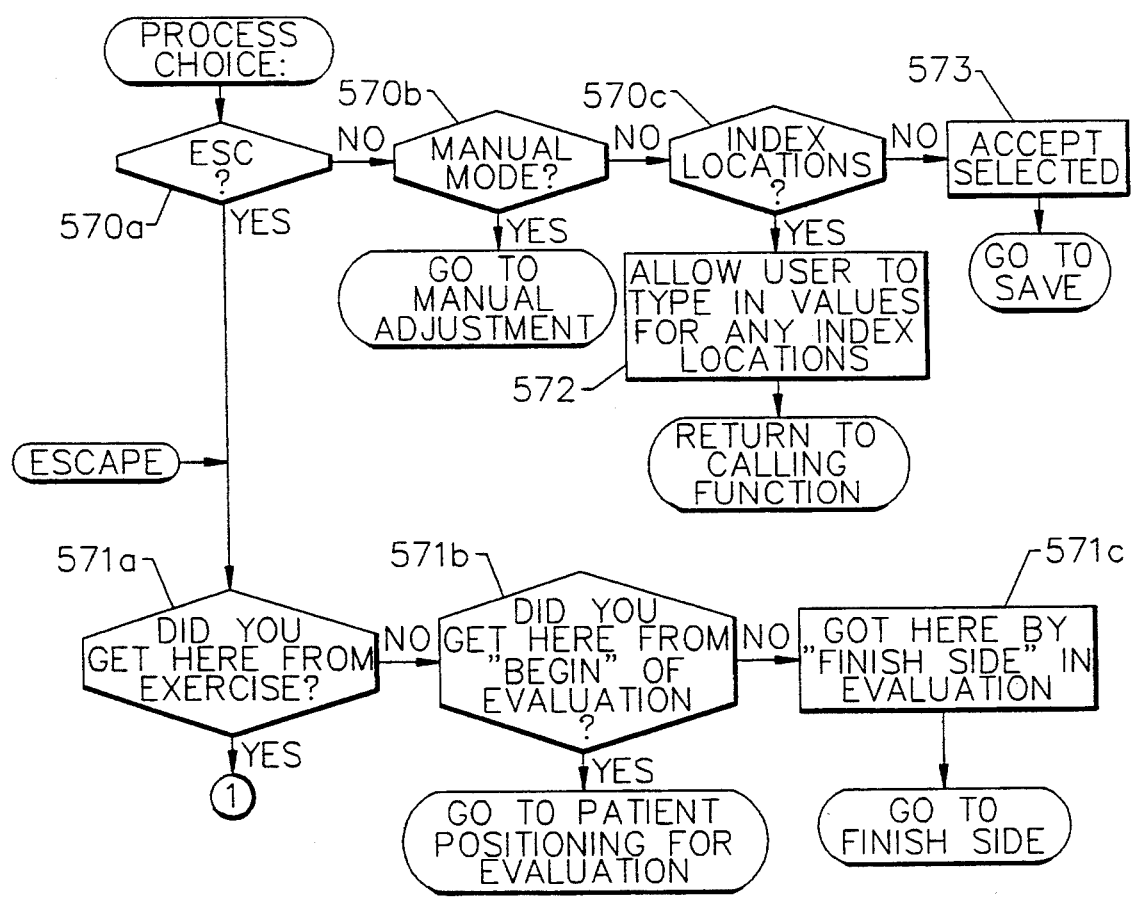
Figure 28D:
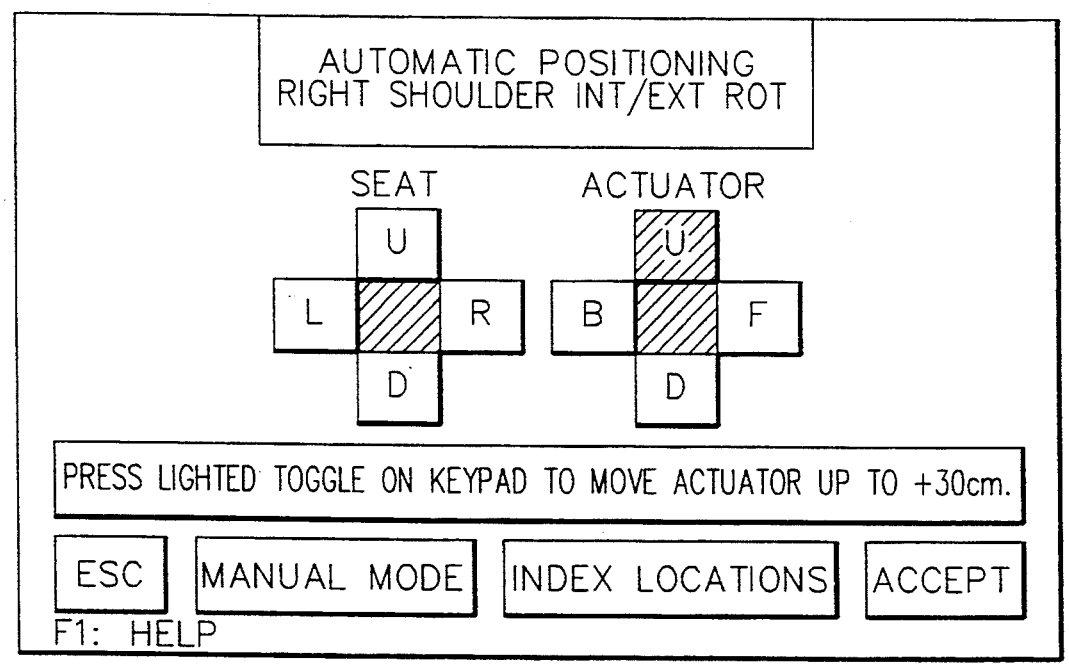
Figures 28E, 28F:
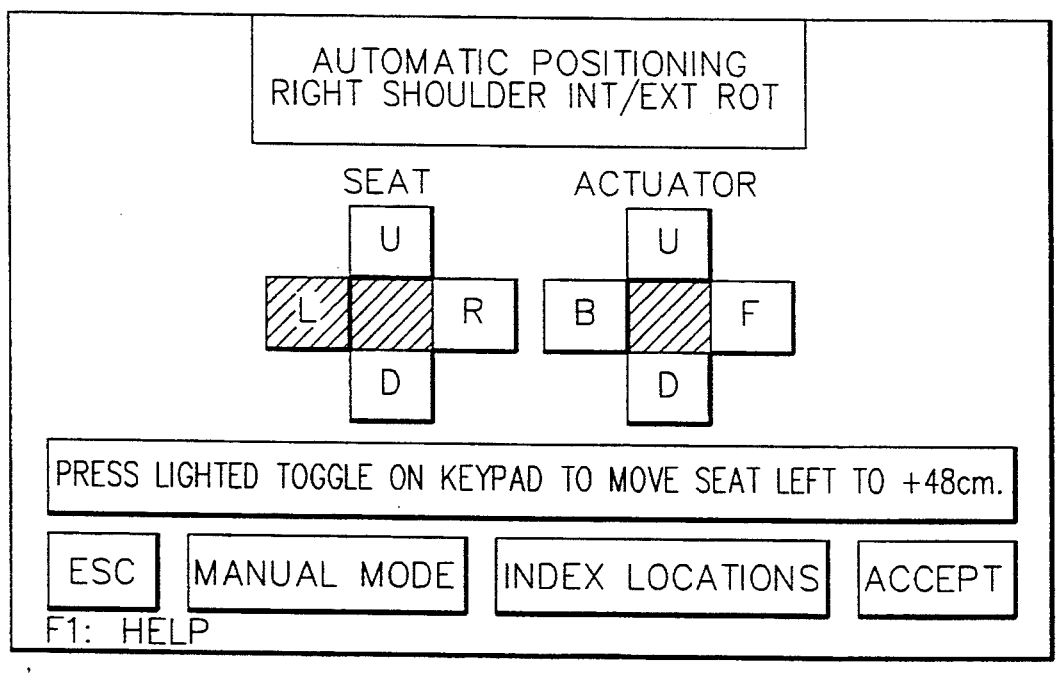

If it was determined at 524a that the correct actuator position switch or toggle was not pressed, a determination is made at 524b as to whether a valid option from those displayed on the screen as illustrated in FIG. 28D, i.e. ESCape, MANUAL MODE, INDEX LOCATIONS, or ACCEPT, was selected. If it is determined that one of these options was selected, the patient positioning system continues by processing this choice as will be discussed below with respect to FIG. 27I. If it is determined that a valid option was not selected from those displayed in FIG. 28D, the patient positioning system continues to wait for the user to select one of the options displayed in FIG. 28D or input the correct up or down direction at the actuator position switch.

Figure 27D:
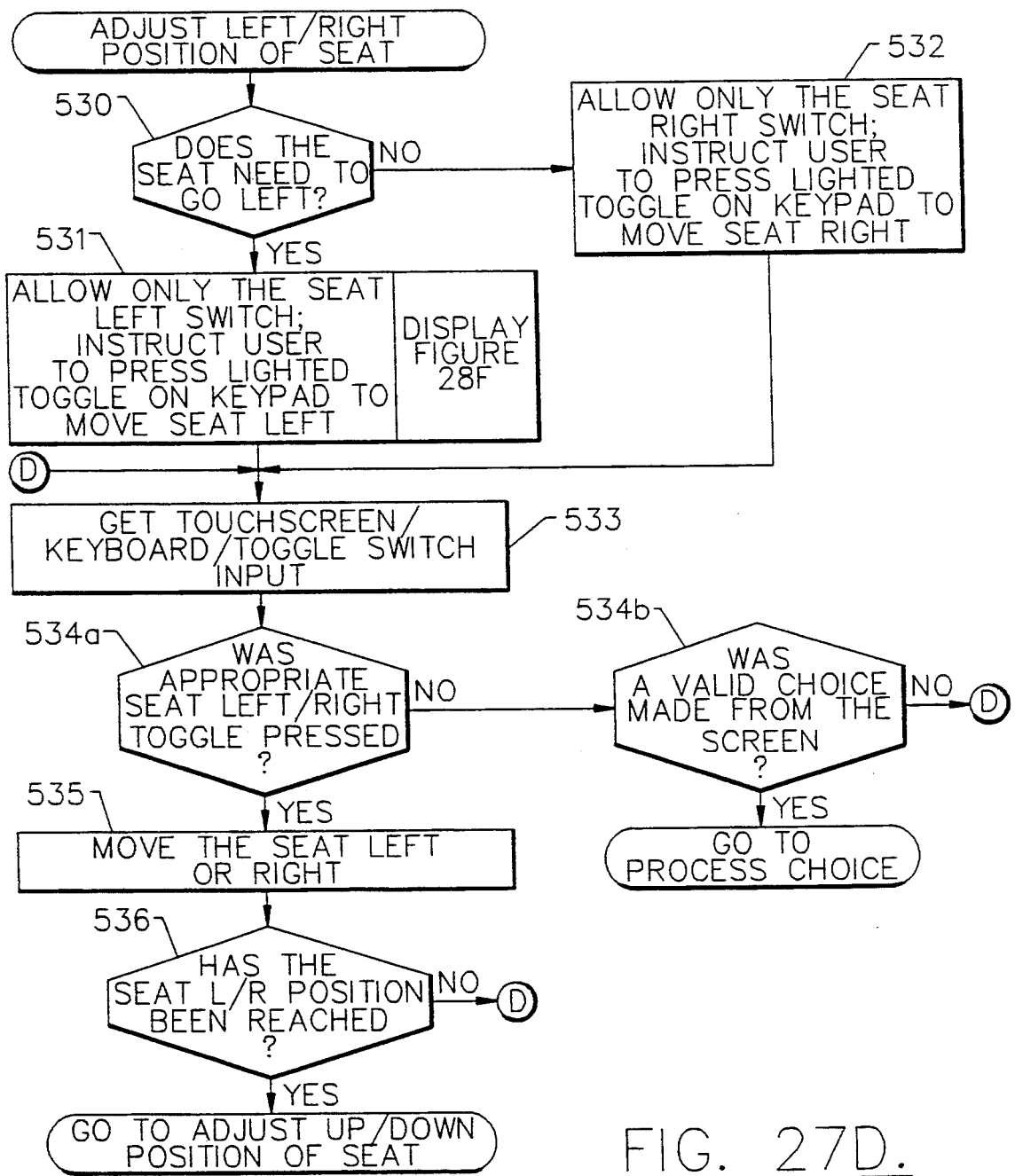

Referring to FIG. 27D, positioning of the seat will now be described. The patient positioning system begins adjusting the seat by determining at 530 whether the seat needs to be moved to the left. This determination is made based upon the present location of the seat and the seat position setting retrieved from the standard or custom patient position database. If it is determined at 530 that the seat needs to be moved to the left, the seat position switch (301 of FIG. 3) and the seat are controlled at 531 so that the seat can be moved only to the left by allowing the seat position switch to be active only in the left direction. In addition, the user is instructed at 531 to move the seat to the left to a specific centimeter value and the left direction under the SEAT label is illuminated as illustrated in FIG. 28F. The LED (305b of FIG. 3) adjacent to the left direction of the seat position switch is also illuminated at 531. If the seat does not need to be moved to the left based upon the standard or custom seat position settings, the seat position switch and the motors for moving the seat are controlled so that the seat can move only to the right and the seat position switch can be activated only in the right direction (Block 532). In addition, a screen similar to that in FIG. 28F is displayed on screen display 16a instructing the operator to move the seat to the right to a specific centimeter value, illuminating the right direction under the SEAT label, and illuminating the LED (305d of FIG. 3) adjacent to the right direction of the seat positioning switch.

Whether the user is instructed to move the seat to the left or to the right, input of the selected seat movement at the seat positioning switch or one of the other options displayed in the screen illustrated at FIG. 28F is accepted at 533. A determination is then made a 534, regardless as to whether the seat was to be moved to the left or to the right, as to whether the seat positioning switch was pressed in the correction direction, or whether one of the options displayed in FIG. 28F was selected. If it is determined at 534a that the seat positioning switch was pressed in the correct direction, the seat is then moved to the left or the right at 535 in accordance with the activation of the seat switch by the user. Thereafter, a determination is made at 536 as to whether the standard or custom seat position setting has been reached. If the standard or custom seat position setting has been reached, patient positioning will continue with adjusting the seat in the up or down direction as will be described below. If the standard or custom left/right seat position setting has not been reached, control is transferred to transition Block D so that input at the patient seat switch in the left or right direction or from one of the options located on the touch screen or on the keyboard will continue to be accepted at 533.

If it was determined at 534a that the seat position switch was not pressed or activated in the correct left or right direction as indicated by the lighted LED and the screen display as illustrated in FIG. 28F, a determination is made at 534b as to whether one of the other choices from the screen display, i.e. ESCape, MANUAL MODE, INDEX LOCATIONS, or ACCEPT, was selected. If one of these options was selected, the patient positioning system then proceeds to process the choice, the details of which will be described with respect to FIG. 27I. If none of these other valid options was selected, the patient positioning system continues at 533 to wait for the activation of the seat position switch in the correct direction or selection of one of the options from the touch screen illustrated in FIG. 28F.

Figure 27E:
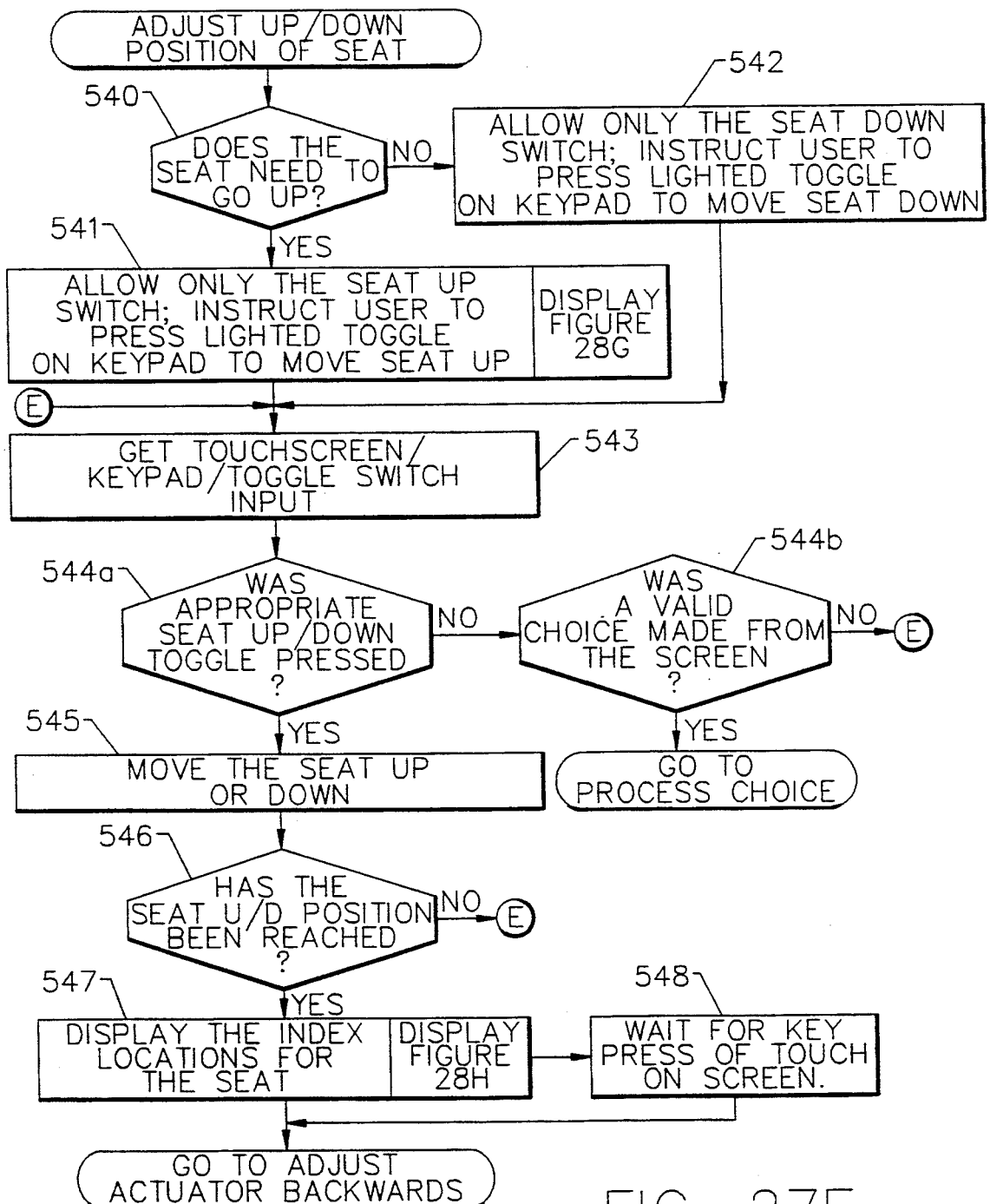
Figure 28G:
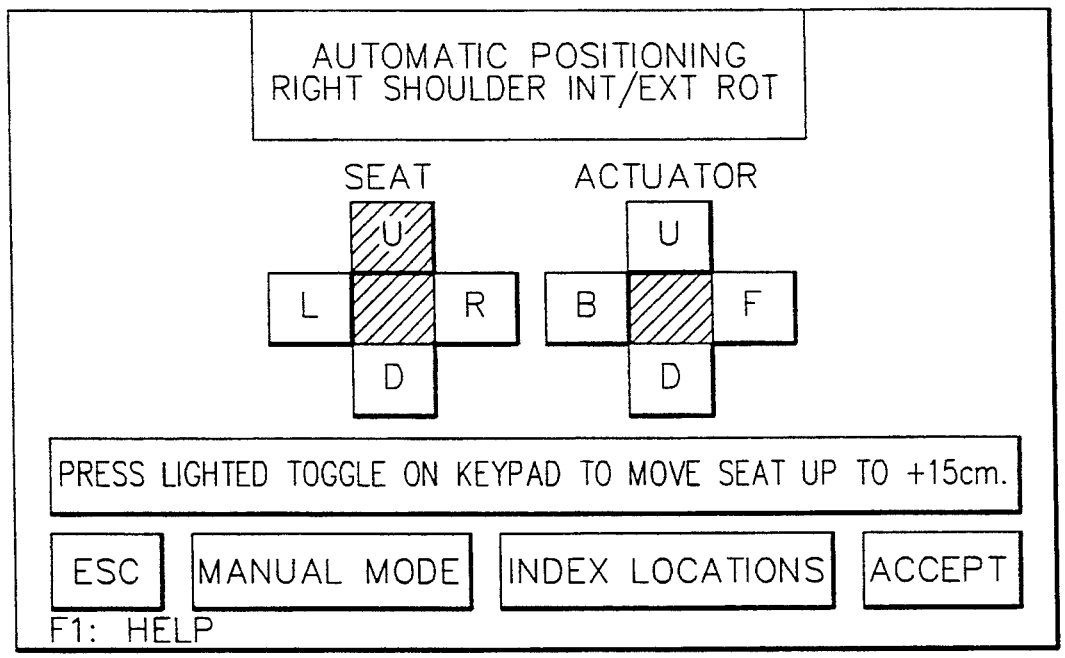

Referring to FIG. 27E, adjustment of the seat in the up/down direction will now be described. The patient positioning system begins adjusting the seat in the up/down direction by making a determination at 540 as to whether the seat needs to be moved in the up direction from its present position. If it is determined at 540 that the seat needs to be moved up from its present position, the patient positioning system controls the seat position switch (301 of FIG. 3) and the motor for the seat at 541 so that the seat can move only in the up direction. In addition, FIG. 28G is displayed at 541 on the display screen 16a instructing the user to move the seat in the up direction to a specific centimeter value by pressing the seat position switch in the up direction and illuminating the up direction on the screen display under the SEAT label. Finally, the LED direction indicator (305a of FIG. 3) adjacent to the up direction on the seat position switch is illuminated.

If it is determined at 540 that the seat does not need to be moved in the up direction, the seat position switch and the motors for the seat are controlled at 542 so that the seat can be moved only in the down direction. In addition, the user is instructed at 542 to move the seat in the down direction to a specific centimeter value, and also prompted to do this by illuminating the down direction below the SEAT label on the display screen and by illuminating the LED (305c of FIG. 3) adjacent the down direction on the seat position switch.

Figure 28H:
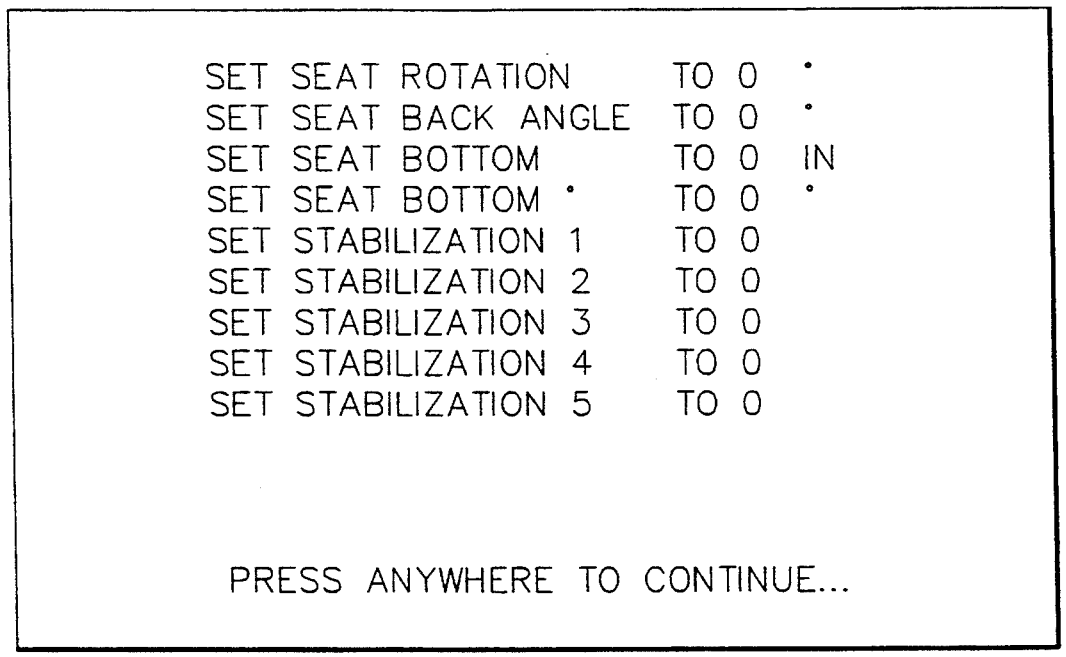

Regardless of whether the seat is to be moved in the up or the down direction, the patient positioning system then accepts input from the seat position switch the touch screen or the keyboard at 543. Once the user enters a selection, a determination is made at 544 as to whether the seat position switch was pressed in the correct up or down direction, or whether one of the options displayed in FIG. 28G was selected. If it is determined at 544a that the seat position switch was pressed in the correct up or down direction, the seat is moved in the correct up or down direction at 545 while the seat position switch is pressed. A determination is then made at 546 as to whether the standard or custom up/down seat position setting has been reached. If the standard or custom seat position has been reached, the index locations are displayed at 547 on the screen as illustrated in FIG. 28H. The user can press anywhere on the touch screen at 548 to continue processing. If it is determined at 546 that the standard or custom up/down seat position has not been reached, control is transferred to transition Block E so that the patient positioning system can continue to accept user input at the seat position switch, or from the keyboard or touch screen (Block 543).

If it was determined at 544a that the seat position switch was not pressed in the correct up or down direction, a determination is made at 544b as to whether one of the other options, namely, ESCape, MANUAL MODE, INDEX LOCATIONS, or ACCEPT, was selected. If it is determined at 544b that one of these options from the touch screen was selected, the patient positioning system proceeds to process the selected option, the details of which will be described with respect to FIG. 27I below. If it is determined that one of the options from the touch screen was not selected, the patient positioning system then continues at 543 to wait for input from the user either at the seat position switch, from the touch screen, or at the keyboard.

Figure 27F:
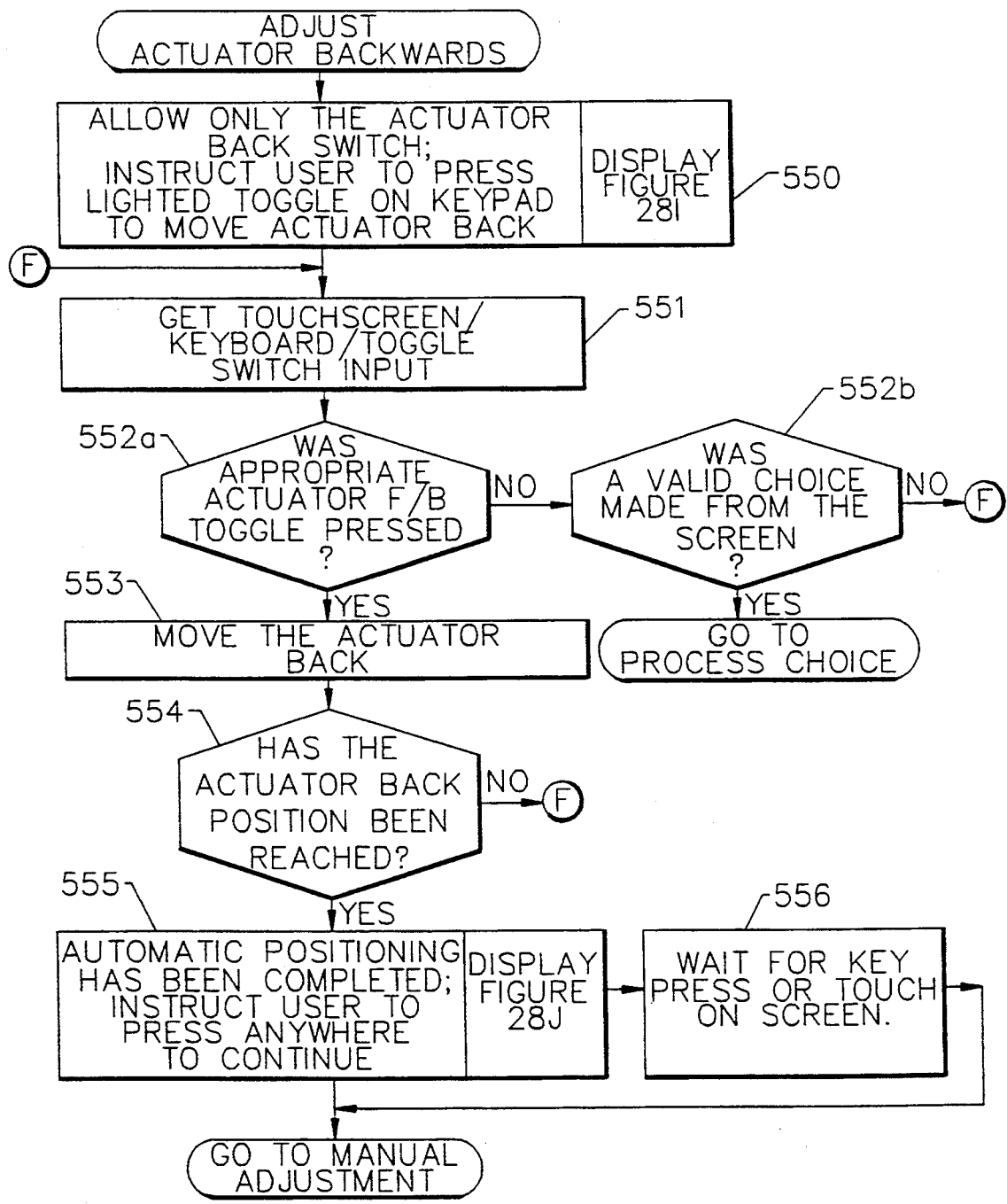
Figure 28I:
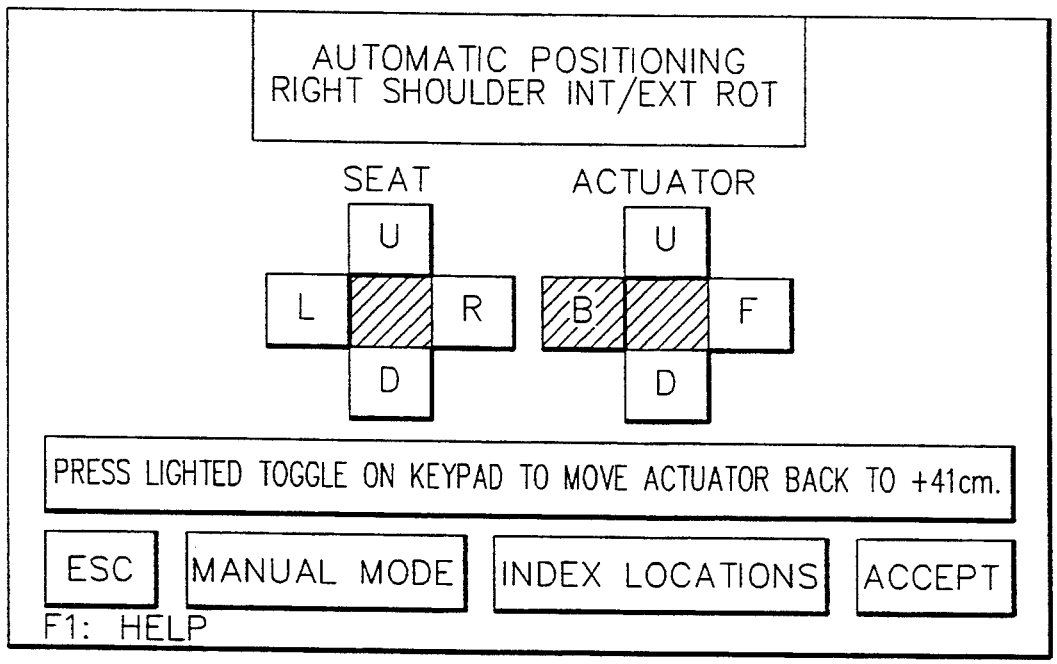
Figure 28J:
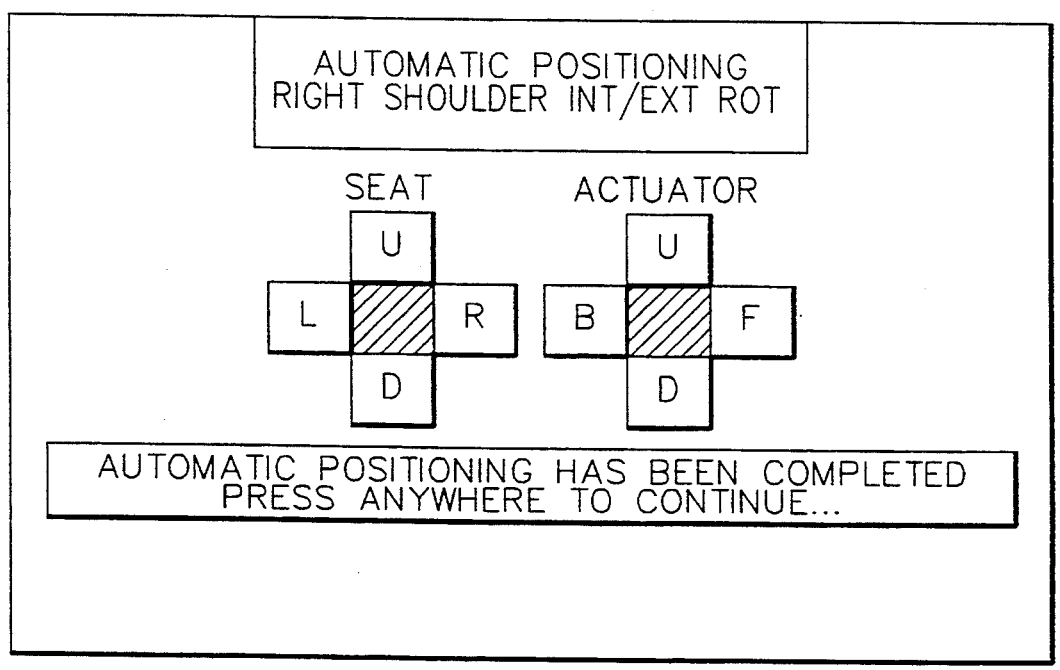
Figure 28K:
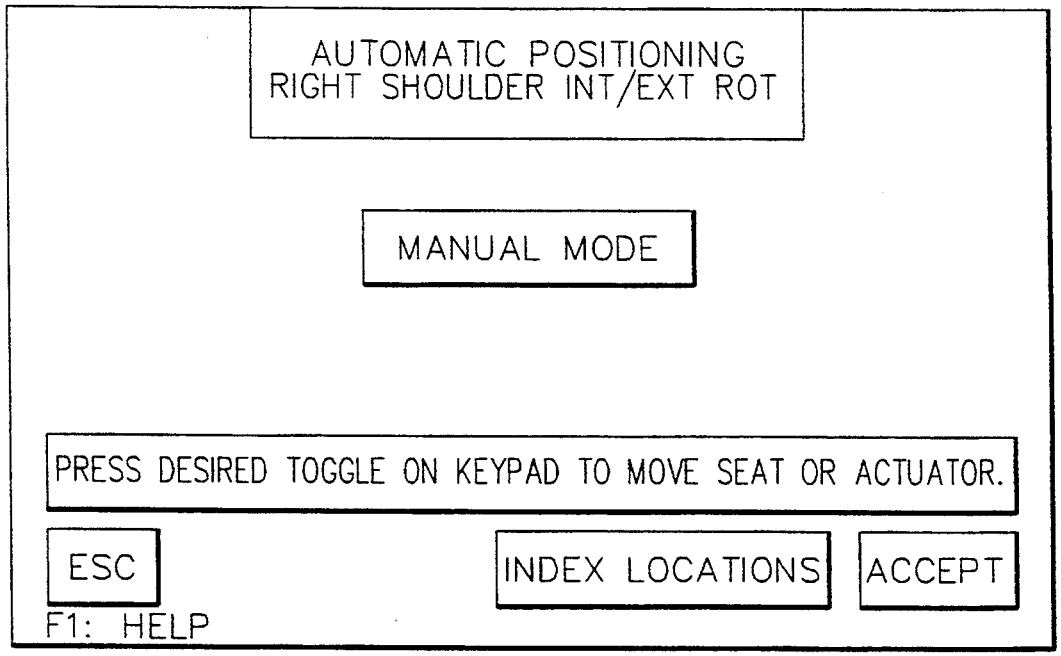

Referring to FIG. 27F, adjustment of the actuator in the backwards direction will now be described. Once the standard or custom up/down seat position has been reached, the actuator may be moved in the backwards direction to its correct location for the standard or custom forward/backward actuator position setting. The patient positioning system at 550 controls the actuator position switch (302 of FIG. 3) and the motors for the actuator to allow the actuator to be moved only in the backwards direction. In addition, FIG. 28I is displayed at 550 on the display screen 16a instructing the user to move the actuator in the backwards direction to a specific centimeter value. Still further, the backwards direction on the touch screen under the ACTUATOR label and the LED (306b of FIG. 3) adjacent the backwards direction for the actuator position switch are illuminated. Pressing the actuator position switch in the backwards direction, or selection of one of the other options, namely, ESCape, MANUAL MODE, INDEX LOCATIONS, or ACCEPT, or other input from the keyboard is accepted at 551.

A determination is then made at 552 as to whether the actuator patient switch was pressed or activated in the backward direction, or whether one of the options from FIG. 28I was selected. If it is determined at 552a that the actuator position switch was activated in the backward direction, the actuator is moved at 553 in the backwards direction while the actuator position switch is pressed in the backwards direction. While the actuator position switch is being pressed by the user in the backwards direction, a determination is made continuously at 554 to determine whether the standard or custom actuator backwards position setting has been reached. If the standard or custom actuator backwards position setting has been reached, automatic (standard or custom) positioning has been completed and the user is notified of the completion of this positioning process at 555 by displaying the screen illustrated in FIG. 28J. Thereafter, manual mode for further adjusting the seat and/or actuator is entered by pressing any key on the keyboard or any touch pad on the touch screen at 556. If it is determined at 554 that the standard or custom actuator backwards position setting has not been reached, control is transferred to transition Block F and the patient positioning system continues at 551 to accept input from the actuator position switch, the touch screen or the keyboard.

If it was determined at 552a that the actuator position switch was not pressed in the backwards direction, a determination is made at 552b as to whether one of the options on the touch screen, namely ESCape, MANUAL MODE, INDEX LOCATIONS, or ACCEPT, was selected. If it is determined that one of these options was selected, the patient positioning system then proceeds to process this choice, the details of which will be described with respect to FIG. 27I. If one of the options of the touch screen was not selected, take patient positioning system continues to wait at 551 for either activation of the actuator position switch in the backwards direction, or selection of one of the options from the touch screen.

Figure 27G:
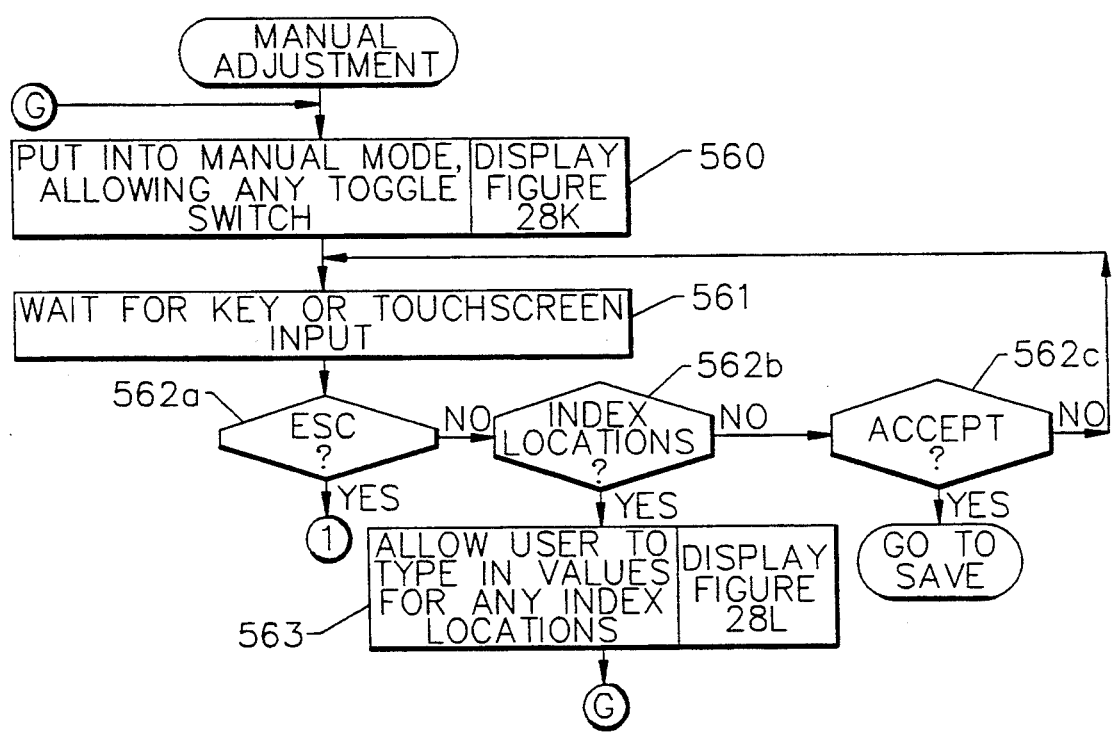

Referring now to FIG. 27G, the manual mode of the patient positioning system will now be described. Once the automatic (standard or custom) positioning of the seat and actuator is completed, the patient positioning system then enters manual mode at 560, allowing the seat and actuator position switches (301 and 302 of FIG. 3) to be toggled or pressed in any direction thereby causing the seat and actuator to move in any direction. This allows the seat and actuator to be further adjusted. The user is notified at 560 of the beginning of manual mode and instructed to move the seat or actuator switches in any direction by displaying the screen illustrated in FIG. 28K. Once the user is notified of manual mode, the patient positioning system waits at 561 for the user to select the direction of movement for either the seat or the actuator or select one of the options from the touch screen including ESCape, INDEX LOCATIONS and ACCEPT.

Figure 28L:
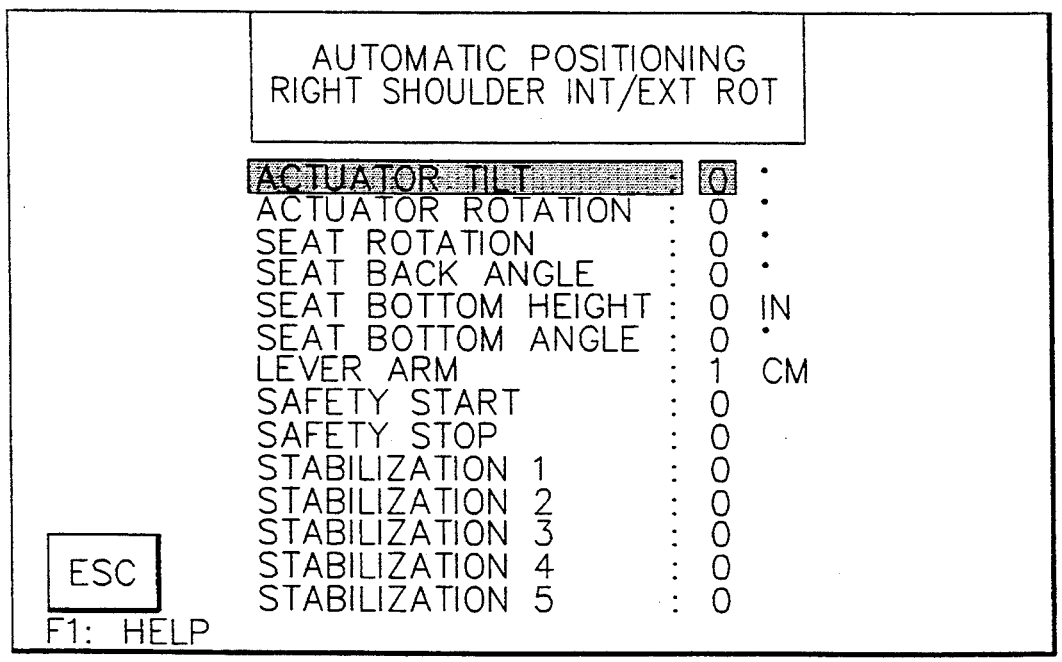

Once the selection has been entered, a determination is made at 562 as to which option was selected. If it is determined at 562a that the ESCape option was selected, control is then returned to displaying the option of STANDARD PATIENT POSITIONING or CUSTOM PATIENT POSITIONING at 502 of FIG. 27A. If it is determined at 562b that the INDEX LOCATIONS option is selected, the index locations are displayed at 563 as illustrated in FIG. 28L and values for any of the index locations can be entered using the keyboard. Once the index locations values have been entered, control is returned to display the manual mode screen at 560 to permit the selection of another option. If it is determined at 562c that the ACCEPT option was selected, control is transferred to transition Block SAVE, which will be described below.

Figure 27H:
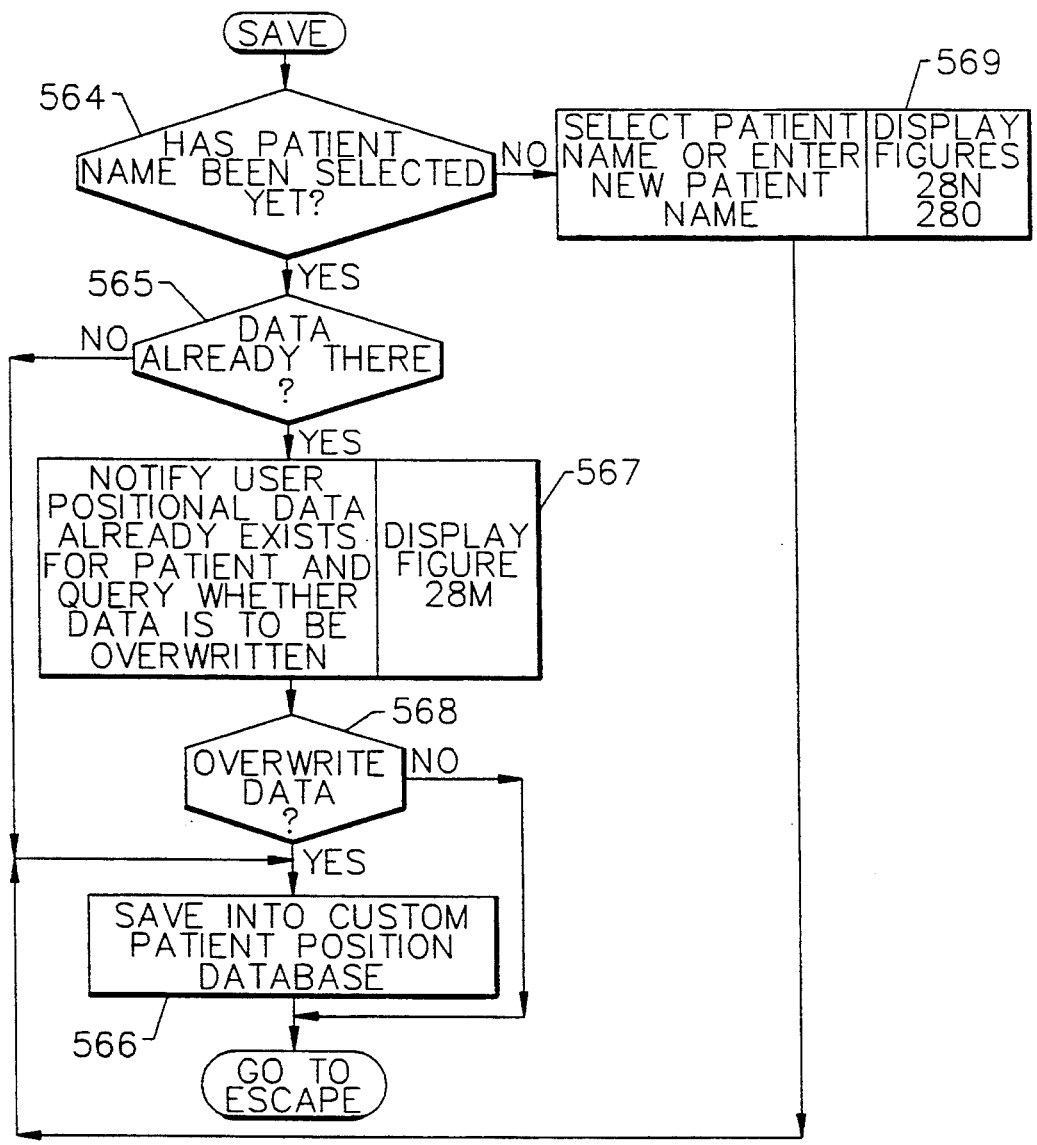

Referring to FIG. 27H, saving the patient position settings will now be described. At the outset, a determination is made at 564 whether a patient name has been selected. If a patient name has been selected, it is determined at 565 whether seat and dynamometer positions exist for the selected patient, joint, movement pattern and side to be exercised or evaluated. If it is determined at 565 that no positioning data exists for the selected patient, joint, movement pattern and side to be exercised or evaluated, the patient positioning data is stored at 566 in the custom patient position database.

If it is determined at 565 that patient positioning data already is stored in the custom patient position database for the selected patient, joint, movement pattern and side, the user is notified at 567 that position data already is stored in the custom patient position database for the selected patient, joint, movement pattern and side by displaying FIG. 28M on the display screen 16a. In addition, the patient positioning system asks the user whether or not the user desires to overwrite the data stored for this patient, joint, movement pattern and side. A determination is then made at 568 whether the user selected to overwrite the patient, joint, movement pattern and side positioning data by selecting the YES option on the touch screen. If the user selected to overwrite the custom position data, the position data for this patient, joint, movement pattern and side is stored in the custom patient position database at 566 and control is transferred to transition Block ESCAPE which will be described with respect to FIG. 27I to determine whether the present processing originated as an exercise, evaluation, or in the "Finish Side". If the user selects not to overwrite the position data, the position data stored in the custom patient position database is not overwritten and control is similarly transferred to transition Block ESCAPE.

If it was determined at 564 that a patient name had not been selected, a list of patient names is displayed at 569 on the screen as illustrated in FIG. 28N allowing the user to scroll through a list of patients or enter a new patient by selecting the new patient option on the bottom of the screen illustrated in FIG. 28N. Once the patient name has been selected or the new patient has been entered, information relating to that patient is displayed as illustrated in FIG. 28O permitting the entry or modification of information relating to the selected or new patient. Thereafter, the position data for the selected or new patient, joint, movement pattern and side is stored in the custom patient position database at 566 and control is then transferred to transition Block ESCAPE.

Referring to FIG. 27I, the details of the implementation of the PROCESS CHOICE routine will now be described. A determination is made at 570 as to which of the options, namely ESCape, MANUAL MODE, INDEX LOCATIONS, or ACCEPT, was selected. If it is determined at 570a that the ESCape option was selected, the patient positioning system then determines at 571 whether the present processing originated from the exercise mode, the "begin" step of the evaluation mode, or the "Finish Side" of the evaluation mode. If it is determined at 571a that processing originated from the exercise mode, control is returned to display the options of STANDARD PATIENT POSITIONING and CUSTOM PATIENT POSITIONING at 502 of FIG. 27A to permit the user to escape out of the present positioning process and begin the entire positioning process again. If it is determined at 571b that processing originated at the beginning of the evaluation mode, control is returned to evaluation processing for the patient positioning for isokinetic, passive or isotonic evaluations which will be described with respect to FIG. 27J. Finally, if it is determined at 571c that the processing began with the FINISH SIDE routine of the evaluation mode, control is returned to the beginning of the FINISH SIDE routine of the evaluation mode which will be described with respect to FIG. 27K.

If the user selected MANUAL MODE as determined at 570b, control is transferred to transition Block G to reenter manual mode as described with respect to FIG. 27G at 560. If neither the ESCape or MANUAL MODE options were selected, a determination is made at 570c as to whether the INDEX LOCATIONS option was selected. If it is determined at 570c that INDEX LOCATIONS was selected, the present values for the index locations are displayed on the screen at 572 and the new values can be entered on the keyboard. Control is then returned to the calling function.

Finally, if neither the ESCape, MANUAL MODE, or INDEX LOCATIONS option was selected, it is concluded at 573 that the ACCEPT option was selected. Thereafter, control is transferred to the SAVE Routine which was described with respect to FIG. 27H.

Figure 27J:
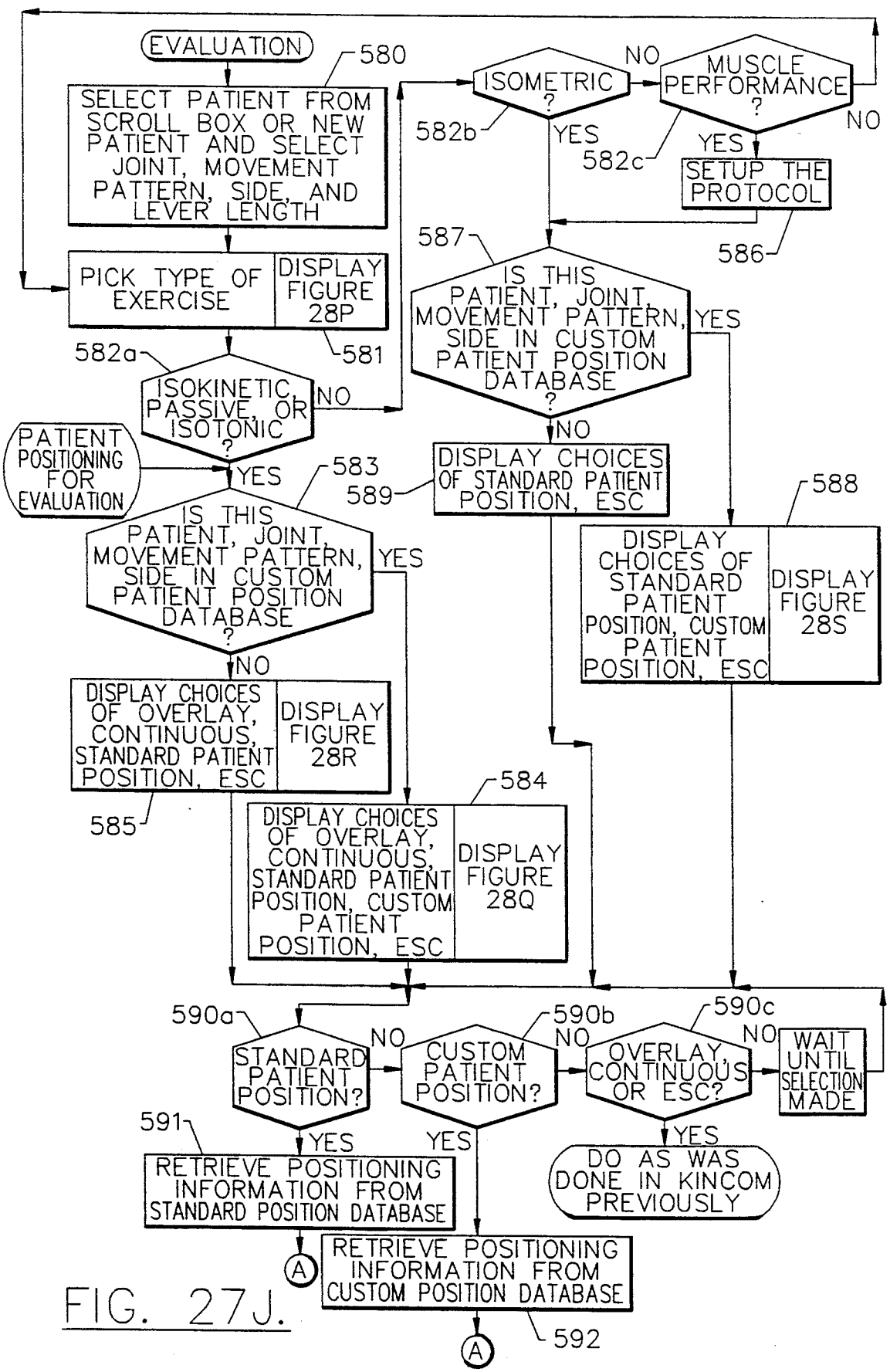

Referring to FIG. 27J, processing of the patient positioning system for standard and custom patient positioning while in the evaluation mode will now be described. If the evaluation mode is selected, a list of patients can be selected from those displayed on the screen, which may be scrolled using the technique described in U.S. Pat. No. 5,054,774 to Belsito, or a new patient may be entered at 580. In addition, the joint, movement pattern, side and lever length must be selected for the evaluation at 580. Thereafter, the exercises upon which a patient may be evaluated are displayed at 581 as illustrated in FIG. 28P and the desired exercise mode for which the patient is to be evaluated is selected by indicating the selection on the touch screen.

Figure 28Q:
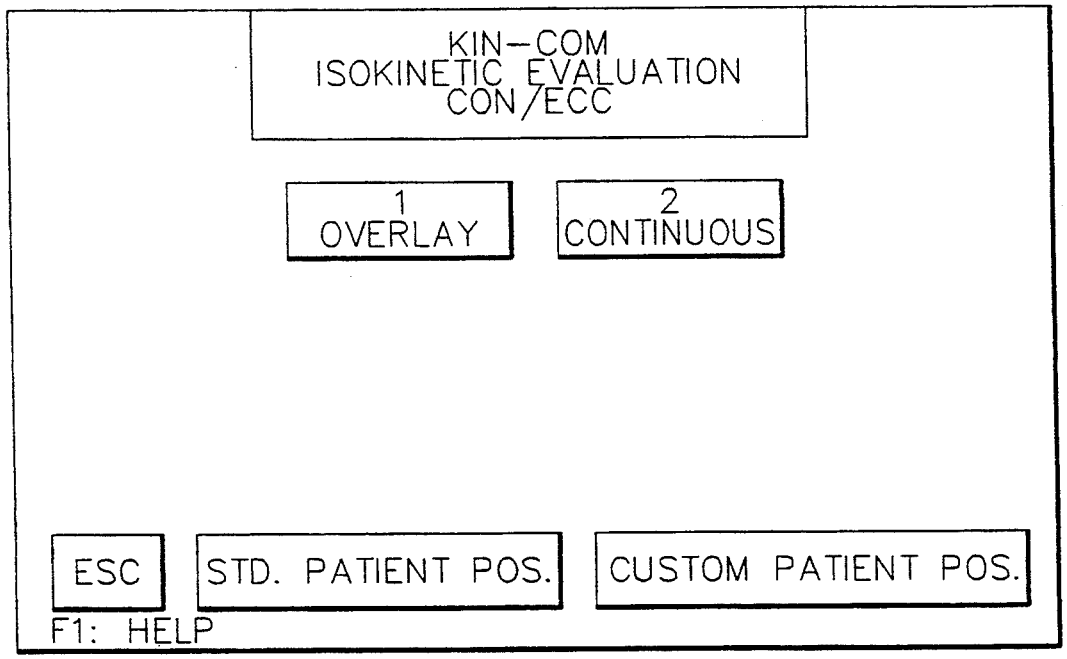
Figure 28R:
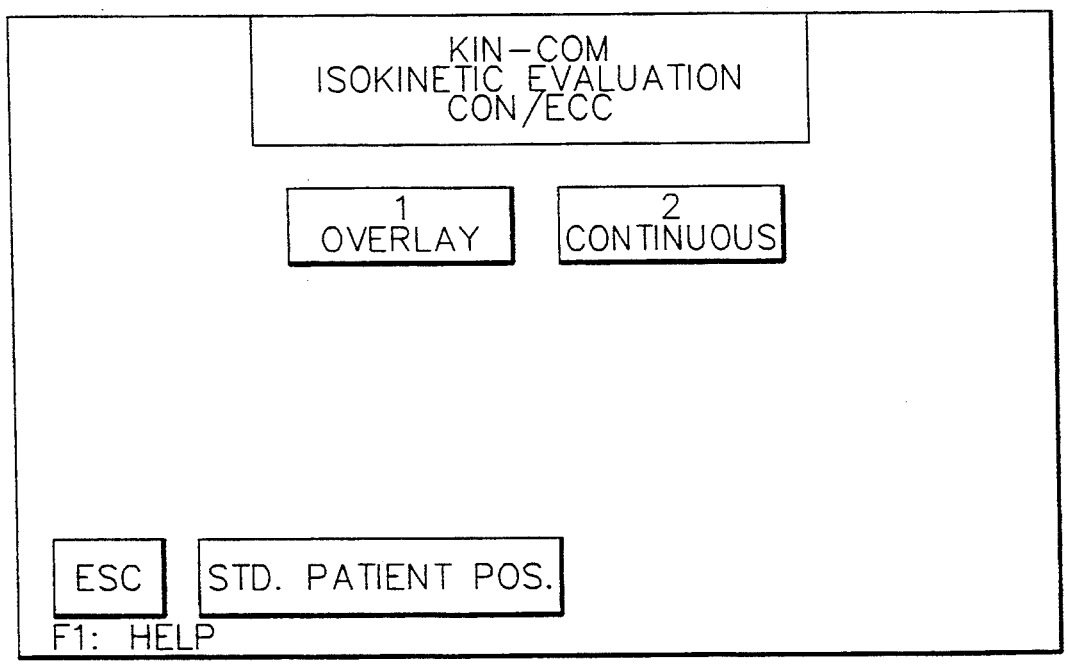

A determination is then made at 582 as to which exercise for evaluation was selected. If it is determined at 582a that isokinetic, passive or isotonic was selected, the custom patient position database is accessed to determine at 583 whether the patient and the corresponding joint, movement pattern, and side is stored in the custom patient position database for the selected patient. If it is determined at 583 that the patient, joint, movement pattern and side are stored in the custom patient position database, the standard patient positioning and custom patient positioning options are displayed at 584 on the screen as illustrated in FIG. 28Q. This permits the user to select standard patient positioning or custom patient positioning. If it is determined at 583 that the selected patient, joint, movement pattern and side are not stored in the custom patient positioning database, the user is given the option of selecting the standard patient positioning at 585 by displaying the options as illustrated in FIG. 28R.

Figure 28S:
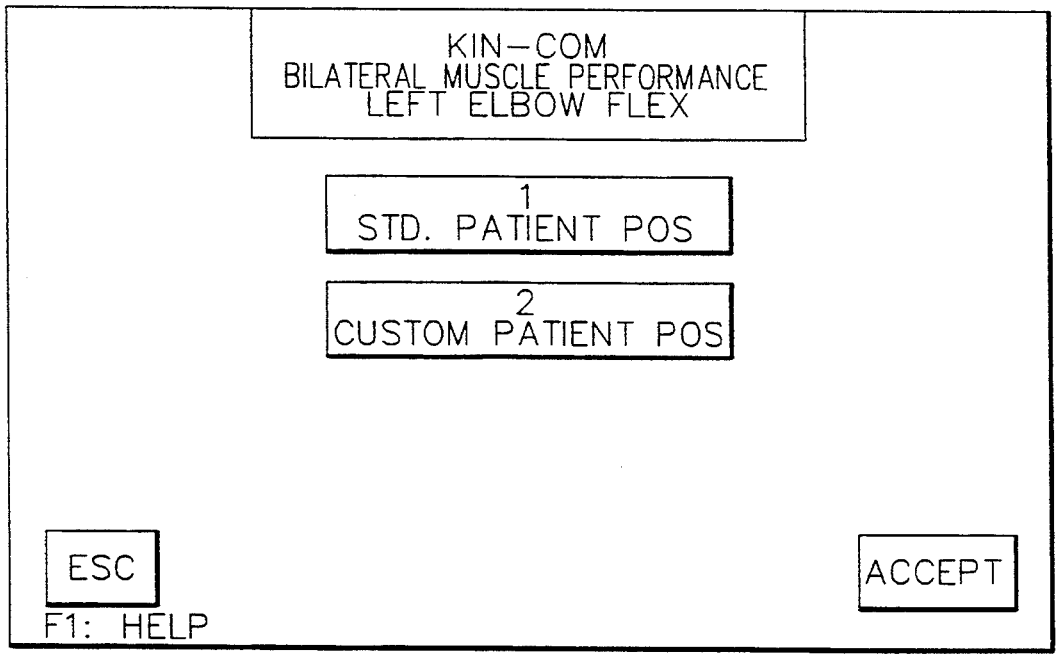

If it is determined at 582a that neither the isokinetic, passive or isotonic exercises were selected for evaluation, a determination is made at 582b as to whether the isometric exercise was selected and at 582c as to whether the muscle performance exercise for evaluation was selected. If either of these two were selected, processing is essentially the same as that for isokinetic, passive, or isotonic except that when the options are displayed to the user, the OVERLAY and CONTINUOUS options are not available. Specifically, if isometric was selected, a determination is made at 587 as to whether the selected patient, joint, movement pattern and side is presently stored in the custom patient position database. If this data is stored in the custom patient position database, the STANDARD PATIENT POSITIONING and CUSTOM PATIENT POSITIONING options are displayed at 588 as illustrated in FIG. 28S. If the selected patient, joint, movement pattern and side are not stored in the custom patient positioning database, the only option available is either standard patient positioning or ESCape and the display (not shown) which appears on the screen at 584 is similar to that illustrated in FIG. 28S except the CUSTOM PATIENT POSITIONING option is not available.

If it is determined at 582c that the muscle performance exercise is to be evaluated, the protocol for the muscle performance exercise is set up at 586 and then the processing is the same as it was for the evaluation of the isometric exercise in terms of determining whether the selected patient, joint, movement pattern and side are stored in the custom patient position database and then displaying the options of STANDARD PATIENT POSITIONING and CUSTOM PATIENT POSITIONING, or only STANDARD PATIENT POSITIONING.

After the particular available options have been displayed among those of OVERLAY, CONTINUOUS, STANDARD PATIENT POSITIONING, CUSTOM PATIENT POSITIONING and ESCape, a determination is made at 590 as to which option was selected. If it is determined at 590a that STANDARD PATIENT POSITIONING was selected, the standard position settings for the selected joint, movement pattern and side are retrieved from the standard patient position database at 591. Thereafter, control is returned to 510 of FIG. 27B to begin the process of moving the actuator and the seat to the standard patient position settings. If the STANDARD PATIENT POSITION option was not selected, a determination is made at 590b as to whether the CUSTOM PATIENT POSITION option was selected. If the CUSTOM PATIENT POSITION option was selected, the custom patient position settings for the selected patient, joint, movement pattern and side are retrieved from the custom patient position database at 592 and control is also transferred to 510 of FIG. 27B to begin the process of moving the seat and actuator to the custom patient position settings for the selected patient, joint, movement pattern and side. If neither the STANDARD PATIENT POSITION nor CUSTOM PATIENT POSITION option was selected, a determination is made at 590c as to whether the OVERLAY, CONTINUOUS, or ESCape option was selected. If one of these options was selected, the muscle exercise machine is controlled for the selected exercise as described in the McArthur and Belsito patents.

Figure 27K:
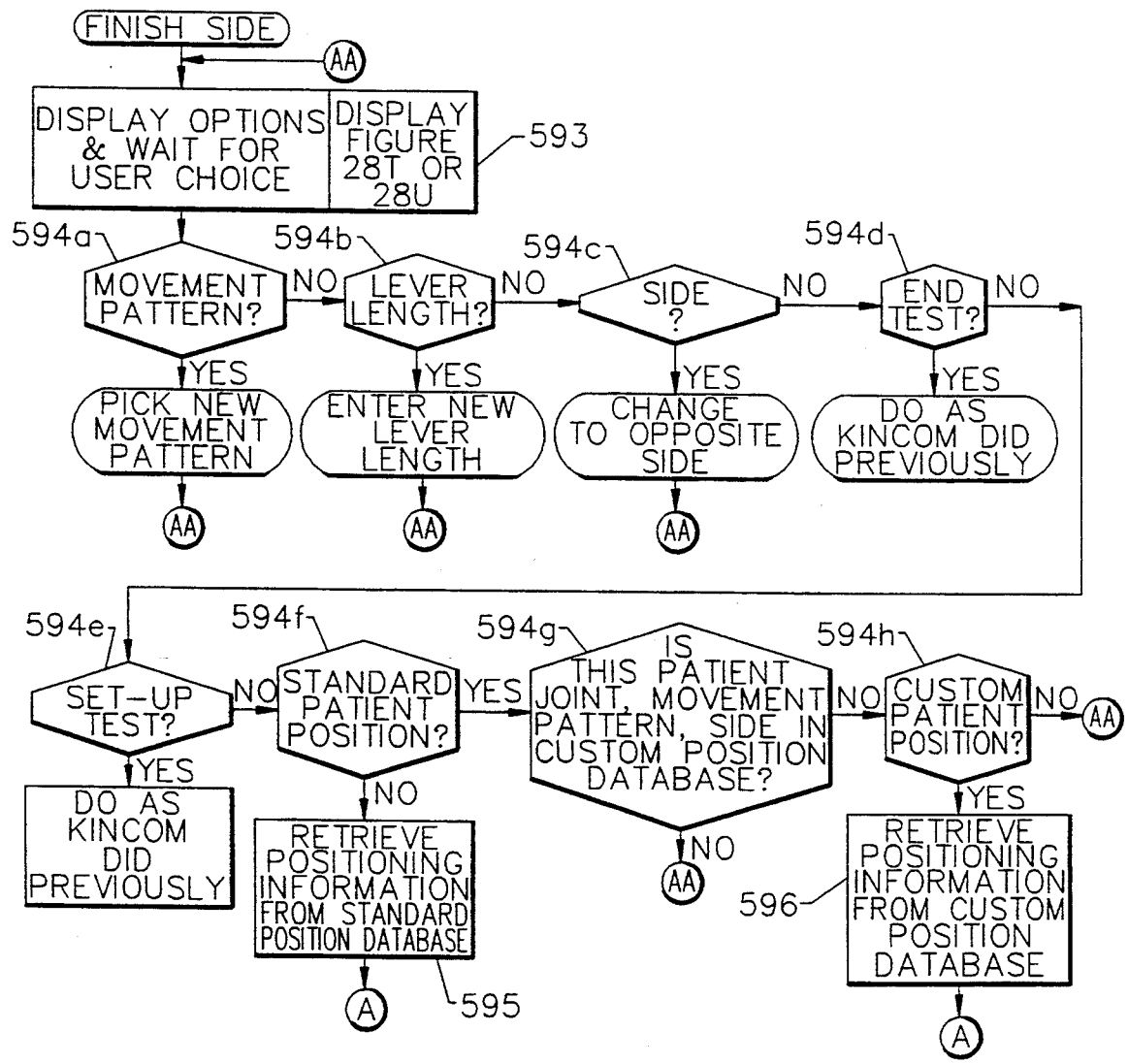

Finally, referring to FIG. 27K, details of the processing of the "Finish Side" routine will now be described. Generally speaking, the Finish Side routine is implemented during the evaluation mode after all the data has been collected and the user selects the ESCape option indicating that the evaluation of the selected side for the patient has been completed and the user can then alter the movement pattern, lever length, side and/or patient position for the next evaluation.

Figure 28T:
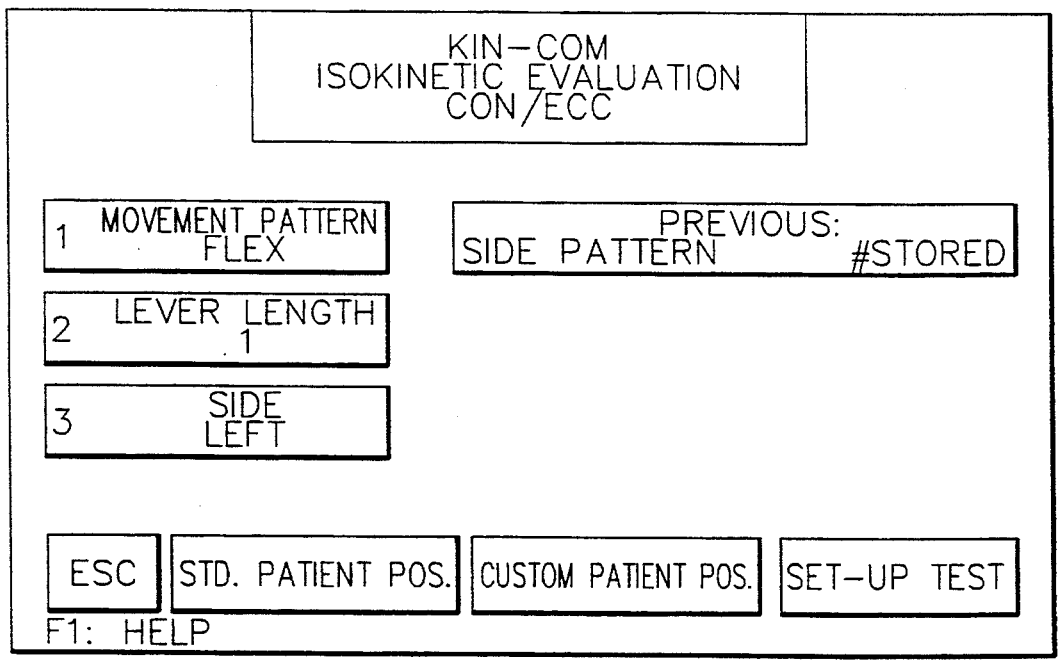
Figure 28U:
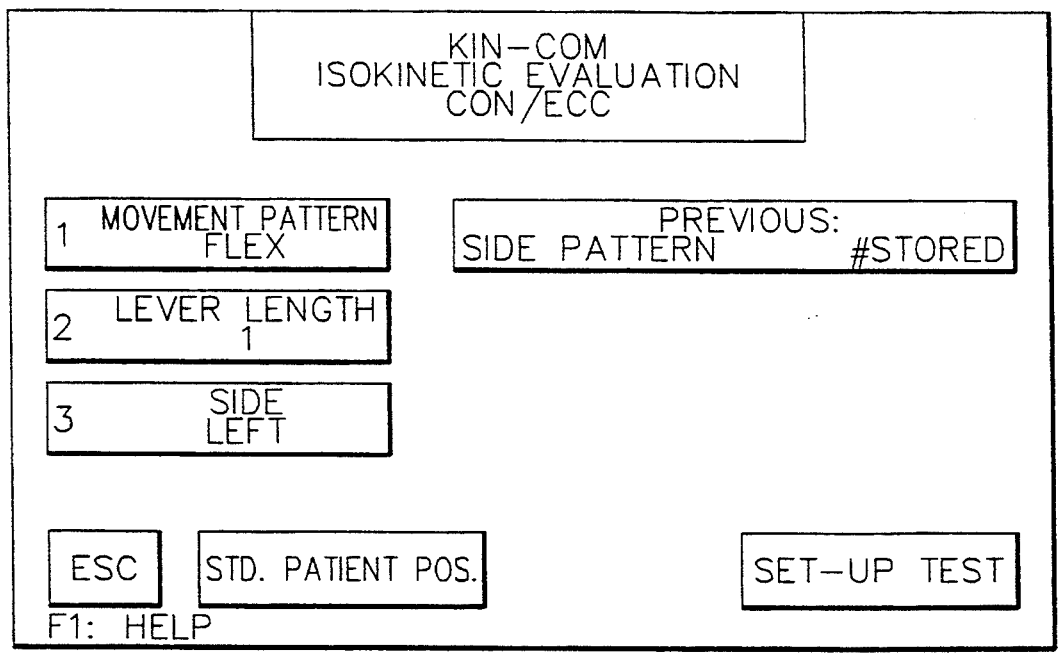

At the outset, the options for changing the setup (movement pattern, lever length, and side), and patient position are displayed on the screen at 593, as illustrated in FIG. 28T or FIG. 28U. FIG. 28T will be displayed when data for the particular patient and the selected joint, movement pattern and side is presently stored in the custom patient position database. FIG. 28U will be displayed on the screen when no position data for the joint, movement pattern and side for the selected patient is stored in the custom patient position database. After displaying the options for proceeding, the patient positioning system waits for the user to select a choice by pressing the key on the touch screen. Once an option has been selected, a determination is made at 594 as to which option was selected.

Based on the determination at 594a that the MOVEMENT PATTERN option was selected, the system will then proceed to allow the user to select a different pattern of movement, and then allow the user to select another option at 593. If it is determined at 594b that the LEVER LENGTH option was selected, the user will be permitted to enter a new lever length, and the system will then display either FIG. 28T or FIG. 28U to allow the user to select another option at 593.

Based on a determination at 594c that the SIDE option was selected, the system will proceed to change the side to be evaluated to be opposite that which was previously evaluated and then display at 593 either FIG. 28T or FIG. 28U to allow the user to select another option. If the END TEST option or the SET-UP TEST option was selected as determined at 594d, or 594e, respectively, control of the muscle exercise machine continues as described in the McArthur and Belsito patents.

Based upon a determination at 594f that STANDARD PATIENT POSITION was selected, the standard patient position settings are retrieved from the standard patient position database at 595 for the selected patient, joint, movement pattern and side. Control is then returned to 510 of FIG. 27B to permit movement of the seat and actuator to the standard patient position settings.

If it is determined at 594f that STANDARD PATIENT POSITIONING was not selected, a determination is made at 594g as to whether the selected patient, joint, movement pattern and side are presently stored in the custom patient position database. If this data is not stored in the custom patient position database, control is returned to the beginning of the Finish Side routine at 593 to permit the user to select another option with respect to the movement pattern, lever length, end test, standard patient position, custom patient position, or set up test.

In the event that the joint, movement pattern and side data are stored in the custom patient position database for this patient, a determination is made at 594h as to whether CUSTOM PATIENT POSITION was selected. If CUSTOM PATIENT POSITION was not selected, control is returned to the beginning of the Finish Side Routine at 593 to permit the user to select another option. If CUSTOM PATIENT POSITION was selected, the custom patient position settings for this patient and the selected joint, movement pattern and side to be evaluated are retrieved from the custom patient position database at 596 and control is returned to 510 of FIG. 27B to begin the process of moving the seat and dynamometer to the custom patient position settings for this patient, joint, movement pattern and side.

In the drawings and specification, there has been set forth a preferred embodiment of the invention, and although specific terms are employed, they are used in a generic and descriptive sense only and not for purposes of limitation.

That which is claimed is:

1. A muscle exercise machine comprising:
   a seat for supporting a patient thereon;
   an actuator having an output shaft for attaching an exercise element thereto;
   data storage means for storing therein names of patients, names of exercises and seat positions in relation to said actuator and actuator positions in relation to said seat for exercises;
   position selecting means for selecting a direction of positioning movement of said seat in relation to said actuator and a direction of positioning movement of said actuator in relation to said seat, said position selecting means comprising:
      position direction indicating means for indicating a direction of positioning movement of said seat relative to said actuator based upon the relative position of said seat and said actuator stored in said data storage means and for indicating a direction of positioning movement of said actuator relative to said seat based upon the relative position of said actuator and said seat stored in said data storage means; and
      position direction input means for accepting position selection of said seat in relation to said actuator and said actuator in relation to said seat in response to the direction indicated by said position direction indicating means;
   position controlling means, operationally connected to said position selecting means, said seat and said actuator, for controlling positioning movement of said seat in relation to said actuator and positioning movement of said actuator in relation to said seat upon manipulation of said position selecting means by a user; and
   data processing means, operationally connected to said position controlling means, said position selecting means and said data storage means, for activating and deactivating said position selecting means and said position controlling means based upon the position of said seat relative to said actuator stored in said data storage means, and for activating and deactivating said position selecting means and said position controlling means based upon the position of said actuator relative to said seat for an exercise stored in said data storage means.

2. The muscle exercise machine of claim 1 wherein said position direction indicating means comprises:
   seat position direction indicating means for indicating a direction of positioning movement of said seat relative to said actuator based upon the relative position of said seat and said actuator stored in said data storage means, and actuator position direction indicating means for indicating a direction of positioning movement of said actuator relative to said seat based upon the relative position of said actuator and said seat stored in said data storage means; and wherein said position direction input means comprises seat position direction input means for accepting position selection of said seat in relation to said actuator in response to the direction indicated by said seat position direction indicating means, and actuator position direction input means for accepting position selection of said actuator in relation to said seat in response to the direction indicated by said actuator position direction indicating means.

3. The muscle exercise machine of claim 2, wherein said seat position direction indicating means comprises at least one light emitting diode and said actuator position direction indicating means comprises at least one light emitting diode.

4. The muscle exercise machine of claim 2, wherein said seat position direction input means comprises an electrical switch including a plurality of switch positions associated with said seat and said actuator position direction input means comprises an electrical switch including a plurality of switch positions associated with said actuator.

5. The muscle exercise machine of claim 1 further comprising a display device, operationally connected to said data processing means;

an input device, operationally connected to said data processing means;

name display means included in said data processing means, for displaying on said display device, at least some of the names of users of said muscle exercise machine;

name input accepting means included in said data processing means, for accepting selection of one name at said input device, from the at least some of the names displayed on said display device;

exercise display means included in said data processing means, for displaying on said display device, at least some of the exercises performed on said muscle exercise machine for the selected one name;

exercise input accepting means included in said data processing means, for accepting selection of one exercise at said input device, from the at least some of the exercises displayed on said display device;

position display means included in said data processing means, for displaying on said display device, at least some of the seat and actuator positions for the selected one name and one exercise;

position input accepting means included in said data processing means, for accepting selection of one seat and actuator position at said input device, from the at least some of the seat and actuator positions displayed on said display device; and indicating controlling means included in said data processing means, for controlling the position direction indicating means in response to the selected one seat and actuator position; and wherein said position controlling means includes means for accepting manipulation of said position direction input means in response to position direction indicating means, and controlling the activation and deactivation of the position controlling means to perform the seat and actuator position manipulation based on the predetermined seat and actuator position.

6. The muscle exercise machine of claim 5, said data processing means further comprising means for storing the seat and actuator positions accepted by said position input accepting means in response to the direction indicated by the position direction indicating means in said storage means in association with the selected patient.

7. The muscle exercise machine of claim 1, wherein said position selecting means further comprises a seat position selecting means for selecting the direction of positioning movement of said seat relative to said actuator and an actuator position selecting means for selecting the direction of positioning movement of said actuator relative to said seat; and wherein said position controlling means comprises a seat position controlling means for controlling the positioning movement of said seat relative to said actuator in response to the manipulation of the seat position selecting means and an actuator position controlling means for controlling the positioning movement of said actuator relative to said seat in response to the manipulation of the actuator position selecting means.

8. The muscle exercise machine of claim 7, wherein said seat position controlling means consists of a first motor for moving said seat in a horizontal direction relative to said actuator and a second motor for moving said seat in a vertical direction relative to said actuator, and wherein said actuator position controlling means consists of a first motor for moving said actuator in a horizontal direction relative to said seat and a second motor for moving said actuator in a vertical direction relative to said seat.

9. The muscle exercise machine of claim 1, wherein said position direction indicating means comprises at least one light emitting diode.

10. The muscle exercise machine of claim 1, wherein said position direction input means comprises at least one electrical switch including a plurality of switch positions.

11. A patient positioning system for a muscle exercise machine comprising:

patient supporting means for supporting a patient thereon;

an exercise element adapted for manipulation by a patient supported on said patient supporting means;

data storage means for storing therein names of exercises and relative positions of the patient supporting means arid the exercise element;

position direction indicating means, responsive to said data storage means, for indicating a direction of positioning movement of the patient supporting means and the exercise element based upon the relative position of the patient supporting means and the exercise element stored in said data storage means;

position direction input means for accepting position selection of the patient supporting means and the exercise element in response to the direction indicated by the position direction indicating means; and position controlling means, operationally connected to said patient supporting means, said exercise element and said position direction input means, for controlling the relative positioning movement of the patient supporting means and the exercise element in response to the position accepted by the position direction input means.

12. The patient positioning system of claim 11 wherein said position controlling means further comprises position identification means for identifying the relative position of said patient supporting means and said exercise element.

13. The patient positioning system of claim 12 wherein said data storage means further comprises means for storing therein names of patients in association with names of exercises and the relative positions of said patient supporting means and said exercise element accepted by said position direction input means in response to the direction indicated by the position direction indicating means for exercises, and wherein said patient positioning system for a muscle exercise machine further compromises:

data processing means, operationally connected to said position direction indicating means, said position identification means and said data storage means, for controlling the position direction indicating means in response to the relative position of the patient supporting means and the exercise element stored in said data storage means and the relative position of the patient supporting means and the exercise element identified by said position identification means.

14. The patient positioning system of claim 13 further comprising:

a display device, operationally connected to said data processing means;

an input device, operationally connected to said data processing means;

name display means included in said data processing means, for displaying on said display device, at least some of the names of users of said muscle exercise machine;

name input accepting means included in said data processing means, for accepting selection of one name at said input device, from the at least some of the names displayed on said display device;

exercise display means included in said data processing means, for displaying on said display device, at least some of the exercises performed on said muscle exercise machine for the selected one name;

exercise input accepting means included in said data processing means, for accepting selection of one exercise at said input device, from the at least some of the exercises displayed on said display device;

position display means included in said data processing means, for displaying on said display device, at least some of the seat and actuator positions for the selected one name and one exercise; and position input accepting means included in said data processing means, for accepting selection of one seat and actuator position at said input device, from the at least some of the seat and actuator positions displayed on said display device.

15. The patient positioning system of claim 11, wherein said position direction input means comprises a seat position direction input means for selecting the direction of positioning movement of said seat relative to said actuator and an actuator position direction input means for selecting the direction of positioning movement of said actuator relative to said seat; and wherein said position controlling means comprises a seat position controlling means for controlling the positioning movement of said seat relative to said actuator in response to the manipulation of the seat position direction input means and an actuator position controlling means for controlling the positioning movement of said actuator relative to said seat in response to the manipulation of the actuator position direction input means.

16. The patient positioning system of claim 15, wherein said seat position controlling means consists of a first motor for moving said seat in a horizontal direction relative to said actuator and a second motor for moving said seat in a vertical direction relative to said actuator, and wherein said actuator position controlling means consists of a first motor for moving said actuator in a horizontal direction relative to said seat and a second motor for moving said actuator in a vertical direction relative to said seat.

17. The patient positioning system of claim 11, wherein said position direction indicating means comprises at least one light emitting diode.

18. The patient positioning system of claim 11, wherein said position direction input means comprises at least one electrical switch including a plurality of switch positions.

19. A muscle exercise machine comprising:

patient supporting means for supporting a patient thereon;

an exercise element adapted for manipulation by a patient;

means, operationally connected to said patient supporting means and said exercise element, for effecting relative positioning movement of said patient supporting means and said exercise element to define an exercise position, said relative positioning movement effecting means comprising position direction input means, for accepting selection of a relative position of said exercise element and said patient supporting means;

position direction indicating means for indicating a direction of positioning movement of said relative positioning movement effecting means; and automatic positioning means for activating said position direction indicating means to indicate a direction of relative positioning movement of said relative positioning movement effecting means; and data storage means, for storing therein patient names and associated patient exercise names; and means for storing in said data storage means, an exercise position defined by said patient supporting means and said exercise element and corresponding to a patient name and a patient exercise name;

wherein said automatic positioning means is responsive to said data storage means and moves at least one of said patient supporting means and said exercise element to an exercise position which is stored in said data storage means.

20. The muscle exercise machine of claim 19 wherein said storing means is further responsive to said relative positioning movement effecting means, for automatically storing an exercise position defined by said relative positioning movement effecting means in said data storage means using said storing means.

21. The muscle exercise machine of claim 20 wherein said automatic positioning means is further responsive to said position direction input means for activating said relative positioning movement effecting means to move at least one of said patient supporting means and said exercise element to an exercise position stored in said data storage means.

22. The muscle exercise machine of claim 21 wherein said automatic positioning means discontinues positioning movement of said at least one of said patient supporting means and said exercise element to said exercise position upon deactivation of said position direction input means.

23. The muscle exercise machine of claim 19 wherein said position direction input means is an electrical switch including a plurality of switch positions, and said position direction indicating means is a corresponding plurality of illuminated indicators.

24. A muscle exercise and rehabilitation apparatus comprising a seat for supporting a patient thereon, seat mounting means comprising a seat base member, a vertical first post slidably mounted to said seat base member for selective movement in either direction along a linear, laterally directed path of movement, with said first post defining a vertical seat axis, first seat positioning means for moving said seat laterally in either direction along said lateral path of travel, and second seat positioning means for moving said seat in either direction along said vertical seat axis, a rotary actuator comprising an output shaft defining a rotational axis, an arm connected to said output shaft and extending radially therefrom, and drive means for selectively rotating said shaft in either direction about said rotational axis, actuator mounting means mounting said actuator adjacent said seat so that a patient supported on said seat can engage said arm of said actuator, and comprising an actuator base member, a vertical second post slidably mounted to said actuator base member for selective movement in either direction along a linear, longitudinally directed path of movement which is perpendicular to said linear laterally directed path of movement, with said second post defining a vertical actuator axis, first actuator positioning means for moving said actuator in either direction along said longitudinal path of movement, and second actuator positioning means for moving said actuator in either direction along said vertical actuator axis, a seat switch having four seat switch positions for selectively (1) operating said second seat positioning means to move said seat up, (2) operating said second seat positioning means to move said seat down, (3) operating said first seat positioning means to laterally move said seat to the right, (4) operating said first seat positioning means to laterally move said seat to the left, a light associated with each of said four seat switch positions so as to visually indicate which one of said four seat switch positions should be selected, an actuator switch having four actuator switch positions for selectively (1) operating said second actuator positioning means to move said actuator up, (2) operating said second actuator positioning means to move said actuator down, (3) operating said first actuator positioning means to longitudinally move said actuator in a back direction, (4) operating said first actuator positioning means to longitudinally move said actuator in a forward direction, a light associated with each of said four actuator switch positions so as to visually indicate which one of said four actuator switch positions should be selected, storage means for storing the names of patients and predetermined settings for the height of said seat, the lateral position of said seat, the height of said actuator, and the longitudinal position of said actuator, with respect to a particular exercising routine for each of the patients, position input accepting means for accepting selection of a name of a patient, a particular exercising routine, and a seat height position, a seat lateral position, an actuator height position and an actuator lateral position corresponding to said patient and said particular exercising routine, stored in said storage means, control means responsive to the actuation of said position input accepting means (1) for selecting the seat switch position to move the seat to the selected setting for its height stored in said storage means and the seat switch position to move the seat laterally to the selected setting for its lateral position stored in said storage means, and illuminating the associated lights in sequence, and (2) selecting the actuator switch position to move the actuator to the selected setting for its height stored in said storage means and the actuator switch position to move the actuator longitudinally to the selected setting for its longitudinal position stored in said storage means, and illuminating the associated lights in sequence.

25. A method for positioning a patient on a muscle exercise machine having a seat for supporting a patient thereon, an actuator having an output shaft for attaching an exercise element thereto, a data processor for controlling positioning movement of the seat and the actuator, and a display device, data storage means, and an input device operationally connected to the data processor; said method comprising the steps of:

selecting a direction of positioning movement of said seat relative to said actuator and a direction of positioning movement of said actuator relative to said seat, wherein said selecting step comprises the steps of:

indicating a direction of positioning movement of the seat relative to the actuator based upon the relative position of the seat and the actuator and indicating a direction of positioning movement of the actuator relative to the seat based upon the relative position of the actuator and the seat; and accepting selection of a direction of positioning movement of the seat relative to the actuator and the actuator relative to the seat in response to the direction indicated; and controlling the positioning movement of said seat relative to said actuator and the positioning movement of said actuator relative to said seat in response to the selection of a direction of positioning movement of the seat and the actuator;

activating and deactivating the selection of a direction of positioning movement of the seat and the actuator, and the control of the positioning movement of the seat and the actuator based on the relative position of the seat and the actuator; and storing in said data storage means names of patients, names of exercises and seat positions relative to said actuator and actuator positions relative to said seat for exercises.

26. The method of claim 25 further comprising the steps of:
    displaying on said display device, at least some of the names of users of said muscle exercise machines;
    accepting selection of one name at said input device, from the at least some of the names displayed on said display device;
    displaying on said display device, at least some of the exercises performed on said muscle exercise machine for the selected one name;
    accepting selection of one exercise at said input device, from the at least some of the exercises displayed on said display device;
    displaying on said display device, at least some of the seat and actuator positions for the selected one name and one exercise;
    accepting selection of one seat and actuator position at said input device from the at least some of the seat and actuator positions displayed on said display device; and
    controlling the indication of direction of positioning movement of the seat and the actuator in response to the selected one seat and actuator position.

27. The method of claim 26, further comprising the step of storing the seat and actuator positions accepted in response to the direction of the positioning movement of the seat and the actuator indicated in said storage means in association with the selected patient.

28. The method of claim 25, wherein said selecting step further comprises the steps of selecting a direction of positioning movement of the seat relative to the actuator and selecting a direction of positioning movement of the actuator relative to the seat, and wherein said positioning movement controlling step comprises the steps of controlling the positioning movement of the seat relative to the actuator in response to the selection of a direction of positioning movement of the seat and controlling the positioning movement of the actuator relative to the seat in response to the selection of a direction of positioning movement of the actuator.

29. The method of claim 28, wherein said seat positioning movement controlling step consists of the steps of moving the seat in a horizontal direction relative to said actuator and moving the seat in a vertical direction relative to said actuator, and wherein said actuator positioning movement controlling step consists of the steps of moving the actuator in a horizontal direction relative to said seat and moving the actuator in a vertical direction relative to said seat.

30. The method of claim 25, wherein said indicating step comprises the step of illuminating a light emitting diode.

31. The method of claim 25, wherein said indicating step comprises the step of displaying on said display device an indication of the direction of positioning movement of the seat and the actuator.

32. A method for positioning a patient on a muscle exercise machine having patient supporting means, an exercise element adapted for manipulation by a patient, a data processor for controlling positioning movement of the patient supporting means and the actuator, and a display device, data storage means, and an input device operationally connected to the data processor, said method comprising the steps of:
    storing in said data storage means names of exercises and relative positions of the patient supporting means and the exercise element;
    indicating a direction of positioning movement of the patient supporting means and the exercise element based upon the relative position of the patient supporting means and the exercise element stored in said data storage means;
    accepting selection of the position of the patient supporting means and the exercise element in response to the indicated direction of positioning movement of the patient supporting means and the exercise element; and
    controlling the relative positioning movement of the patient supporting means and the exercise element in response to the accepted selection of the position of the patient supporting means and the exercise element.

33. The method of claim 32, wherein said controlling step comprises the step of identifying the relative position of the patient supporting means and the exercise element.

34. The method of claim 33, wherein said storing step comprises the steps of storing in said data storage means names of patients in association with names of exercises and the relative positions of said patient supporting means and said exercise element for exercises, said patient positioning method for a muscle exercise machine further comprising the step of:
    controlling the positioning indication positioning of a direction of positioning movement in response to the relative position of the patient supporting means and the exercise element stored in said data storage means and the relative position of the patient supporting means and the exercise element identified by said identifying step.

35. A method of controlling positioning a patient on a muscle exercise machine having patient supporting means, an exercise element adapted for manipulation by a patient, a data processor operationally connected to said patient supporting means and said exercise element, and a display device, data storage means, and an input device operationally connected to said data processor, said method comprising the steps of:
    effecting relative positioning movement between said patient supporting means and said exercise element to define an exercise position wherein said relative positioning movement effecting step comprises the steps of:
        accepting user selection of a relative position of said exercise element and said patient supporting means;
        indicating a direction of relative positioning movement of said exercise element and said patient supporting means; and
        automatically effecting positioning movement of at least one of said patient supporting means and said exercise element; and
    storing in said data storage means patient names and associated patient exercise names; and
    storing in said data storage means, an exercise position corresponding to a patient name and a patient exercise name
    wherein positioning movement of at least one of said patient supporting means and said exercise element to an exercise position stored in said data storage means is automatically effected.

36. The method of claim 35, wherein said exercise position storing step further comprises the step of automatically storing an exercise position defined by said relative positioning movement effecting step in said data storage device.

37. The method of claim 36, wherein said automatically effecting positioning movement step comprises the step of
automatically effecting positioning movement of at least one of said exercise element and said patient supporting means to the selected relative position of said exercise element and said patient positioning means.

38. The method of claim 35, wherein said automatically positioning step activates effecting positioning movement movement of at least one of said patient supporting means and said exercise element to an exercise position stored in said data storage means in response to said accepting user selection step.

39. The method of claim 38, wherein said automatically effecting positioning movement step discontinues positioning movement of said at least one of said patient supporting means and said exercise element to said exercise position upon deactivation of user selection acceptance step.

* * * * *

UNITED STATES PATENT AND TRADEMARK OFFICE
CERTIFICATE OF CORRECTION

PATENT NO. : 5,403,251

DATED : April 4, 1995

INVENTOR(S) : Belsito et al.

It is certified that error appears in the above-identified patent and that said Letters Patent is hereby corrected as shown below:

TITLE PAGE

Item:[54] "CONTROLED" should be -- CONTROLLED --.

Item:[56] References Cited

On the date for Patent No. 4,976,435, "11/1990" should be -- 12/1990 --.

Column 1, in the title, "CONTROLED" should be -- CONTROLLED --.

Column 1, line 36, "results" should be -- result --.

Column 4, line 28, "node" should be -- mode --.

Column 21, line 21, "a" should be -- at --.

Column 22, line 18, after "switch" insert -- , --.

Column 23, line 42, "take" should be -- the --.

Column 24, line 57, "280" should be -- 280 --.

UNITED STATES PATENT AND TRADEMARK OFFICE
CERTIFICATE OF CORRECTION

PATENT NO. : 5,403,251
DATED : April 4, 1995
INVENTOR(S) : Belsito et al.

It is certified that error appears in the above-identified patent and that said Letters Patent is hereby corrected as shown below:

Column 30, line 51, "arid" should be -- and --.

Column 36, line 31, delete "positioning" (both occurrences).

Column 38, line 2, delete "positioning step activates"; line 3, delete "movement" (second occurrence) and insert -- step activates poisitioning movement --.

Signed and Sealed this

Thirteenth Day of June, 1995

*Attest:*

BRUCE LEHMAN

*Attesting Officer*  *Commissioner of Patents and Trademarks*